United States Patent
Cai et al.

(10) Patent No.: US 12,415,832 B2
(45) Date of Patent: Sep. 16, 2025

(54) B-CATENIN/B-CELL LYMPHOMA 9 PROTEIN-PROTEIN INTERACTION INHIBITING PEPTIDOMIMETICS

(71) Applicants: University of South Florida, Tampa, FL (US); H. LEE MOFFITT CANCER CENTER AND RESEARCH INSTITUTE INC., Tampa, FL (US)

(72) Inventors: Jianfeng Cai, Tampa, FL (US); Peng Sang, Tampa, FL (US); Yan Shi, Tampa, FL (US); Haitao Ji, Tampa, FL (US); Min Zhang, Tampa, FL (US)

(73) Assignees: UNIVERSITY OF SOUTH FLORIDA, Tampa, FL (US); H. LEE MOFFITT CANCER CENTER AND RESEARCH INSTITUTE INC., Tampa, FL (US)

( * ) Notice: Subject to any disclaimer, the term of this patent is extended or adjusted under 35 U.S.C. 154(b) by 997 days.

(21) Appl. No.: 17/605,219

(22) PCT Filed: Apr. 24, 2020

(86) PCT No.: PCT/US2020/029730
§ 371 (c)(1),
(2) Date: Oct. 20, 2021

(87) PCT Pub. No.: WO2020/219819
PCT Pub. Date: Oct. 29, 2020

(65) Prior Publication Data
US 2022/0220153 A1    Jul. 14, 2022

Related U.S. Application Data

(60) Provisional application No. 62/837,911, filed on Apr. 24, 2019.

(51) Int. Cl.
C07K 7/02      (2006.01)
A61K 38/08    (2019.01)
A61K 45/06    (2006.01)
A61P 35/00    (2006.01)
A61K 38/00    (2006.01)

(52) U.S. Cl.
CPC ............... *C07K 7/02* (2013.01); *A61K 38/08* (2013.01); *A61K 45/06* (2013.01); *A61P 35/00* (2018.01); *A61K 38/00* (2013.01)

(58) Field of Classification Search
CPC .......... C07K 7/02; A61K 38/08; A61K 45/06; A61K 38/00; A61P 35/00; C07D 495/04; C07D 311/80
See application file for complete search history.

(56) References Cited

U.S. PATENT DOCUMENTS 8,957,026 B2    2/2015    Verdine et al.
2019/0062378 A1    2/2019    Ly et al.

OTHER PUBLICATIONS

Li et al, J.Med.Chem., 2015, 58, 4802-4811 (Year: 2015).*
Li et al., Helical Antimicrobial Sulfono-γ-AApeptides, Journal of Medicinal Chemistry, 2015, 58(11):4802-4811.
Sang et al., Inhibition of β-catenin/B Cell Lymphoma 9 Protein—Protein Interaction Using α-helix-mimicking sulfono-γ-AApeptide Inhibitors, Proceedings of the National Academy of Sciences, 2019, 116(22):10757-10762.
Teng et al., γ-AApeptides as a New Class of Peptidomimetics, Chemistry, 2016, 22(16):5458-5466.
PCT International Search Report and Written Opinion, PCT/US2020/29730, Aug. 4, 2020, 13 pages.
Adachi et al., Role of a BCL9-related β-catenin-binding Protein, B9L, in Tumorigenesis Induced by Aberrant Activation of Wnt Signaling, Cancer Research, 2004, 64(23):8496-8501.
Anastas et al., WNT Signalling Pathways as Therapeutic Targets in Cancer, Nature Reviews Cancer, 2013, 13(1):11-26.
Arkin et al., Small-Molecule Inhibitors of Protein-Protein Interactions: Progressing Toward the Reality, Chemistry & Biology, 2014, 21(9):1102-1114.
Azzarito et al., Inhibition of α-helix-mediated Protein-Protein Interactions Using Designed Molecules, Nature Chemistry, 2013, 5(3):161-173.
Barnard et al., Selective and Potent Proteomimetic Inhibitors of Intracellular Protein-Protein Interactions, Angew. Chem. Int. Ed., 2015, 54:2960-2965.
Buratto et al., Structure of a Complex Formed by a Protein and a Helical Aromatic Oligoamide Foldamer at 2.1 Å Resolution, Angew. Chem. Int. Ed., 2014, 53:883-887.
Cheloha et al., Backbone Modification of a Polypeptide Drug Alters Duration of Action In Vivo, Nature Biotechnology, 2014, 32(7):653-655.
Collie et al., Shaping Quaternary Assemblies of Water-Soluble Non-Peptide Helical Foldamers by Sequence Manipulation, Nature Chemistry, 2015, 7(11):871-878.
De La Roche et al., The Function of BCL9 in Wnt/β-catenin Signaling and Colorectal Cancer Cells, BMC Cancer, 2008, 8:199, pp. 1-13.
De La Roche et al., An Intrinsically Labile α-helix Abutting the BCL9-binding Site of β-catenin is Required for its Inhibition by Carnosic Acid, Nature Communications, 2012, 3:680, pp. 1-10.

(Continued)

*Primary Examiner* — Sudhakar Katakam
(74) *Attorney, Agent, or Firm* — Husch Blackwell LLP

(57) ABSTRACT

Disclosed herein is a series of helical sulfono-γ-AApeptides that mimic the binding mode of the α-helical HD2 domain of B-Cell Lymphoma 9 (BCL9). As disclosed herein, sulfono-γ-AApeptides can structurally and functionally mimic the α-helical domain of BCL9, and selectively disrupt β-catenin/BCL9 PPIs with even higher potency. More intriguingly, these sulfono-γ-AApeptides can enter cancer cells, bind with β-catenin and disrupt β-catenin/BCL PPI, and exhibit excellent cellular activity, which is much more potent than the BCL9 peptide. Furthermore, enzymatic stability studies demonstrated the remarkable stability of the helical sulfono-γ-AApeptides, with no degradation in the presence of pronase for 24 h, augmenting their biological potential.

13 Claims, 46 Drawing Sheets
Specification includes a Sequence Listing.

(56) References Cited

OTHER PUBLICATIONS

Dietrich et al., Cell Permeable Stapled Peptide Inhibitor of Wnt Signaling that Targets β-catenin Protein-Protein Interactions, Cell Chemical Biology, 2017, 24(8):958-968.
Ernst et al., Design and Application of an α-Helix-Mimetic Scaffold Based on an Oligoamide-Foldamer Strategy: Antagonism of the Bak BH3/Bcl-xL Complex, Angewandte Chemie, 2003, 115(5):553-557.
Fan et al., SOX7 Suppresses Wnt Signaling by Disrupting β-Catenin/BCL9 Interaction, DNA and Cell Biology, 2018, 37(2):126-132.
Fuchs et al., Proline Primed Helix Length as a Modulator of the Nuclear Receptor-Coactivator Interaction, Journal of the American Chemical Society, 2013, 135(11):4364-4371.
Grossmann et al., Inhibition of Oncogenic Wnt Signaling Through Direct Targeting of β-catenin, Proceedings of the National Academy of Sciences, 2012, 109(44):17942-17947.
Hamuro et al., De Novo Design of Antibacterial β-peptides, Journal of the American Chemical Society, 1999, 121(51):12200-12201.
Hoggard et al., Rational Design of Selective Small-Molecule Inhibitors for β-catenin/B-cell Lymphoma 9 Protein-Protein Interactions, Journal of the American Chemical Society, 2015, 137(38):12249-12260.
Hook et al., The Proteolytic Stability of 'Designed' β-Peptides Containing α-Peptide-Bond Mimics and of Mixed α, β-Peptides: Application to the Construction of MHC-Binding Peptides, Chemistry & Biodiversity, 2005, 2(5):591-632.
Jones et al., Length-Dependent Formation of Transmembrane Pores by 310-helical α-aminoisobutyric Acid Foldamers, Journal of the American Chemical Society, 2016, 138(2):688-695.
Kawamoto et al., Analysis of the Interaction of BCL9 with β-catenin and Development of Fluorescence Polarization and Surface Plasmon Resonance Binding Assays for this Interaction, Biochemistry, 2009, 48(40):9534-9541.
Kawamoto et al., Design of Triazole-Stapled BCL9 α-helical Peptides to Target the β-catenin/B-cell CLL/lymphoma 9 (BCL9) Protein-Protein Interaction, Journal of Medicinal Chemistry, 2012, 55(3):1137-1146.
Mayer et al., Building Proficient Enzymes with Foldamer Prostheses, Angewandte Chemie International Edition, 2014, 53(27):6978-6981.
Nero et al., Oncogenic Protein Interfaces: Small Molecules, Big Challenges, Nature Reviews Cancer, 2014, 14(4):248-262.
Nusse et al., Wnt/β-catenin Signaling, Disease, and Emerging Therapeutic Modalities, Cell, 2017, 169(6):985-999.
Pelay-Gimeno et al., Structure-Based Design of Inhibitors of Protein-Protein Interactions: Mimicking Peptide Binding Epitopes, Angewandte Chemie International Edition, 2015, 54(31):8896-8927.
Sampietro et al., Crystal Structure of a β-catenin/BCL9/Tcf4 Complex, Molecular Cell, 2006, 24(2):293-300.
She et al., De Novo Left-Handed Synthetic Peptidomimetic Foldamers, Angew. Chem. Int. Ed, 2018, 57:9916-9920.
Shi et al., γ-AApeptides: Design, Structure, and Applications, Accounts of Chemical Research, 2016, 49(3):428-441.
Shi et al., One-Bead-Two-Compound Thioether Bridged Macrocyclic γ-AApeptide Screening Library Against EphA2, Journal of Medicinal Chemistry, 2017, 60(22):9290-9298.
Takada et al., Targeted Disruption of the BCL9/β-catenin Complex Inhibits Oncogenic Wnt Signaling, Science Translational Medicine, 2012, 4(148):148ra117-148ra117.
Teng et al., γ-AApeptides as a New Class of Peptidomimetics, Chemistry—A European Journal, 2016, 22(16):5458-5466.
Teng et al., Right-Handed Helical Foldamers Consisting of De Novo D-AApeptides, Journal of the American Chemical Society, 2017, 139(21):7363-7369.
Teng et al., Hydrogen-Bonding-Driven 3D Supramolecular Assembly of Peptidomimetic Zipper, Journal of the American Chemical Society, 2018, 140(17):5661-5665.
Teuscher et al., A Versatile Method to Determine the Cellular Bioavailability of Small-Molecule Inhibitors, Journal of Medicinal Chemistry, 2017, 60(1):157-169.
Van Tienen et al., Constitutive Scaffolding of Multiple Wnt Enhanceosome Components by Legless/BCL9, ELife, 2017, 6:e20882, pp. 1-23.
Wang et al., The Wnt/β-catenin Pathway is Required for the Development of Leukemia Stem Cells in AML, Science, 2010, 327(5973):1650-1653.
Wang et al., Design and High-Resolution Structure of a β3-peptide Bundle Catalyst, Journal of the American Chemical Society, 2014, 136(19):6810-6813.
Wilson et al., Inhibition of Protein-Protein Interactions Using Designed Molecules, Chemical Society Reviews, 2009, 38(12):3289-3300.
Wisniewski et al., Structure-Based Design of 1, 4-dibenzoylpiperazines as β-catenin/B-cell Lymphoma 9 Protein-Protein Interaction Inhibitors, ACS Medicinal Chemistry Letters, 2016, 7(5):508-513.
Wolffs et al., Helical Aromatic Oligoamide Foldamers as Organizational Scaffolds for Photoinduced Charge Transfer, Journal of the American Chemical Society, 2009, 131(13):4819-4829.
Wu et al., Rapid Access to Multiple Classes of Peptidomimetics from Common γ-AApeptide Building Blocks, European Journal of Organic Chemistry, 2014, 2014(8):1760-1765.
Wu et al., The Synthesis of Head-to-Tail Cyclic Sulfono-γ-AApeptides, Organic & Biomolecular Chemistry, 2015, 13(3):672-676.
Zhang et al., AlphaScreen Selectivity Assay for β-catenin/B-cell Lymphoma 9 Inhibitors, Analytical Biochemistry, 2015, 469:43-53.
Zhang et al., Structure-Based Optimization of Small-Molecule Inhibitors for the β-catenin/B-cell Lymphoma 9 Protein-Protein Interaction, Journal of Medicinal Chemistry, 2018, 61(7):2989-3007.
Zhao et al., miR-30-5p Functions as a Tumor Suppressor and Novel Therapeutic Tool by Targeting the Oncogenic Wnt/β-catenin/BCL9 Pathway, Cancer Research, 2014, 74(6):1801-1813.

* cited by examiner

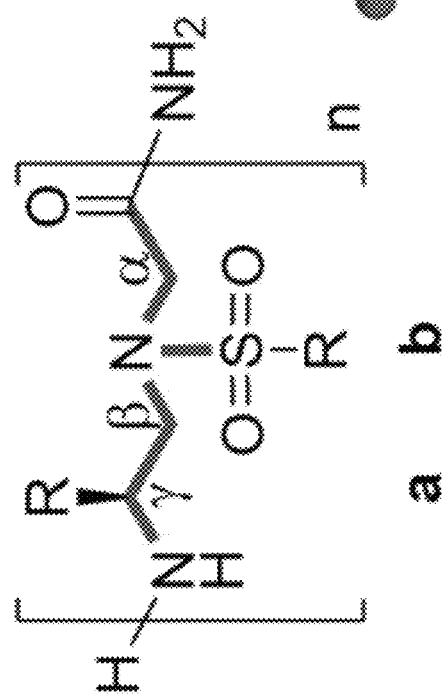
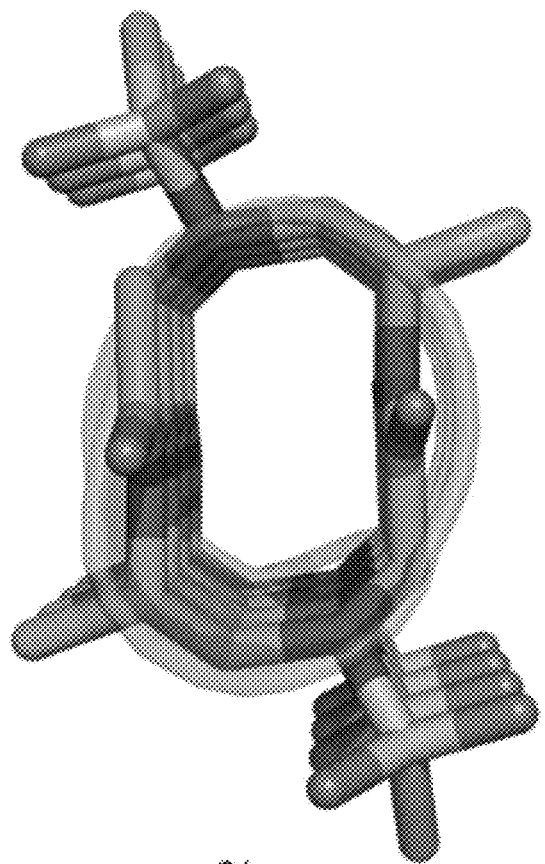
FIG. 1A
FIG. 1C

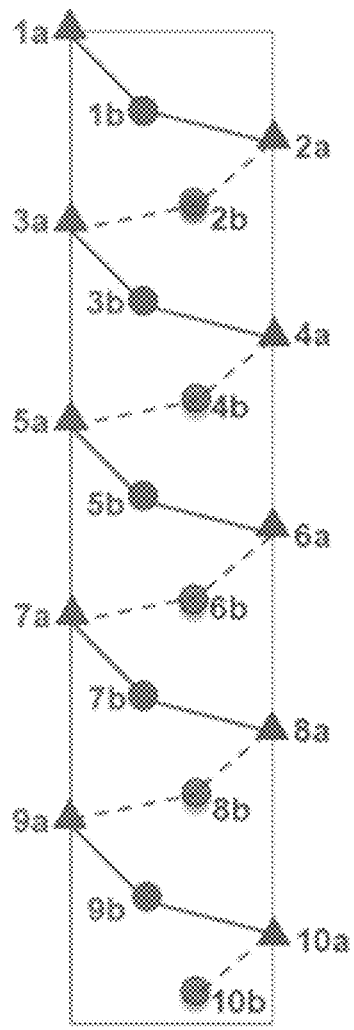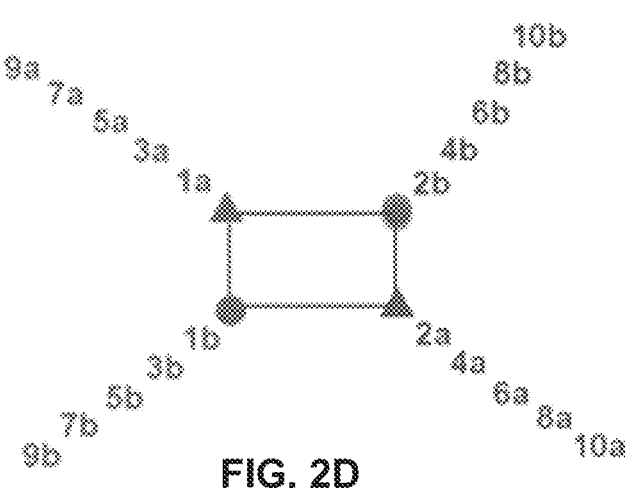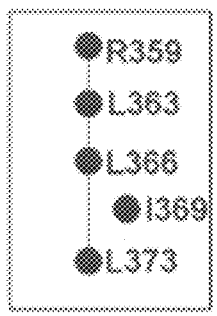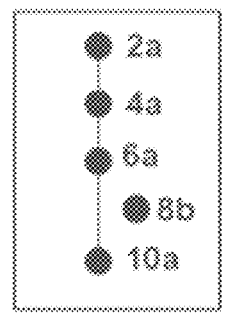
FIG. 2C  FIG. 2E  FIG. 2F

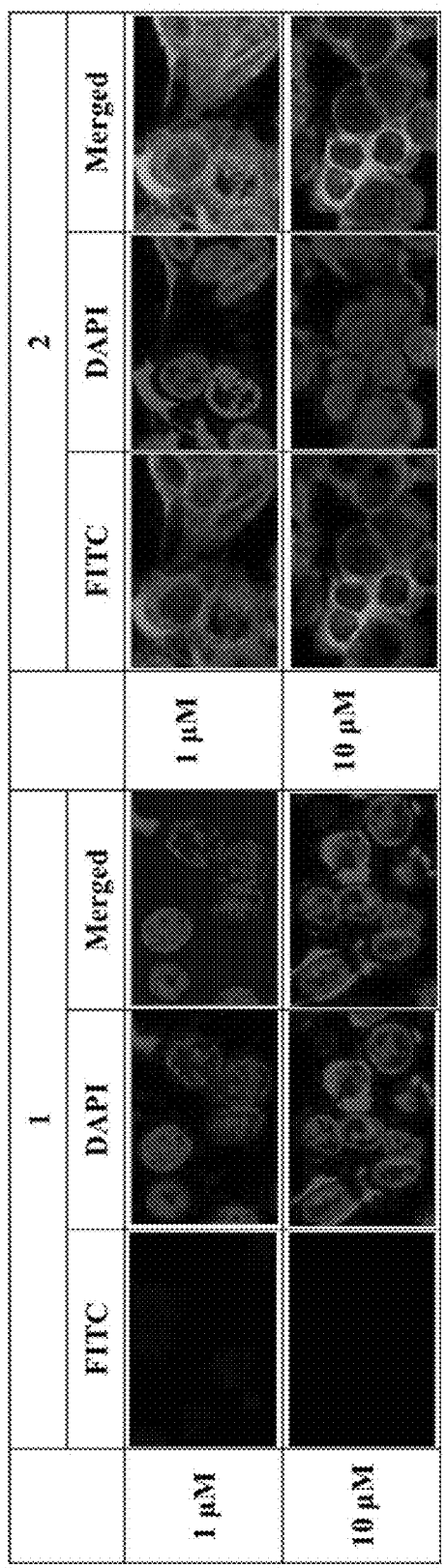
FIG. 12A
FIG. 12B
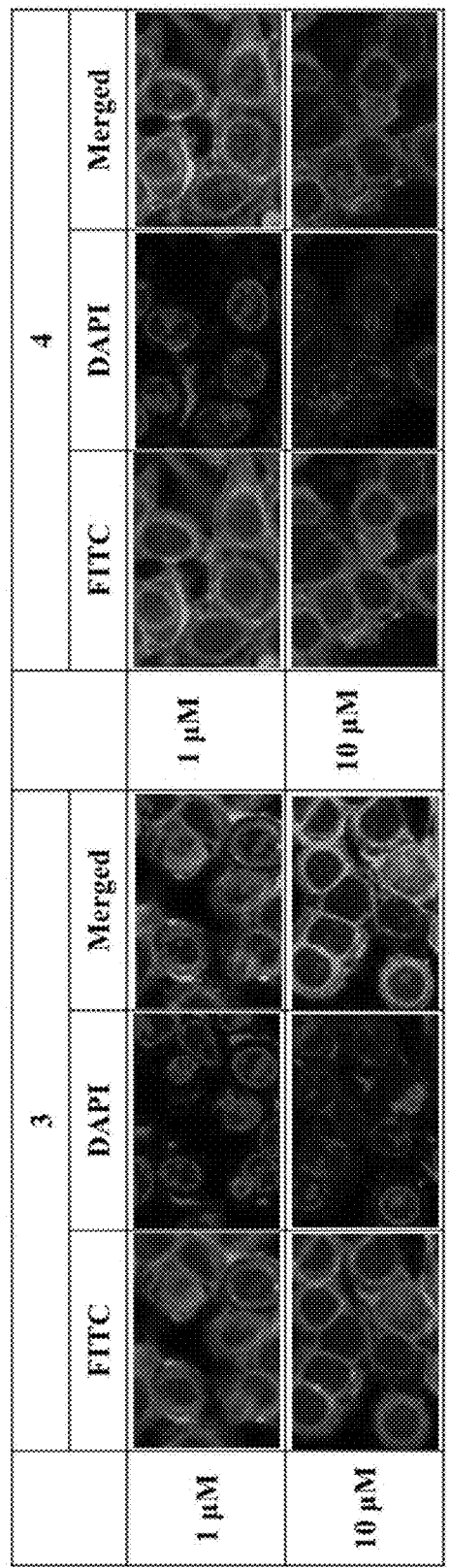
FIG. 12C
FIG. 12D

SEQUENCE LISTING

```
<160> NUMBER OF SEQ ID NOS: 1

<210> SEQ ID NO 1
<211> LENGTH: 23
<212> TYPE: PRT
<213> ORGANISM: Artificial Sequence
<220> FEATURE:
<223> OTHER INFORMATION: Synthetic Construct

<400> SEQUENCE: 1

Ser Gln Glu Gln Leu Glu His Arg Glu Arg Ser Leu Gln Thr Leu Arg
1               5                   10                  15

Asp Ile Gln Arg Met Leu Phe
            20
```

B-CATENIN/B-CELL LYMPHOMA 9 PROTEIN-PROTEIN INTERACTION INHIBITING PEPTIDOMIMETICS

This application is the U.S. National Stage of international application PCT/US2020/029730, filed Apr. 24, 2020 and published as WO/2020/219819, and which claims benefit of U.S. Provisional Application No. 62/837,911, filed Apr. 24, 2019, The content of each of the above-referenced applications is hereby incorporated herein by reference in its entirety.

STATEMENT REGARDING FEDERALLY SPONSORED RESEARCH OR DEVELOPMENT

This invention was made with Government Support under Grant No. GM112652 awarded by the National Institutes of Health and Grant No. 1351265 awarded by the National Science Foundation.

SEQUENCE LISTING

This application contains a sequence listing filed in electronic form as an ASCII.txt file entitled "292104-2180 Sequence Listing_ST25" created on Jan. 20, 2020.

The content of the sequence listing is incorporated herein in its entirety.

BACKGROUND

The rational design of α-helix-mimicking peptidomimetics provides a streamlined approach to discover potent inhibitors for protein-protein interactions (PPIs). However, designing cell-penetrating long peptidomimetic scaffolds equipped with various functional groups necessary for interacting with large protein binding interfaces remains challenging. This is particularly true for targeting β-catenin/BCL9 PPI.

SUMMARY

Disclosed herein is a series of helical sulfono-γ-AApeptides that mimic the binding mode of the α-helical HD2 domain of B-Cell Lymphoma 9 (BCL9). As disclosed herein, sulfono-γ-AApeptides can structurally and functionally mimic the α-helical domain of BCL9, and selectively disrupt β-catenin/BCL9 PPIs with even higher potency. More intriguingly, these sulfono-γ-AApeptides can enter cancer cells, bind with β-catenin and disrupt β-catenin/BCL PPI, and exhibit excellent cellular activity, which is much more potent than the BCL9 peptide. Furthermore, enzymatic stability studies demonstrated the remarkable stability of the helical sulfono-γ-AApeptides, with no degradation in the presence of pronase for 24 h, augmenting their biological potential. This work represents an example of helical sulfono-γ-AApeptides that mimic α-helix and disrupt protein-protein interactions, and an excellent example of potent, selective, and cell-permeable unnatural foldameric peptidomimetics that disrupt the β-catenin/BCL9 PPI. The design of helical sulfono-γ-AApeptides can lead to a new strategy to modulate a myriad of protein-protein interactions in the future.

In particular, disclosed herein is a sulfono-γ-AApeptide compound having the structure of Formula I:

Formula I

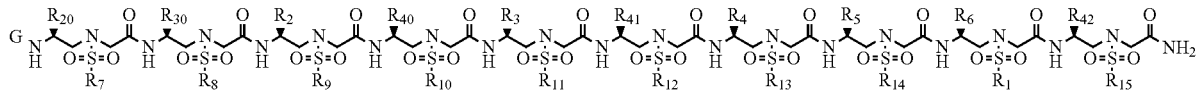

wherein G1 is hydrogen, acetyl group, linker group, or a blocking group;

wherein R1 is a hydrogen or C1-C6 alkyl;

wherein each of R2, R4, and R30 is independently hydrogen, C1-C6 alkyl, or a group having a structure with the formula:

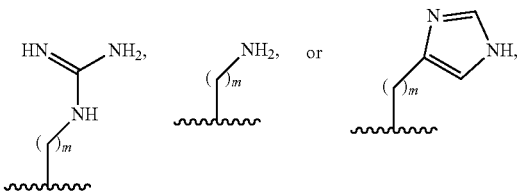

wherein m is an integer having a value of 0, 1, 2, 3, 4, 5, or 6;

wherein each of $R_3$, $R_5$, and $R_6$ is independently hydrogen, C1-C6 alkyl, or C1-C6 hydroxyalkyl;

wherein each of $R_7$, $R_{10}$, and $R_{12}$ is independently hydrogen, C1-C6 alkyl, C1-C6 hydroxyalkyl, or C1-C6 aminoalkyl;

wherein each of $R_8$, $R_9$, $R_{11}$, $R_{13}$, and $R_{14}$ is independently hydrogen or C1-C6 alkyl;

wherein $R_{15}$ is hydrogen, C1-C6 alkyl, aryl, or heteroaryl;

wherein $R_{20}$ is hydrogen, C1-C6 alkyl, C1-C6 hydroxyalkyl, C1-C6 aminoalkyl, —(C1-C6 alkanediyl)-(C=O)OH, or, —(C1-C6 alkanediyl)-(C=O)NH$_2$; and wherein each of $R_{40}$, $R_{41}$, and $R_{41}$ is independently is independently a C1-C6 alkyl;

or a pharmaceutically acceptable salt thereof.

For example, in some embodiments. $G_1$ is acetyl. In some embodiments, $G_1$ is a blocking group. In some embodiments, $G_1$ is an Fmoc group. In some embodiments, $R_1$ is methyl, ethyl, propyl, or isopropyl. In some embodiments, $R_1$ is methyl.

In some embodiments, each of $R_2$, $R_4$, and $R_{30}$ is independently C1-C6 alkyl, or a group having a structure with the formula:

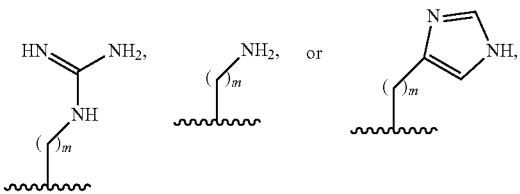

wherein m is an integer having a value of 0, 1, 2, 3, 4, 5, or 6. In some embodiments, each of $R_2$, $R_4$, and $R_{30}$ is independently a group having a structure with the formula:

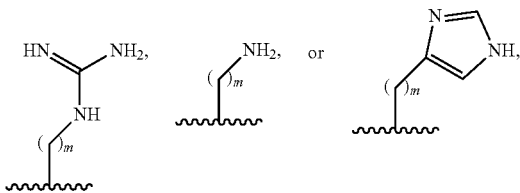

wherein m is an integer having a value of 0, 1, 2, 3, 4, 5, or 6. In some embodiments, each of $R_2$, $R_4$, and $R_{30}$ is independently a group having a structure with the formula:

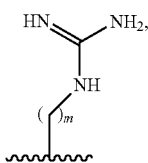

wherein m is an integer having a value of 0, 1, 2, 3, 4, 5, or 6. In some embodiments, each of $R_2$, $R_4$, and $R_{30}$ is a group having a structure with the formula:

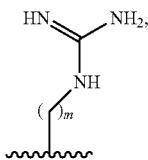

wherein m is an integer having a value of 3.

In some embodiments, each of $R_3$, $R_5$, and $R_6$ is independently C1-C6 alkyl or C1-C6 hydroxyalkyl. In some embodiments, $R_3$ is C1-C6 hydroxyalkyl; and each of $R_5$ and $R_6$ is independently C1-C6 alkyl. In some embodiments, $R_3$ is —(CHOH)CH$_3$; and wherein each of $R_5$ and $R_6$ is independently C1-C6 alkyl. In some embodiments, Ra is C1-C6 hydroxyalkyl; and wherein each of $R_5$ and $R_6$ is independently methyl, ethyl, propyl, isopropyl, butyl, or isobutyl. In some embodiments, $R_3$ is —(CHOH)CH$_3$; and wherein each of $R_5$ and $R_6$ is isobutyl.

In some embodiments, each of $R_7$, $R_{10}$, and $R_{12}$ is independently C1-C6 alkyl, C1-C6 hydroxyalkyl, or C1-C6 aminoalkyl. In some embodiments, each of $R_7$, $R_{10}$, and $R_{12}$ is independently C1-C6 hydroxyalkyl or C1-C6 aminoalkyl. In some embodiments, each of $R_7$, $R_{10}$, and $R_{12}$ is independently a C1-C6 aminoalkyl. In some embodiments, each of $R_7$, $R_{10}$, and $R_{12}$ is —(CH$_2$)$_2$NH$_2$.

In some embodiments, each of $R_8$, $R_9$, $R_{11}$, $R_{13}$, and $R_{14}$ is independently a C1-C6 alkyl. In some embodiments, each of $R_8$, $R_9$, $R_{11}$, $R_{13}$, and $R_{14}$ is independently a C1-C4 alkyl. In some embodiments, each of $R_8$, $R_9$, $R_{11}$, $R_{13}$, and $R_{14}$ is independently a C2-C6 alkyl. In some embodiments, each of $R_8$, $R_9$, $R_{11}$, $R_{13}$, and $R_{14}$ is independently a methyl, butyl, or isobutyl.

In some embodiments, $R_{20}$ is C1-C6 alkyl, aryl, or heteroaryl. In some embodiments. $R_{20}$ is aryl or heteroaryl. In some embodiments, $R_{20}$ is aryl. In some embodiments, $R_{20}$ is benzyl or phenyl. In some embodiments, $R_{20}$ is benzyl.

In some embodiments, each of $R_{40}$, $R_{41}$, and $R_{41}$ is independently a C2-C6 alkyl. In some embodiments, each of $R_{40}$, $R_{41}$, and $R_{41}$ is independently a C3-C6 alkyl. In some embodiments, each of $R_{40}$, $R_{41}$, and $R_{41}$ is independently butyl or isobutyl. In some embodiments, each of $R_{40}$, $R_{41}$, and $R_{41}$ is independently isobutyl.

In some embodiments, the sulfono-γ-AApeptide compound has the structure of Formula II:

Formula II

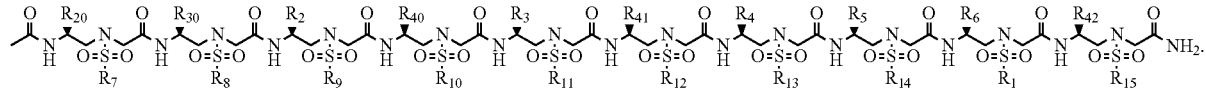

In some embodiments, the sulfono-γ-AApeptide compound has the structure of Formula III:

Formula III

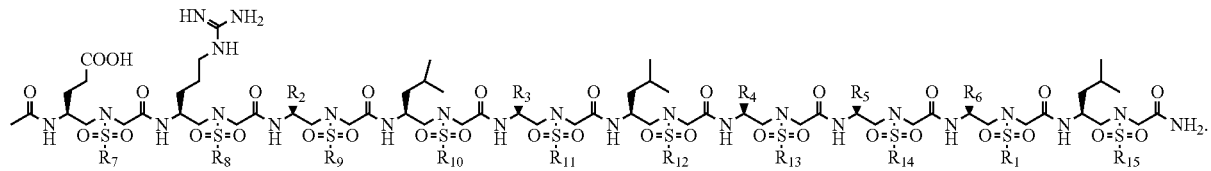

In some embodiments, the sulfono-γ-AApeptide compound has the structure of Formula IV:
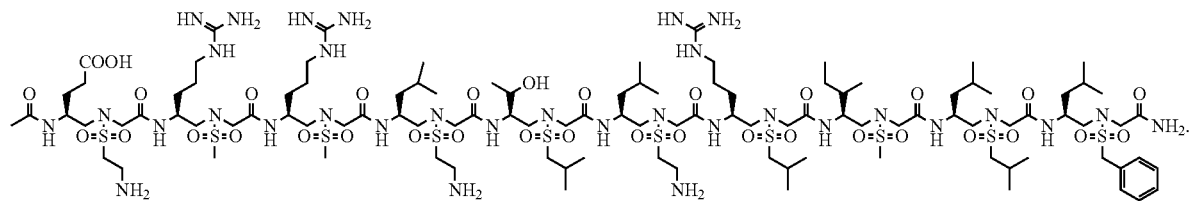
Formula IV
In some embodiments, the sulfono-γ-AApeptide compound has the structure of selected from one of the following formulas:
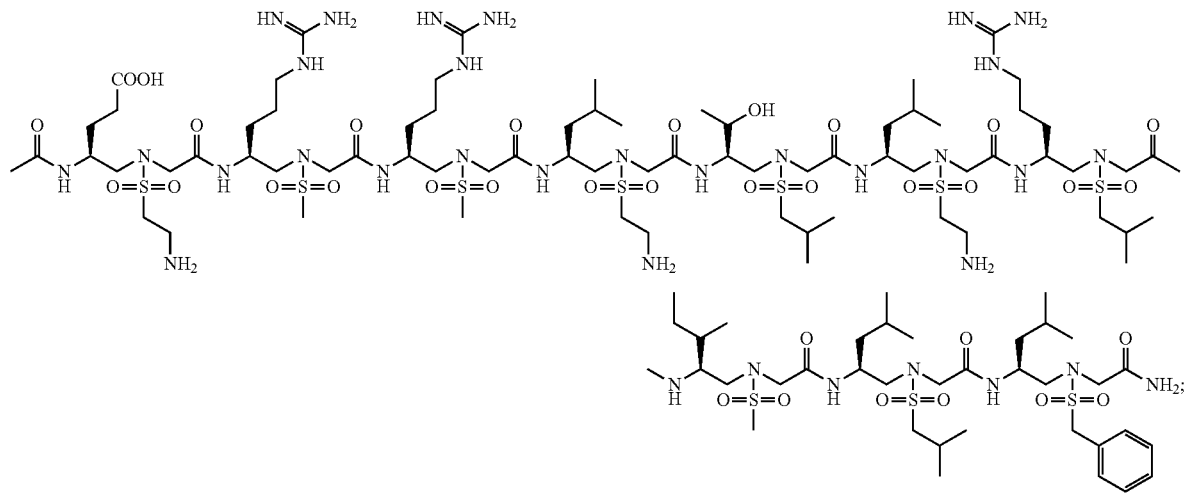
Compound 2
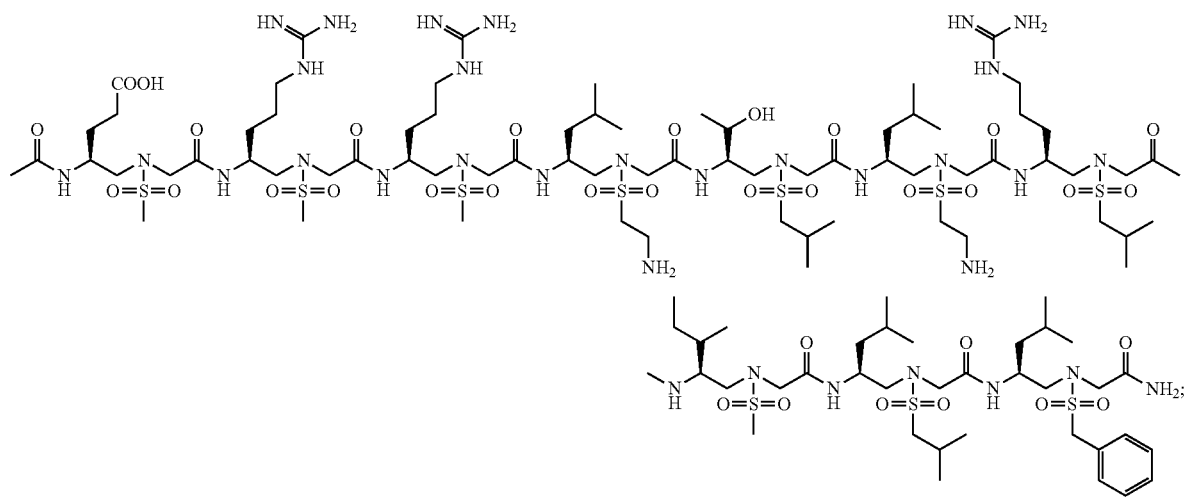
Compound 3

-continued
Compound 4
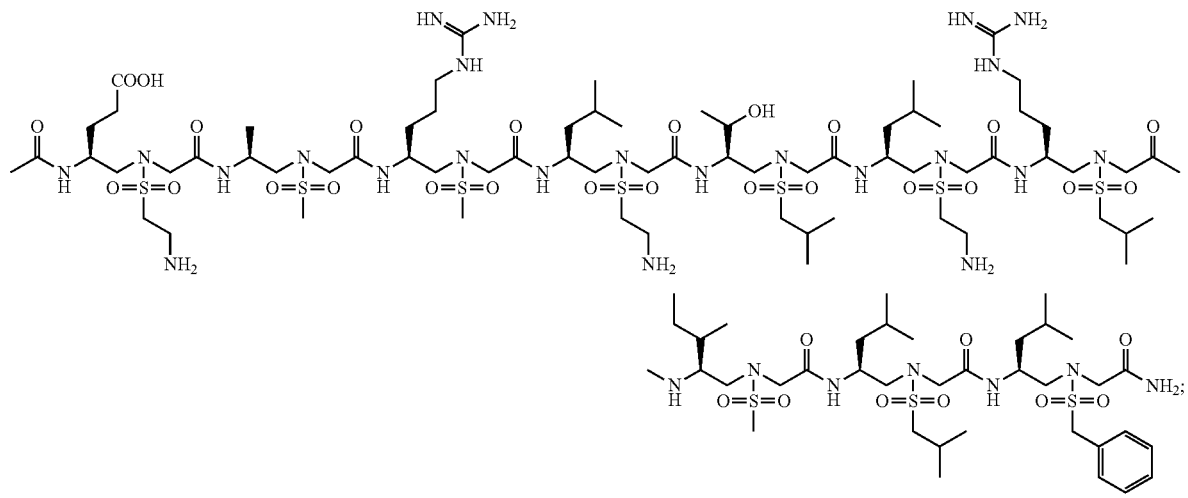
Compound 5
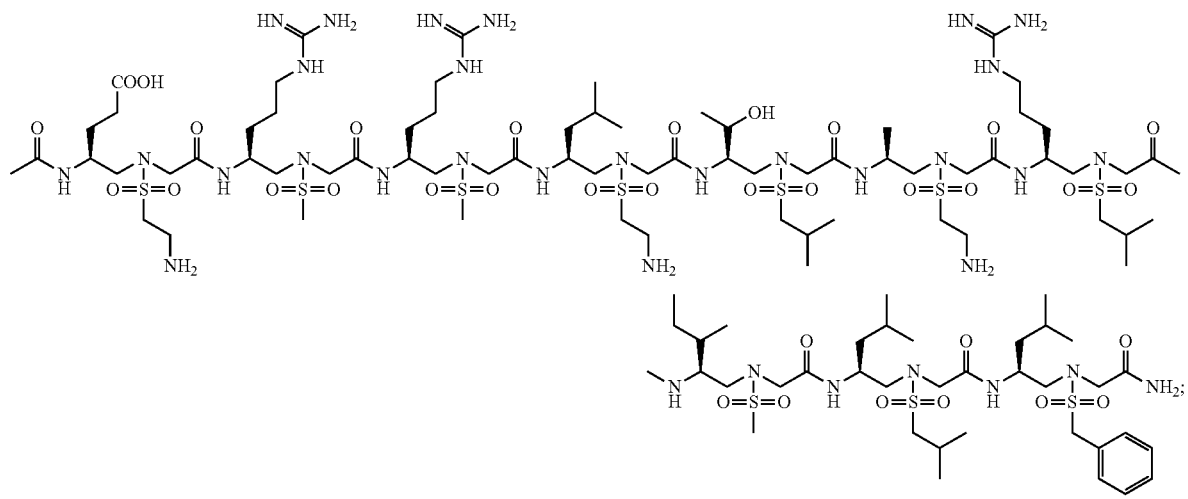
Compound 6
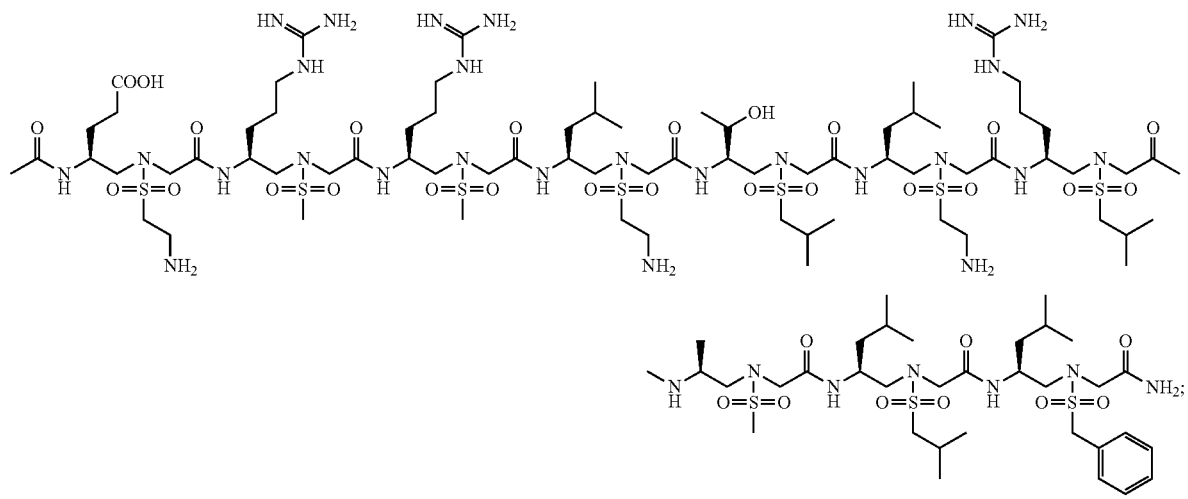

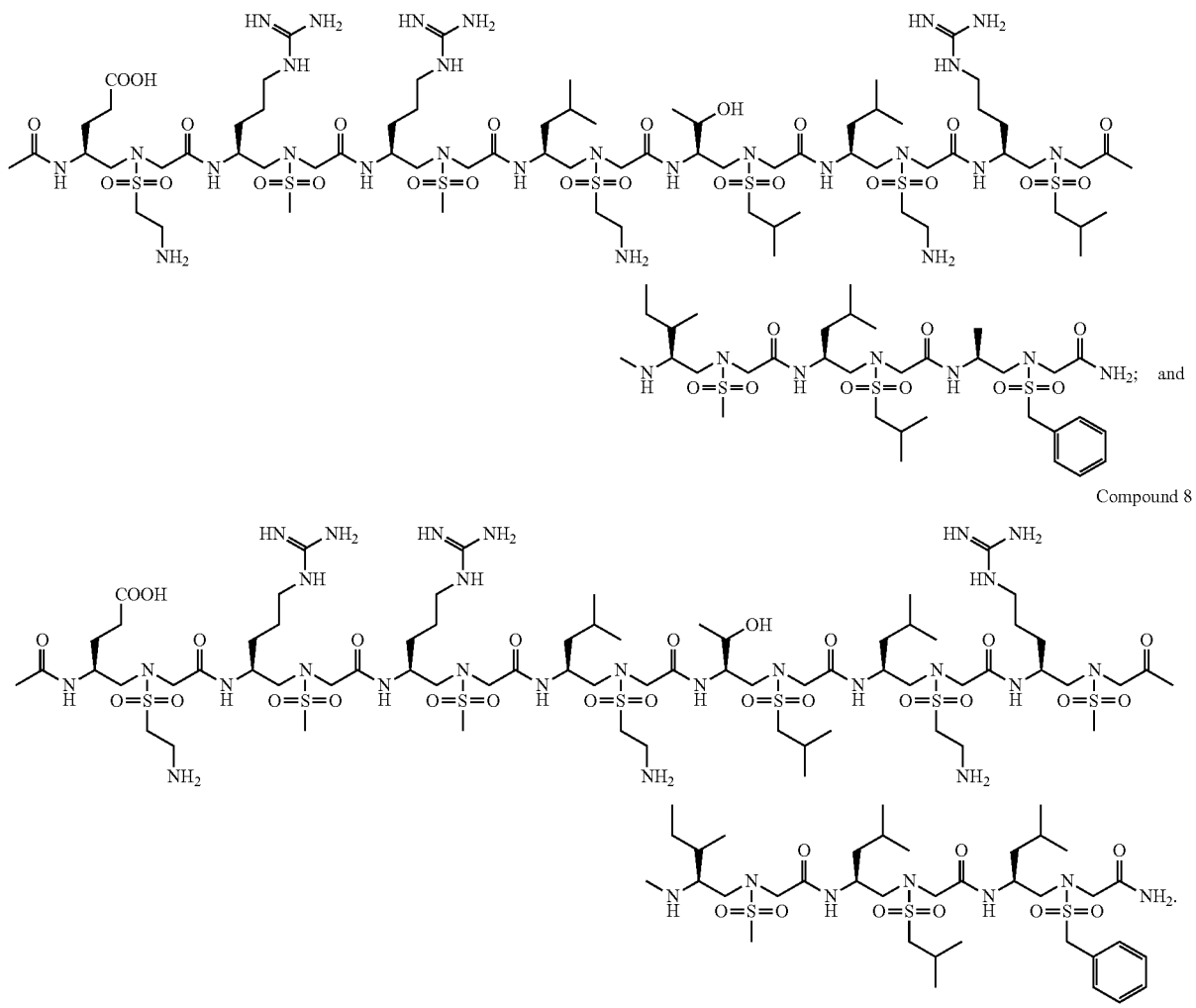

Compound 7

Compound 8

Also disclosed herein is a pharmaceutical composition comprising a sulfono-γ-AApeptide compound disclosed herein, or a pharmaceutically acceptable salt thereof, and a pharmaceutically acceptable excipient.

Also disclosed herein is a method for treating a disease or disorder mediated by BCL9/β-catenin binding in a subject, comprising administering to the subject an effective amount of the disclosed pharmaceutical composition. For example, in some embodiments, the subject has been identified as being in need of an inhibitor of the BCL9/β-catenin interaction or Wnt signaling. In some embodiments, the disease is cancer, tumor cell proliferation, tumor cell de-differentiation and metastasis, tumor migration, tumor induced angiogenesis, cancer stem cell chemoresistance, and a proliferation disease; or involves wound healing, angiogenesis, or diabetes.

Also disclosed is a method for treating cancer in a subject, comprising administering to the subject an effective amount of a sulfono-γ-AApeptide compound disclosed herein, or a pharmaceutically acceptable salt thereof, and a pharmaceutically acceptable excipient. In some embodiments, the method further involves administering to the subject an additional therapeutic agent, radiation or chemotherapy. For example, in some embodiments, the sulfono-γ-AApeptide compound and the additional therapeutic agent are administered simultaneously or sequentially. In some embodiments, the sulfono-γ-AApeptide compound and the additional therapeutic agent are administered in the same pharmaceutical composition.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A shows the chemical structure of sulfono-γ-AApeptides, a and b denote the chiral side chain and the sulfonamido side chain from the building block, respectively. FIG. 1C is a top view of FIG. 1B FIGS. 2A-2B show the α-helical HD2 domain of BCL9, which directly engages a surface groove of β-catenin, provided the template for structural stabilization by hydrocarbon stapling (PDB: 2GL7). FIGS. 2C-2F are schematic representations of distribution of side chains from sulfono-γ-AApeptides. FIG. 2C is aside view; FIG. 2D is a top view, helical wheel; FIG. 2E is a position map of critical residues of BCL9 helix; FIG. 2F is a position map of side chains of sulfono-γ-AApeptides that are designed to mimic residues in FIG. 2E.

FIGS. 12A to 12F are fluorescent microscopy images of SW480 cells treated with 1 μM and 10 μM of the FITC-labeled peptide 1 (FIG. 12A) and sulfono-γ-AApeptides 2 (FIG. 12B), 3 (FIG. 12C), 4 (FIG. 12D), 6 (FIG. 12E) and 9 (FIG. 12F) for 2 h.

DETAILED DESCRIPTION

Figure 1B:
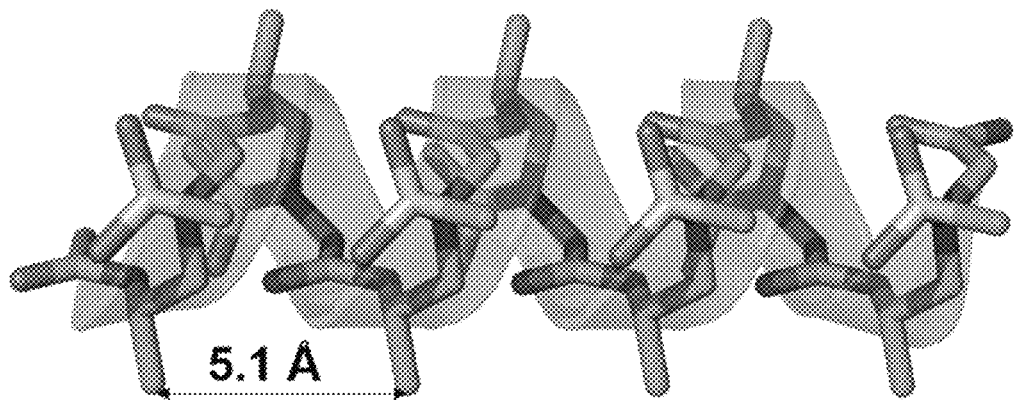
FIG. 1B shows the crystal structure of a sulfono-γ-AApeptide.

Before the present disclosure is described in greater detail, it is to be understood that this disclosure is not limited to particular aspects described, and as such may, of course, vary. It is also to be understood that the terminology used herein is for the purpose of describing particular aspects only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual aspects described and illustrated herein has discrete components and features which may be readily separated from or combined with the features of any of the other several aspects without departing from the scope or spirit of the present disclosure. Any recited method can be carried out in the order of events recited or in any other order that is logically possible.

Aspects of the present disclosure will employ, unless otherwise indicated, techniques of molecular biology, genomics, proteomics, microbiology, nanotechnology, chemistry, organic chemistry, biochemistry, and the like, which are within the skill of the art.

Such techniques are explained fully in the literature.

Definitions

As used herein, As used herein, "about," "approximately," and the like, when used in connection with a numerical variable, can refer to the value of the variable and to all values of the variable that are within the experimental error (e.g., within the 95% confidence interval for the mean) or within +/−10% of the indicated value, whichever is greater.

As used herein, "additive effect" can refer to an effect arising between two or more molecules, compounds, substances, factors, or compositions that is equal to or the same as the sum of their individual effects.

As used herein, "active derivative" and the like can refer to a compound that is capable of mimic the binding mode of the α-helical HD2 domain of B-Cell Lymphoma 9 (BCL9) as provided herein, and thus modulate the Wnt/β-catenin signaling pathway. The term "active derivative" and the like can also refer to a compound or analogue thereof provided herein that can be effective at disrupt β-catenin/BCL9 protein-protein interactions. The term "active derivative: can also refer to a compound or analogue thereof that can be effective at treating a disease or symptom thereof whose pathology involves β-catenin/BCL9 protein-protein interactions. Assays for testing the ability of an active derivative to perform in this fashion are known to those of ordinary skill in the art and provided herein. The assays can include, but are not limited to, in vitro and in vivo assays.

As used herein, the term "peptidomimetics" refers to compounds having a protein-like chain that are designed to mimic peptides, but that have an altered chemistry that does not occur naturally, such as an altered backbone or the incorporation of non-natural amino acids.

As used herein, the term "sulfono-γ-AApeptide" and "sulfono-γ-AApeptide compound" can be used interchangeable and refer herein to a class of peptidomimetic compounds having the backbone structure as shown below:

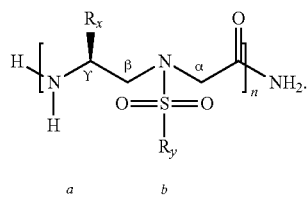

The repeating unit of the sulfono-γ-AApeptide backbone (the "sulfono-γ-AApeptide subunit"), contains two side chains (i.e., the $R_x$ and $R_y$ groups shown in the structure above, denoted with a and b above), one of which is a chiral side chain ($R_x$) and the other is a sulfonamido side chain ($R_y$), respectively. In sulfono-γ-AApeptides, half of the side chains are introduced by sulfonyl chlorides, providing enormous chemical diversity. The term "sulfono-γ-AApeptide compound" refers to compounds of the present disclosure having the sulfono-γ-AApeptide backbone structure shown above, and can include a single sulfono-γ-AApeptide as well as an oligomeric or polymeric sulfono-γ-AApeptide. For instance, aspects of sulfono-γ-AApeptide compounds of the present disclosure include compounds having the structure of Formula 1, below. As used herein, the term "sulfono-γ-AApeptide building block" refers to a compound used in the preparation of a sulfono-γ-AApeptide compound, such as a sulfono-γ-AApeptide. The γ-AApeptide building block can have a protecting group, such as an Fmoc protecting group (fluorenylmethyloxycarbonyl) the sulfono-γ-AApeptide building block will become a sulfono-γ-AApeptide subunit within a longer-chain sulfono-γ-AApeptide compound.

As used herein, "administering" can refer to any administration route, including but not limited to, administration that is oral, topical, intravenous, subcutaneous, transcutaneous, transdermal, intramuscular, intra-articular, parenteral, intra-arterial, intradermal, intraventricular, intracranial, intraperitoneal, intralesional, intranasal, rectal, vaginal, by inhalation, or via an implanted reservoir. The term "parenteral" includes subcutaneous, intravenous, intramuscular, intra-articular, intra-synovial, intrasternal, internasal, intrathecal, intrahepatic, intralesional, and intracranial injections or infusion techniques.

As used herein, "attached," "attachment" and the like can refer to the formation of a covalent or non-covalent association (e.g. a bond) between two or more molecules or conjugation of two or more molecules. As used herein, "attached," "attachment" and the like can refer to direct association of two or more molecules together with no intermediate molecules between those that are attached together or to the indirect attachment of two or more molecules together that is mediated via one or more linkers. Where the association is non-covalent, this can encompass charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. Where the association is covalent, this can encompass bonds where a pair of electrons is shared between one or more atoms in each molecule involved.

As used interchangeably herein, "biocompatible." "biocompatibility," and "biologically compatible" can refer to materials that are, with any metabolites or degradation products thereof, generally non-toxic to the recipient, and cause no significant adverse effects to the recipient. Generally speaking, biocompatible materials are materials which do not elicit a significant inflammatory or immune response when administered to a patient. In some aspects, a biocompatible material elicits no detectable change in one or more biomarkers indicative of an immune response. In some aspects, a biocompatible material elicits no greater than a 10% change, no greater than a 20% change, or no greater than a 40% change in one or more biomarkers indicative of an immune response.

As used herein, "a compound of formula (1), (2), (3), (4), (5), (6), (6a), (6b) (7), (8), (9), (10), (11), (12), (13), (14), (A), (B), (C), (D), and so forth and so on," or "a compound having a structure according to formula (1), (2), (3), (4), (5), (6), (6a), (6b) (7), (8), (9), (10), (11), (12), (13), (14), (A), (B), (C), (D), etc.," compound (1), (2), (3), (4), (5), (6), (6a), (6b) (7), (8), (9), (10), (11), (12), (13), (14), (A), (B), (C), (D), and so forth and so on," or a "compound" can include all or any sub-group of solvates, complexes, polymorphs, derivatives thereof (including but not limited to, radiolabeled derivatives (including deuterated derivatives where one or more H are replaced by D)), tautomers, stereoisomers, and optical isomers of the compound of the formulas listed above and salts thereof.

As used herein, "chemotherapeutic agent" or "chemotherapeutic" can refer to a therapeutic agent utilized to prevent or treat cancer and any other disease that is associated with altered Wnt/β-catenin signaling pathway, Wnt/β-catenin signaling pathway activity or Wnt/β-catenin signaling pathway function.

As used herein, 'control' can refer to an alternative subject or sample used in an experiment for comparison purposes and included to minimize or distinguish the effect of variables other than an independent variable. A control can be positive or negative. One of ordinary skill in the art will appreciate what are appropriate controls for a given context.

As used herein, "concentrated" can refer to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, 'derivative' can refer to substituting, deleting, and/or adding one or more atoms or functional groups. The term "derivative" does not mean that the derivative is synthesized from the parent compound either as a starting material or intermediate, although this may be the case. The term "derivative" can include salts, prodrugs, or metabolites of the parent compound. Derivatives include compounds in which free amino groups in the parent compound have been derivatized to form amine hydrochlorides, p-toluene sulfonamides, benzoxycarboamides, t-butyloxy-carboamides, thiourethane-type derivatives, trifluoroacetyl-amides, chloroacetylamides, or formamides. Derivatives include compounds in which carboxyl groups in the parent compound have been derivatized to form salts, methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imines, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with various side groups.

As used herein, "diluted" can refer to an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used herein, "dose," "unit dose," or "dosage" can refer to physically discrete units suitable for use in a subject, each unit containing a predetermined quantity of a compound as provided herein and/or a pharmaceutical formulation thereof calculated to produce the desired response or responses in association with its administration.

As used herein, "effective amount" can refer to an amount sufficient to effect beneficial or desired results. An effective amount can be administered in one or more administrations, applications, or dosages. "Effective amount" can refer to an amount of a compound, derivative, and/or formulation thereof provided herein that can treat or prevent a disease or symptom thereof whose pathology involves the Wnt/β-catenin signaling pathway. Some diseases include, but are not limited to all cancers that have compromised Wnt/β-catenin signaling pathway activity or function and all those cancers wherein there is dysfunction of the Wnt/β-catenin signaling pathway. The main malignancies include, cancers of the breast, prostate, lung, endometrium, head and neck squamous cell carcinoma (HNSCC), ovary, colon, colo-rectal, lymphoma, mesothelioma, salivary gland, testicular cancers, cancers of the thyroid, skin, stomach, soft tissue sarcoma, cancers of the brain including glioblastomas and astrocytomas, aggressive form of skin cancers such as melanomas, head and neck squamous cell carcinomas.

The β-catenin/BCL9 disrupting peptidomimetic compositions can treat other β-catenin/BCL9-related diseases including all the "β-catenin/BCL9-associated cancers" such as when cancer is a cancer wherein BCL9 and β-catenin are dysfunctional and associated with aberrant cell growth. In some aspects, the cancer is selected from: hepatocellular cancer, liver cancer, gastric cancer, prostate cancer, ovarian cancer, breast cancer, lunc cancer, melanoma, thyroid cancer, medulloblastoma, hepatoblastoma, adrenocortical cancer, colorectal cancer, multiple myeloma, B-cell lymphoma, and non-Hodgkin lymphoma. In other aspects, the cancer is selected from: familial adenomatous polyposis (FAP), ocular cancer, rectal cancer, colon cancer, colorectal cancer, cervical cancer, prostate cancer, breast cancer, bladder cancer, oral cancer, benign and malignant tumors, stomach cancer, liver cancer, pancreatic cancer, lung cancer, corpus uteri, ovarian cancer, prostate cancer, testicular cancer, renal cancer, brain/CNS cancer, throat cancer, multiple myeloma, skin melanoma, acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, neurofibromatosis, tuberous sclerosis, hemangiomas, gastric cancer, ovarian cancer, hepatocellular carcinoma, and lymphangiogenesis. In some aspects, the cancer is colorectal cancer. In some aspects, the cancer is gastric cancer. In some aspects, the cancer is ovarian cancer. In some aspects, the cancer is Hepatocellular carcinoma. In some aspects, the cancer is breast cancer. In some aspects, the cancer is prostate cancer. In some aspects, the cancer is skin melanoma. In some aspects, the cancer is lung cancer.

The term "effective amount" can refer to the amount of a compound provided herein to disrupt β-catenin/BCL9 protein-protein interactions by 1, 2, 3, 4, 5, 6, 7, 8, 9, 10, 12, 15, 20, 25, 30, 35, 40, 45, 50, 55, 60, 65, 70, 75, 90, 85, 90, 95, 100, 125, 150, 175, 200 percent or more. The term "effective amount" can refer to the amount of a compound provided herein to disrupt β-catenin/BCL9 protein-protein interactions by 1, 2, 3, 4, 5, 6, 7, 8, 9, 10, 12, 15, 20, 25, 30, 35, 40, 45, 50, 55, 60, 65, 70, 75, 90, 85, 90, 95, 100, 125, 150, 175, 200 percent or more when the compound is present at a concentration of about 1 μM or less. The term "effective amount" can also be used interchangeable with "pharmaceutically acceptable amount." Pharmaceutically effective amount" or "pharmaceutically effective dose," can refer to the amount of a compound or formulation thereof provided herein that will elicit the biological and/or medical response of a cell, tissue, organ, system, or subject that is being sought by the researcher, veterinarian, medical doctor or other clinician. The pharmaceutically effective amount can vary depending on the compound, formulation the disorder or condition (normal or abnormal) and its severity, the route of administration, time of administration, rate of excretion, drug or compound, judgment of the researcher, veterinarian, medical doctor or other clinician, dosage form, and the age, weight, general health, sex and/or diet of the subject to be treated.

As used herein, "hydrate" can refer to a compound formed by the addition of water. Typically, but not always, this will be crystalline lattice structures that incorporate water molecules. Hydrates include stoichiometric hydrates, as well as compositions containing variable amounts of water.

As used herein, "isolated" means separated from constituents, cellular and otherwise, in which the polynucleotide, peptide, polypeptide, protein, antibody, or fragments thereof, are normally associated with in nature. A non-naturally occurring polynucleotide, peptide, polypeptide, protein, antibody, or fragments thereof, do not require "isolation" to distinguish it from its naturally occurring counterpart.

As used herein, "mitigate" can refer to reducing a particular characteristic, symptom, or other biological or physiological parameter associated with a disease or disorder.

The term "molecular weight", as used herein, can generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "negative control" can refer to a "control" that is designed to produce no effect or result, provided that all reagents are functioning properly and that the experiment is properly conducted. Other terms that are interchangeable with "negative control" include "sham," "placebo," and "mock."

As used herein, "pharmaceutical formulation" can refer to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable" can refer to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration.

As used herein, "pharmaceutically acceptable carrier or excipient" can refer to a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used herein also includes both one and more than one such carrier or excipient. Pharmaceutically acceptable carriers include, but are not limited to, diluents, preservatives, binders, lubricants, disintegrators, swelling agents, fillers, stabilizers, and combinations thereof.

As used herein, "pharmaceutically acceptable salt" can refer to any salt derived from organic and inorganic acids of a compound described herein. Pharmaceutically acceptable salt also refers to a salt of a compound described having an acidic functional group, such as a carboxylic acid functional group, and a base. Pharmaceutically acceptable salt also includes hydrates of a salt of a compound described herein.

As used herein, "positive control" can refer to a "control" that is designed to produce the desired result, provided that all reagents are functioning properly and that the experiment is properly conducted.

As used herein, "protein" as used herein can refer to a molecule composed of one or more chains of amino acids in a specific order. The term protein is used interchangeable with "polypeptide." The order is determined by the base sequence of nucleotides in the gene coding for the protein. Proteins are required for the structure, function, and regulation of the body's cells, tissues, and organs.

As used herein, "purified" or "purify" can be used in reference to a nucleic acid sequence, peptide, or polypeptide that has increased purity relative to the natural environment.

As used herein, "preventative," "preventing," "prevent" and the like can refer to partially or completely delaying and/or precluding the onset or recurrence of a disorder or conditions and/or one or more of its attendant symptoms or barring a subject from acquiring or reacquiring a disorder or condition or reducing a subject's risk of acquiring or reacquiring a disorder or condition or one or more of its attendant symptoms including, but not limited to all cancers that have compromised β-catenin/BCL9 protein-protein interaction and all those cancers wherein there is hyperactivity of the Wnt/β-catenin signaling pathway involving β-catenin/BCL9 protein-protein interactions.

As used herein, "separated" can refer to the state of being physically divided from the original source or population such that the separated compound, agent, particle, chemical compound, or molecule can no longer be considered part of the original source or population.

As used herein, "solvate" refers to a complex of variable stoichiometry formed by a solute (e.g. formulas (1)-(1) (A), (B), (C), (D), or any other compound herein or a salt thereof) and a solvent. Pharmaceutically acceptable solvates may be formed for crystalline compounds wherein solvent molecules are incorporated into the crystalline lattice during crystallization. The incorporated solvent molecules can be water molecules or non-aqueous molecules, such as but not limited to, ethanol, isopropanol, dimethyl sulfoxide, acetic acid, ethanolamine, and ethyl acetate molecules.

As used herein, the term "specific binding" can refer to non-covalent physical association of a first and a second moiety wherein the association between the first and second moieties is at least 2 times as strong, at least 5 times as strong as, at least 10 times as strong as, at least 50 times as strong as, at least 100 times as strong as, or stronger than the association of either moiety with most or all other moieties present in the environment in which binding occurs. Binding of two or more entities may be considered specific if the equilibrium dissociation constant, Kd, is $10^{-3}$ M or less, $10^{-4}$ M or less, $10^{-5}$ M or less, $10^{-8}$ M or less, $10^{-7}$ M or less, $10^{-8}$ M or less, $10^{-9}$ M or less, $10^{-1}$ M or less, $10^{-11}$ M or less, or $10^{-12}$ M or less under the conditions employed, e.g., under physiological conditions such as those inside a cell or consistent with cell survival. In some aspects, specific binding can be accomplished by a plurality of weaker interactions (e.g., a plurality of individual interactions, wherein each individual interaction is characterized by a Kd of greater than $10^{-3}$ M). In some aspects, specific binding, which can be referred to as "molecular recognition," is a saturable binding interaction between two entities that is dependent on complementary orientation of functional groups on each entity. Examples of specific binding interactions include primer-polynucleotide interaction, aptamer-aptamer target interactions, antibody-antigen interactions, avidin-biotin interactions, ligand-receptor interactions, metal-chelate interactions, hybridization between complementary nucleic acids, etc.

As used interchangeably herein, "subject," "individual," or "patient," can refer to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

The terms "sufficient" and "effective," as used interchangeably herein, can refer to an amount (e.g. mass, volume, dosage, concentration, and/or time period) needed to achieve one or more desired result(s). For example, a therapeutically effective amount refers to an amount needed to achieve one or more therapeutic effects.

As used herein, "synergistic effect," "synergism," or "synergy" can refer to an effect arising between two or more molecules, compounds, substances, factors, or compositions that that is greater than or different from the sum of their individual effects.

As used herein, "therapeutic", "treating", "treat," and the like can refer to include partially or completely delaying, alleviating, mitigating or reducing the intensity of one or more attendant symptoms of a disease or condition including, but not limited to, those involving a disclosed peptidomimetic composition that can disrupt β-catenin/BCL9 protein-protein interactions. In some aspects, the disease that can be treated by the compounds provided herein Some diseases include, but are not limited to all cancers that have compromised β-catenin/BCL9 protein-protein interactions and all those cancers wherein there is hyperactivity of the Wnt/β-catenin signaling pathway involving β-catenin/BCL9 protein-protein interactions.

As used herein, "variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally. "Variant" includes functional and structural variants.

As used herein, "alkyl" and "alkylene" refer to a saturated hydrocarbon chain having the specified number of member atoms.

The term "alkyl" can also refer to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups. "Alkyl" also refers to a saturated hydrocarbon chain having the specified number of atoms.

The term "alkyl" (or "lower alkyl") as used herein can include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein can refer to an alkyl group, as defined above, but having from one to ten carbons in its backbone structure. Likewise, "lower alkenyl" and "lower alkynyl" have similar chain lengths.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Cycloalkyls can be substituted in the same manner.

As used herein, "C$_{1-6}$ alkyl" can refer to an alkyl group having any number of member atoms from 1 to 6 member atoms, such as for example 1 to 4 atoms. Other alkyl groups may have any number of member atoms as indicated by the numbers given in the formula, which, like the previous example, can refer to an alkyl group having any number of member atoms within the specified range of member atoms. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

The term "aminoalkyl" specifically refers to an alkyl group that is substituted with one or more amino groups.

The term "hydroxyalkyl" specifically refers to an alkyl group that is substituted with one or more hydroxy groups.

As used herein, "amine" and "amino" (and its protonated form) are art-recognized and refer to both unsubstituted and substituted amines, e.g., a moiety that can be represented by the general formula:

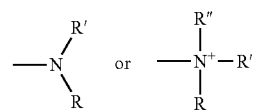

wherein R, R', and R" each independently represent a hydrogen, an alkyl, an alkenyl, —(CH2)$_m$—R$_c$ or R and R' taken together with the N atom to which they are attached complete a heterocycle having from 4 to 8 atoms in the ring structure; $R_c$ represents an aryl, a cycloalkyl, a cycloalkenyl, a heterocycle or a polycycle; and m is zero or an integer in the range of 1 to 8. In some aspects, only one of R or R" can be a carbonyl, e.g., R, R" and the nitrogen together do not form an imide. In other aspects, the term "amine" does not encompass amides, e.g., wherein one of R and R' represents a carbonyl. In further aspects, R and R' (and optionally R") each independently represent a hydrogen, an alkyl or cycloakly, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group.

As used herein, "amido" is art-recognized as an amino-substituted carbonyl and includes a moiety that can be represented by the general formula:

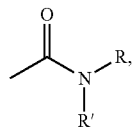

wherein R and R' are as defined above.

As used herein, "aryl" can refer to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics." The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, and combinations thereof.

The term "aryl" can also include polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2, 4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl."

As used herein, "aralkyl," can refer to an alkyl group substituted with an aryl group (e.g., an aromatic or heteroaromatic group).

The term "carbonyl" is art-recognized and includes such moieties as can be represented by the general formula:

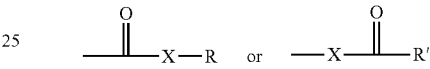

wherein X is a bond or represents an oxygen or a sulfur, and R and R' are as defined above. Where X is an oxygen and R or R" is not hydrogen, the formula represents an "ester". Where X is an oxygen and R is as defined above, the moiety is referred to herein as a carboxyl group, and particularly when R is a hydrogen, the formula represents a "carboxylic acid." Where X is an oxygen and R" is hydrogen, the formula represents a "formate." In general, where the oxygen atom of the above formula is replaced by sulfur, the formula represents a "thiocarbonyl" group. Where X is a sulfur and R or R" is not hydrogen, the formula represents a "thioester." Where X is a sulfur and R is hydrogen, the formula represents a "thiocarboxylic acid." Where X is a sulfur and R" is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

As used herein, "heteroatom" as used herein can refer to an atom of any element other than carbon or hydrogen. Exemplary heteroatoms include, but are not limited to, boron, nitrogen, oxygen, phosphorus, sulfur, silicon, arsenic, and selenium.

The term "substituted" as used herein, can refer to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, e.g. 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms, such as nitrogen, can have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

As used herein, "suitable substituent" can refer to a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents include but are not limited to the following: a halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_2$-$C_6$ alkynyl, $C_3$-$C_8$ cycloalkenyl, ($C_3$-$C_8$ cycloalkyl)$C_1$-$C_6$ alkyl, ($C_3$-$C_8$ cycloalkyl)$C_2$-$C_6$ alkenyl, ($C_3$-$C_8$ cycloalkyl) $C_1$-$C_6$ alkoxy, $C_3$-$C_7$ heterocycloalkyl, ($C_3$-$C_7$ heterocycloalkyl) $C_1$-$C_6$ alkyl, (C3-C7 heterocycloalkyl)$C_2$-$C_6$ alkenyl, ($C_3$-$C_7$ heterocycloalkyl)$C_1$-$C_6$ alkoxyl, hydroxy, carboxy, oxo, sulfanyl, $C_1$-$C_6$ alkylsulfanyl, aryl, heteroaryl, aryloxy, heteroaryloxy, arylalkyl, heteroaralkyl, arylalkoxy, heteroaralkoxy, nitro, cyano, amino, $C_1$-$C_6$ alkylamino, di-($C_1$-$C_6$ alkyl)amino, carbamoyl, ($C_1$-$C_6$ alkyl)carbonyl, ($C_1$-$C_6$ alkoxy)carbonyl, ($C_1$-$C_6$ alkyl)aminocarbonyl, di-($C_1$-$C_6$ alkyl)aminocarbonyl, arylcarbonyl, aryloxycarbonyl, ($C_1$-$C_6$ alkyl)sulfonyl, and arylsulfonyl. The groups listed above as suitable substituents are as defined hereinafter except that a suitable substituent may not be further optionally substituted.

As used herein, "optionally substituted" can indicate that a group may be unsubstituted or substituted with one or more substituents as defined herein.

Discussion

Deregulated Wnt/β-catenin signaling underlies the pathogenesis of a broad range of human cancers, yet the development of targeted therapies to disrupt the resulting aberrant transcription has proved difficult because the pathway comprises large protein interaction surfaces and regulates many homeostatic functions. Therefore, there has been an effort to block the interaction of β-catenin with B cell lymphoma 9 (BCL9), a co-activator for β-catenin-mediated transcription that is highly expressed in tumors but not in the cells of origin. BCL9 drives β-catenin signaling through direct binding mediated by its α-helical homology domain 2. A stabilized α helix of BCL9 (SAH-BCL9) has previously been shown to target β-catenin, dissociate native β-catenin/BCL9 complexes, selectively suppress Wnt transcription, and exhibits mechanism-based antitumor effects. SAH-BCL9 also suppresses tumor growth, angiogenesis, invasion, and metastasis in mouse xenograft models of Colo320 colorectal carcinoma and INA-6 multiple myeloma. However, a cell-penetrating peptidomimetic capable of inhibiting β-catenin/BCL9 would be highly valuable due to the potential for enhanced resistance to proteolytic degradation.

β-Catenin/BCL9 Disrupting Peptidomimetic Compositions

As a new class of proteolytically stable peptidomimetics, γ-AApeptides have emerged as effective peptidomimetics that play an important role in chemical biology and biomedical sciences. Specifically, sulfono-γ-AApeptides have been shown to have excellent folding stability to adopt a series of helical structures with a well-defined hydrogen bonding pattern. In sulfono-γ-AApeptides, half of the side chains are introduced by sulfonyl chlorides, providing enormous chemical diversity (FIG. 1A). Intriguingly, the side chains of sulfono-γ-AApeptides are aligned perfectly on the top of each other with a pitch of 5.1 Å. Based on the precise three dimensional arrangement of their side functional groups, their close similarity in helical pitch compared to that of α-helix (5.4 Å), as well as the remarkable stability of sulfono-γ-AApeptides, helical sulfono-γ-AApeptides represent a new class of helical mimetics that can be used to disrupt α-helix-mediated protein-protein interactions.

Pharmaceutical Formulations

Also provided herein are pharmaceutical formulations that can contain an amount of a disclosed peptidomimetic composition capable of disrupting β-catenin/BCL9 protein-protein interactions (collectively also referred to as "β-catenin/BCL9 disrupting peptidomimetic compositions") as provided elsewhere herein. The β-catenin/BCL9 disrupting peptidomimetic composition described herein can be provided to a subject in need thereof alone or as such as an active ingredient, in a pharmaceutical formulation. In some aspects, the pharmaceutical formulations contain an effective amount of a β-catenin/BCL9 disrupting peptidomimetic composition. The pharmaceutical formulations described herein can be administered to a subject in need thereof. The subject in need thereof can have a disease or disorder whose pathology involves an aberrant or dysfunctional Wnt/β-catenin signaling pathway comprising a β-catenin/BCL9 protein-protein interaction. In some aspects the disease is a cancer occurring in multiple organs. These include all cancers that have compromised β-catenin/BCL9 protein-protein interactions and all those cancers wherein there is hyperactivity of the Wnt/β-catenin signaling pathway comprising a β-catenin/BCL9 protein-protein interaction.

Pharmaceutically Acceptable Carriers and Auxiliary Ingredients and Agents

The pharmaceutical formulations containing an effective amount of β-catenin/BCL9 disrupting peptidomimetic composition described herein can further include a pharmaceutically acceptable carrier. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

In addition to the effective amount of a β-catenin/BCL9 disrupting peptidomimetic composition described herein, the pharmaceutical formulation can also optionally include an effective amount of an auxiliary active agent, including but not limited to, DNA, RNA, amino acids, peptides, polypeptides, antibodies, aptamers, ribozymes, guide sequences for ribozymes that inhibit translation or transcription of essential tumor proteins and genes, chemotherapeutic agent, anti-cancer agent, and different types of bioavailable nanoparticles encapsulating the compounds for optimal delivery.

Effective Amounts of the PTEN Binding Compounds and Auxiliary Agents

The pharmaceutical formulations can contain an effective amount of a β-catenin/BCL9 disrupting peptidomimetic composition(s), and optionally, a therapeutically effective amount of an auxiliary agent. In some aspects, the effective amount of the β-catenin/BCL9 disrupting peptidomimetic composition(s) can range from about 0.3 mg/kg body weight to about 30 mg/kg. The effective amount of the β-catenin/BCL9 disrupting peptidomimetic composition(s) can range from about 1 mg to about 10 g. For liquid formulations, some aspects, the effective amount of the β-catenin/BCL9 disrupting peptidomimetic composition(s) or pharmaceutical formulation containing a β-catenin/BCL9 disrupting peptidomimetic composition(s) can range from about 10 µL to about 10 mL. One of skill in the art will appreciate that the exact volume will depend on, inter alia, the age and size of the subject, as well as the location of administration. The effective concentration of the β-catenin/BCL9 disrupting peptidomimetic composition(s) can range from about 1 nM to 1M.

In aspects where an optional auxiliary active agent is included in the pharmaceutical formulation, the therapeutically effective amount of the auxiliary active agent will vary depending on the auxiliary active agent. In some aspects, the therapeutically effective amount of the optional auxiliary active agent can range from 0.001 micrograms to about 1000 milligram. In other aspects, the therapeutically effective amount of the optional auxiliary active agent can range from about 0.01 IU to about 1000 IU. In further aspects, the therapeutically effective amount of the auxiliary active agent can range from 0.001 mL to about 1 mL. In yet other aspects, the therapeutically effective amount of the optional auxiliary active agent can range from about 1% w/w to about 50% w/w of the total pharmaceutical formulation. In additional aspects, the therapeutically effective amount of the optional auxiliary active agent ranges from about 1% v/v to about 50% v/v of the total pharmaceutical formulation. In still other aspects, the therapeutically effective amount of the optional auxiliary active agent ranges from about 1% w/v to about 50% w/v of the total pharmaceutical formulation.

Dosage Forms

In some aspects, the pharmaceutical formulations described herein can be in a dosage form. The dosage forms can be adapted for administration by any appropriate route. Appropriate routes include, but are not limited to, oral (including buccal or sublingual), rectal, epidural, intracranial, intraocular, inhaled, intranasal, topical (including buccal, sublingual, or transdermal), vaginal, intraurethral, parenteral, intracranial, subcutaneous, intramuscular, intravenous, intraperitoneal, intradermal, intraosseous, intracardiac, intraarticular, intracavernous, intrathecal, intravireal, intracerebral, and intracerebroventricular and intradermal. Such formulations can be prepared by any method known in the art.

Dosage forms adapted for oral administration can be discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some aspects, the pharmaceutical formulations adapted for oral administration also include one or more agents which flavor, preserve, color, or help disperse the pharmaceutical formulation. Dosage forms prepared for oral administration can also be in the form of a liquid solution that can be delivered as foam, spray, or liquid solution. In some aspects, the oral dosage form can contain about 10 mg to 10 g of a pharmaceutical formulation containing an effective amount or an appropriate fraction thereof of the β-catenin/BCL9 disrupting peptidomimetic composition(s). The oral dosage form can be administered to a subject in need thereof by a suitable administration method.

Where appropriate, the dosage forms described herein can be microencapsulated. The dosage form can also be prepared to prolong or sustain the release of any ingredient. In some aspects, the β-catenin/BCL9 disrupting peptidomimetic composition(s) can be the ingredient whose release is delayed. In other aspects, the release of an optionally included auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel at al., (Media, PA: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Dosage forms adapted for topical administration can be formulated as ointments, creams, suspensions, lotions, powders, solutions, pastes, gels, sprays, aerosols, or oils. In some aspects for treatments of the eye or other external tissues, for example the mouth or the skin, the pharmaceutical formulations are applied as a topical ointment or cream. When formulated in an ointment, the β-catenin/BCL9 disrupting peptidomimetic composition(s), optional auxiliary active ingredient, and/or pharmaceutically acceptable salt thereof can be formulated with a paraffinic or water-miscible ointment base. In other aspects, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some aspects, the β-catenin/BCL9 disrupting peptidomimetic composition(s), the composition containing the β-catenin/BCL9 disrupting peptidomimetic composition(s), auxiliary active ingredient, and/or pharmaceutically acceptable salt thereof in a dosage form adapted for inhalation is in a particle-size-reduced form that is obtained or obtainable by micronization. In some aspects, the particle size of the size reduced (e.g. micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient, which may be generated by various types of metered dose pressurized aerosols, nebulizers, or insufflators.

In some aspects, the dosage forms are aerosol formulations suitable for administration by inhalation. In some of these aspects, the aerosol formulation contains a solution or fine suspension of the β-catenin/BCL9 disrupting peptidomimetic composition(s) and/or pharmaceutically acceptable salt thereof, and a pharmaceutically acceptable aqueous or non-aqueous solvent. Aerosol formulations can be presented in single or multi-dose quantities in sterile form in a sealed container. For some of these aspects, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other aspects are contained in a pump-atomizer. The pressurized aerosol formulation can also contain a solution or a suspension of the β-catenin/BCL9 disrupting peptidomimetic composition(s) or a pharmaceutical formulation thereof. In further aspects, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses or more are delivered each time.

For some dosage forms suitable and/or adapted for inhaled administration, the pharmaceutical formulation is a dry powder inhalable formulation. In addition to β-catenin/BCL9 disrupting peptidomimetic composition(s), an optional auxiliary active ingredient, and/or pharmaceutically acceptable salt thereof, such a dosage form can contain a powder base such as lactose, glucose, trehalose, manitol, and/or starch. In some of these aspects, the β-catenin/BCL9 disrupting peptidomimetic composition(s), optional auxiliary active ingredient, and/or pharmaceutically acceptable salt thereof is in a particle-size reduced form. In further aspects, a performance modifier, such as L-leucine or another amino acid, cellobiose octaacetate, and/or metals salts of stearic acid, such as magnesium or calcium stearate.

In some aspects, the aerosol formulations are arranged so that each metered dose of aerosol contains a predetermined amount of an active ingredient, such as the one or more of the β-catenin/BCL9 disrupting peptidomimetic composition(s) described herein.

Dosage forms adapted for vaginal administration can be presented as pessaries, tampons, creams, gels, pastes, foams, or spray formulations. Dosage forms adapted for rectal administration include suppositories or enemas.

Dosage forms adapted for parenteral administration and/or adapted for any type of injection (e.g. intravenous, intraocular, intraperitoneal, subcutaneous, intramuscular, intradermal, intraosseous, epidural, intracardiac, intraarticular, intracavernous, intrathecal, intravitreal, intracerebral, and intracerebroventricular) can include aqueous and/or non-aqueous sterile injection solutions, which can contain anti-oxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and resuspended in a sterile carrier to reconstitute the dose prior to administration. Extemporaneous injection solutions and suspensions can be prepared in some aspects, from sterile powders, granules, and tablets.

Dosage forms adapted for ocular administration can include aqueous and/or non-aqueous sterile solutions that can optionally be adapted for injection, and which can optionally contain anti-oxidants, buffers, bacteriostats, solutes that render the composition isotonic with the eye or fluid contained therein or around the eye of the subject, and aqueous and non-aqueous sterile suspensions, which can include suspending agents and thickening agents.

For some aspects, the dosage form contains a predetermined amount of the β-catenin/BCL9 disrupting peptidomimetic composition(s) per unit dose. In an aspect, the predetermined amount of the β-catenin/BCL9 disrupting peptidomimetic composition(s) is an effective amount of the β-catenin/BCL9 disrupting peptidomimetic composition(s). In other aspects, the predetermined amount of the β-catenin/BCL9 disrupting peptidomimetic composition(s) can be an appropriate fraction of the effective amount of the active ingredient. Such unit doses may therefore be administered once or more than once a day. Such pharmaceutical formulations may be prepared by any of the methods well known in the art.

Methods of Using the PTEN Binding Compounds and Formulations Thereof

The β-catenin/BCL9 disrupting peptidomimetic compositions, derivatives, and formulations thereof provided herein can be used to disrupt β-catenin/BCL9 interactions, and/or modulate Wnt/β-catenin signaling pathway involving β-catenin/BCL9 interactions, and/or treat and/or prevent a disease whose pathology involves a β-catenin/BCL9 interaction. In some aspects, the disease can be all types of cancer including those occurring in multiple organs. These include all cancers that have compromised β-catenin/BCL9 interactions and all those cancers wherein there is aberrant activity or dysfunction of the Wnt/β-catenin signaling pathway involving β-catenin/BCL9 interactions.

Also provided herein are methods of treating and/or preventing a disease or symptom thereof in a subject in need thereof that can include the step of administering an amount, such as an effective amount, of one or more S-catenin/BCL9 disrupting peptidomimetic compositions to the subject. The subject can be suffering from a disease whose pathology involves aberrant activity or dysfunction of the Wnt/β-catenin signaling pathway involving β-catenin/BCL9 interactions. In some aspects, the subject in need thereof can have any type of cancers including those occurring in multiple organs. These include all cancers that have compromised β-catenin/BCL9 interactions and all those cancers wherein there is hyperactivity of the Wnt/β-catenin signaling pathway involving β-catenin/BCL9 interactions.

Dysregulation of the Wnt signaling pathway underlies the pathogenesis of a wide range of conditions, such as cancer, wound healing, angiogenesis, or diabetes. In some embodiments, the disclosed compositions and/or methods can be used to treat a condition selected from the group consisting of colorectal cancer, multiple myeloma, lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, and solid tumors.

The cancer of the disclosed methods can in some embodiments be any cell in a subject undergoing unregulated growth, invasion, or metastasis. In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

In some embodiments, the disclosed compounds are used in conjunction with an additional therapeutic agent, radiation or chemotherapy. Numerous anti-cancer drugs are available for combination with the present method and compositions. The majority of chemotherapeutic drugs can be divided in to: alkylating agents, antimetabolites, anthracyclines, plant alkaloids, topoisomerase inhibitors, monoclonal antibodies, and other antitumour agents. All of these drugs affect cell division or DNA synthesis. Some newer agents don't directly interfere with DNA. These include the new tyrosine kinase inhibitor imatinib mesylate (Gleevec® or Glivec®), which directly targets a molecular abnormality in certain types of cancer (chronic myelogenous leukemia, gastrointestinal stromal tumors). In addition, some drugs can be used which modulate tumor cell behavior without directly attacking those cells. Hormone treatments fall into this category of adjuvant therapies.

A number of aspects of the invention have been described. Nevertheless, it will be understood that various modifications may be made without departing from the spirit and scope of the invention. Accordingly, other aspects are within the scope of the following claims.

EXAMPLES

Example 1: Inhibition of β-Catenin/B-Cell Lymphoma 9 Protein-Protein Interaction Using α-Heli Development of peptidomimetic helical foldamers for applications in chemical biology and drug discovery has attracted a vast interest in the field of medicinal chemistry. Helical foldamers are commonly featured with many attractive merits such as enhanced resistance to proteolytic degradation and high sequence diversity (Jones J E, et al. (2016) J. Am. Chem. Soc. 138(2):688-695; Collie G W, et al. (2015) Nat. Chem. 7:871-878; Cheloha R W, et al. (2014) Nat. Biotechnol. 32:653-655; Buratto J, et al. (2014) Angew. Chem. Int. Ed. 53(3):883-887: Mayer C, et al. (2014) Chem. Int. Ed. 53(27):6978-6981; Wang P S P, et al. (2014) J. Am. Chem. Soc. 136(19):6810-6813; Wolffs M, et al. (2009) J. Am. Chem. Soc. 131(13):4819-4829; Hamuro Y, et al. (1999) J. Am. Chem. Soc. 121(51):12200-12201), and have been explored extensively for inhibition of protein-protein interactions (PPIs) (Barnard A, et al. (2015) Angew. Chem. Int. Ed. 54(10):2960-2965; Azzarito V, et al. (2013) Nat. Chem. 5:161-173; Pelay-Gimeno M, et al. Angew. Chem. Int. Ed. 54(31):8896-8927; Fuchs S, et al. (2013) J. Am. Chem. Soc. 135(11):4364-4371; Ernst J T, et al. (2003) Angew. Chem. Int. Ed. 42(5):535-539). Nevertheless, targeting intracellular proteins still poses significant challenges (J. Wilson A (2009) Chem. Soc. Rev. 38(12):3289-3300; Nero T L, et al. (2014) Nat. Rev. Cancer 14:248-262; Arkin Michelle R, et al. (2014) Chem. Biol. 21(9):1102-1114), largely due to the limited availability of molecular frameworks of peptidomimetic peptides. As a new class of proteolytically stable peptidomimetics, γ-AApeptides have emerged as effective peptidomimetics that play an important role in chemical biology and biomedical sciences (Shi Y, et al. (2016) Acc. Chem. Res. 49(3):428-441; Teng P, et al. (2016) Chem.—Eur. J. 22(16):5458-5466; Shi Y, et al. (2017) J. Med. Chem. 60(22):9290-9298). Specifically, sulfono-γ-AApeptides have been shown to have excellent folding stability to adopt a series of helical structures with a well-defined hydrogen bonding pattern (Wu H, et al. (2015) Org. Biomol. Chem. 13(3):672-676; Wu H, Teng P. & Cai J (2014) Eur. J. Org. Chem. 2014(8):1760-1765; Teng P, et al. (2017) J. Am. Chem. Soc. 139(21):7363-7369; Teng P, et al. (2018) J. Am. Chem. Soc. 140(17):5661-5665; She F, et al. (2018) Angew. Chem. Int. Ed. 57(31):9916-9920). In sulfono-γ-AApeptides, half of the side chains are introduced by sulfonyl chlorides, providing enormous chemical diversity (FIG. 1A) (Shi Y, et al. (2016) Acc. Chem. Res. 49(3):428-441: Teng P, et al. (2016) Chem.—Eur. J. 22(16): 5458-5466; Shi Y, et al. (2017) J. Med. Chem. 60(22):9290-9298). Particularly, the X-ray crystal structures of a series of homogeneous L-sulfono-γ-AA foldamers were recently reported (She F, et al. (2018) Angew. Chem. Int. Ed. 57(31):9916-9920), which form well-defined left-handed 44 helices (FIGS. 1B and 1C). Intriguingly, the side chains of sulfono-γ-AApeptides are aligned perfectly on the top of each other with a pitch of 5.1 Å. Based on the precise three dimensional arrangement of their side functional groups, their close similarity in helical pitch compared to that of α-helix (5.4 Å), as well as the remarkable stability of sulfono-γ-AApeptides, it was envisioned that helical sulfono-γ-AApeptides could be adapted to develop a new class of helical mimetics that disrupt α-helix-mediated protein-protein interactions.

With the aim of developing new PPIs inhibitors for various biological targets, it was envisioned that B-Cell Lymphoma 9 (BCL9) (Zhang M, et al. J. Med. Chem. 61(7):2989-3007; Fan R, et al. (2018) DNA Cell Biol. 37(2):126-132; Teuscher K B, et al. (2017) J. Med. Chem. 60(1):157-169; Wisniewski J A, et al. (2016) ACS Med. Chem. Lett. 7(5):508-513; Zhang M, et al. (2015) Anal. Biochem. 469:43-53; Hoggard L R, et al. (2015) J. Am. Chem. Soc. 137(38):12249-12260; Zhao J-J, et al. (2014) Cancer Res. 74(6):1801-1813; Takada K, et al. (2012) Sci. Transl. Med. 4(148):148ra117-148ra117; Kawamoto S A, et al. (2012). Med. Chem. 55(3):1137-1146: de la Roche M, et al. (2012) Nat. Commun. 3:680; Kawamoto S A, et al. (2009) Biochemistry. 48(40):9534-9541; de la Roche M, et al. (2008) BMC cancer 8:199; Sampietro J, et al. (2006) Mol. Cell 24(2):293-300: Adachi S, et al. (2004) Cancer Res. 64(23):8496-8501; Wang Y, et al. (2010) Science 327(5973):1650-1653), previously shown to engage its α-helical HD2 domain to interact with β-catenin (FIG. 2), could be utilized to develop peptidomimetic helical foldamers based on sulfono-γ-AApeptides. The Wnt/β-catenin signaling pathway plays an important role in embryonic development and tissue homeostasis, and in several types of human cancer such as colorectal cancer, breast cancer, melanoma, prostate cancer, etc (Nusse R & Clevers H (2017) Cell 169(6):985-999; Anastas J N & Moon R T (2012) Nat. Rev. Cancer 13:11-26; Grossmann T N. et al. (2012) Proc. Natl. Acad. Sci. USA 109(44):17942-17947; Dietrich L, et al. (2017) Cell Chem. Biol. 24(8):958-968). As a central mediator of the signaling, β-catenin controls the expression of several key genes that regulate the cell cycle and apoptosis. As the matter of fact, transcriptional activation of Wnt/β-catenin signaling pathway is dependent on the formation of the β-catenin supercomplex involving B-cell lymphoma (BCL9), or BLC9-like (B9L), as well as the T-cell factor (Tcf)/lymphoid enhancer-binding factor (Leo family of transcriptional factors (Sampietro J, et al. (2006) Mol. Cell 24(2):293-300). Specifically, BCL9 functions as a scaffolding structure of the Wnt enhanceosome and brings β-catenin to TCF/LEF to transcribe specific Wnt target genes, leading to cell growth, proliferation and differentiation (van Tienen L M, et al. (2017) eLife 6:e2088). As such, molecules that disrupt BCL9/β-catenin protein-protein interaction could inhibit Wnt/β-catenin signaling transduction, and therefore could be developed as novel anti-cancer agents.

Figures 2A, 2B:
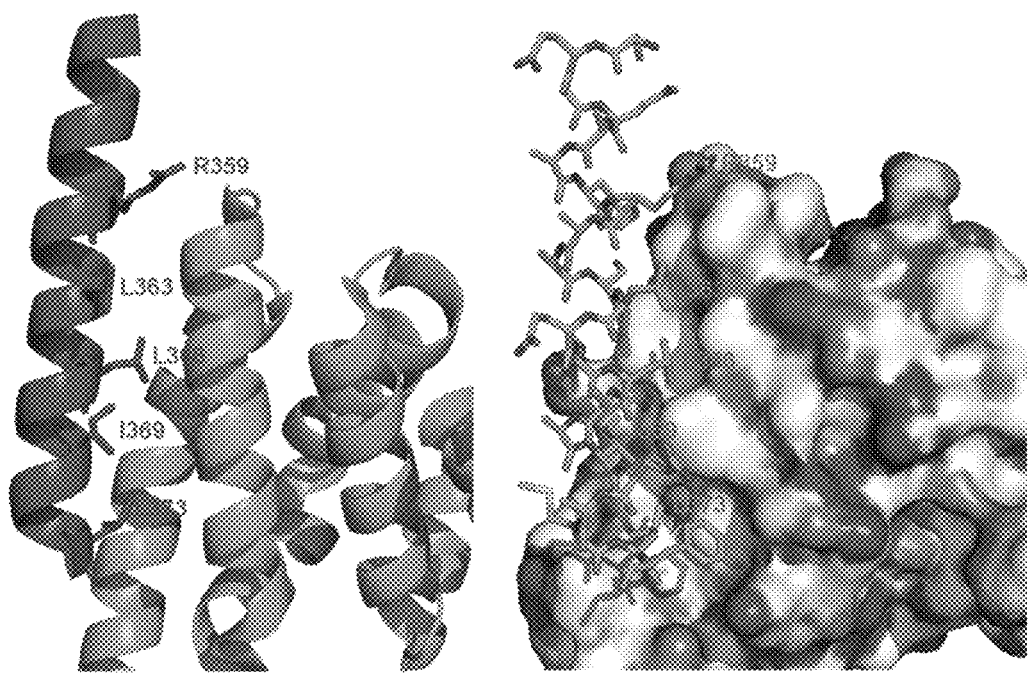
FIG. 2A is a cartoon representation where the residues of BCL9 critical for binding to β-catenin are shown as sticks.
FIG. 2B is a cartoon representation where BCL9 is shown in stick, and β-catenin is represented with the surface model.

The crystal structure of the β-catenin/BCL9/TCF-4 ternary complex (Sampietro J, et al. (2006) Mol. Cell 24(2): 293-300) revealed that the helical domain of BCL9 (351-374) interacts with a binding groove in β-catenin (FIGS. 2A and 2B). The key residues of BCL9, R359, L363, L366, 1369. L373, which are on the one face of BCL9 helix, form both hydrophilic and hydrophobic contacts with the binding surface of β-catenin. Despite unambiguous mechanism of action, the design of potent intracellular inhibitors to block this PPI remains a challenge, mainly attributed to the interaction between BCL9 and β-catenin which is mediated by an approximately 25-residue helical segment from BCL9. While several small-molecule inhibitors have been designed to disrupt β-catenin/BCL9 PPIs, peptide inhibitors are scarce (Zhang M, et al. J. Med. Chem. 61(7):2989-3007; Teuscher K B, et al. (2017) J. Med. Chem. 60(1):157-169; Wisniewski J A, et al. (2016) ACS Med. Chem. Lett. 7(5):508-513; Zhang M, et al. (2015) Anal. Biochem. 469: 43-53; Hoggard L R, et al. (2015) J. Am. Chem. Soc. 137(38):12249-12260; de la Roche M, et al. (2012) Nat. Commun. 3:680-689). Triazole-stapled and olefin-stapled BCL9 L351-F374 α-helical peptides have also been reported (Kawamoto S A, et al. (2012). Med. Chem. 55(3): 1137-1146; Kawamoto S A, et al. (2009) Biochemistry. 48(40):9534-9541; Takada K. et al. (2012) Sci. Transl. Med. 4(148):148ra117-148ra117). While the cell permeability of triazole-stapled peptides was not discussed, the olefin-stapled BCL9 peptide could pass the cell membrane, disrupt the β-catenin/BCL9 PPI, and selectively suppress transcription of Wnt target genes (Takada K, et al. (2012) Sci. Transl. Med. 4(148):148ra117-148ra117). This olefin-stapled peptide also inhibited cancer cell growth, angiogenesis, and metastasis without any evident damage to normal tissues in mouse xenograft models for colorectal carcinoma and multiple myeloma. It is envisioned that unnatural peptidomimetic inhibitors of β-catenin/BCL9 PPI would be appealing because they could mimic peptide helices whereas are highly resistant to proteolytic degradation. However, known peptidic foldamers do not mimic long α-helix efficiently, and there is limited availability of scaffolds and molecular frameworks.

With the availability of helical sulfono-γ-AApeptide scaffold, it was questioned whether sulfono-γ-AApeptides could be designed to effectively disrupt the β-catenin/BCL9 PPI. If so, it would offer a new template to generate potent helical peptidomimetics inhibiting a variety of medicinally relevant PPIs. In view of the folding pattern (FIG. 2C-2F), it was envisioned that sulfono-γ-AApeptides can effectively mimic BCL9 because the side chains of sulfono-γ-AApeptides could be designed to mimic the key residues of the α-helix of BCL9 HD2 domain. Disclosed herein is the development of unnatural peptidomimetics that are highly effective for inhibition of β-catenin/BCL9 PPI.

Results and Discussion

Design of Sulfono-γ-AApeptides and their Biological Activity.

As shown in FIGS. 2C and 2D, the chiral side chains 2a, 4a, 6a, 8a and 10a are on the same face of the helical scaffold of sulfono-γ-AApeptides, and therefore this face was chosen to mimic those critical residues of BCL9 helical domain. The position map of those residues (FIG. 2E) on the α-helical scaffold demonstrates that R359, L363, L366 and L373 are almost on the same line, while 1369 is not. A close comparison of helical scaffolds of the sulfono-γ-AApeptide and the BCL9 peptide reveals that 8b, rather than 8a, could mimic 1369 well (FIG. 2F). As 8b is the sulfonyl side chain, it was hypothesized a methyl sulfonyl group would be sufficient as the sulfonyl group is more sticking out than chiral side chains on helical sulfono-γ-AApeptides.

A panel of sulfono-γ-AApeptides (Table 1) was thus designed and synthesized. The first sulfono-γ-AApeptide sequence designed (2, Table 1) contained only ten sulfono-γ-AA building blocks (comparable to a 20-mer peptide in length), as the crystal structure (FIGS. 2A and 2B) shows the first few residues of BCL9 do not interact with β-catenin directly. The binding affinity of 2 toward β-catenin was next measured using FP assay. The binding affinity of the BCL9 peptide 1 exhibited a $K_d$ of 0.97 μM (Table 1), consistent to previous reports (Shi Y, et al. (2017) J. Med. Chem. 60(22): 9290-9298; Zhang M, et al. (2015) *Anal. Biochem.* 469:43-53). Excitingly, the first sulfono-γ-AApeptide sequence 2, with a shorter length than the BCL9 peptide 1, displayed a $K_d$ of 0.43 μM, which is already two-fold more affinitive to β-catenin than 1. The ability of the sulfono-γ-AApeptide 2 to act as functional mimics of the BCL9 peptide 1 to disrupt BCL9/β-catenin PPI was then examined by AlphaScreen assays (Zhang M, et al. (2015) Anal. Biochem. 469:43-53; Hoggard L R, et al. (2015) J. Am. Chem. Soc. 137(38): 12249-12260). As shown in Table 1, the helical BCL9 peptide 1 could disrupt β-catenin/BCL9 PPI with $K_i$ and $IC_{50}$ values of 1.13 μM and 1.28 μM, respectively, which again are in very good agreement with the literature (Zhang M, et al. J. Med. Chem. 61(7):2989-3007; Teuscher K B, et al. (2017) J. Med. Chem. 60(1):157-169; Wisniewski J A, et al. (2016) ACS Med. Chem. Lett. 7(5):508-513; Zhang M, et al. (2015) Anal. Biochem. 469:43-53; Hoggard L R, et al. (2015) J. Am. Chem. Soc. 137(38):12249-12260). The sulfono-γ-AApeptide 2 was found to disrupt β-catenin/BCL9 with $K_i$ and $IC_{50}$ values of 0.64 μM and 0.74 μM, respectively, which are almost two-fold more potent than 1. This initial success demonstrated the potential of sulfono-γ-AApeptides for the mimicry of long α-helix, as well as their robust helical folding propensity (She F, et al. (2018) Angew. Chem. Int. Ed. 57(31):9916-9920). To investigate the importance of the side chains in the sulfono-γ-AApeptide sequence, alanine scanning studies were carried out based on sulfono-γ-AApeptide sequence 2 (Tables 1A and 1B, sequences 3-8). Each key residue was replaced with Ala side chain at positions 1b, 2a, 6a, 8a and 10a (marked with "*"). It appears that aminoethane (position 1b), Arg (position 2a) and Leu (position 10a) play an important role in inhibition of β-catenin/BCL9 PPI, as about 1.5-fold decrease relative to 2 in binding affinity was caused by each Ala substitution (Table 1, sequences 3, 4 and 7). The result of sulfono-γ-AApeptide sequence 3 indicates that positively charged side chains could affect binding activity even if they were not involved in direct contact with β-catenin/BCL9 binding pocket. It appears that Leu (position 6a) is the most critical group for inhibiting β-catenin/BCL9 PPI (Table 1, sequence 5), as the Ala substitution resulted in a decrease in binding affinity with $K_d$, $K_i$ and $IC_{50}$ values of 1.97 μM, 2.43 μM and 2.71 μM, respectively. Interestingly, mutation of Ile (position 8a) to Ala in 6 further improved the binding affinity and inhibitory activity with $K_d$, $K_i$ and $IC_{50}$ values of 0.16 μM (~6 fold), 0.46 μM (~3 fold) and 0.54 μM (~3 fold) compared to the peptide 1, respectively (Tables 1A and 1B). It was hypothesized that although the critical residue for interaction is the side chain 8b, the less bulkier methyl group at 8b is expected to have less impact of steric hindrance than Ile side chain on the neighboring 8b, which may ensure the closer interaction of the sequence with β-catenin. Indeed, a bulkier group at 8b led to decreased binding activity (sequence 10). It seems that strong hydrophobic interaction near C-terminal region is critical, as change of the groups at positions of 7b, 8a and 9a to less hydrophobic groups or cationic groups lead to sequences 8, 9, 11 which show inferior binding activity. The importance of these key side chains was further manifested by sulfono-γ-AApeptide sequence 12 (Tables 1A and 1B). It lacks several key side chains at positions 1b, 2a, 6a and 10a, completely losing their ability to inhibit β-catenin/BCL9 PPI. It should be noted that the binding affinity $K_d$ from fluorescence anisotropy studies is highly consistent with the $K_i$ and $IC_{50}$ obtained from AlphaScreen assays that measure the direct competition of all tested sequences for the interaction of BCL9 peptide with β-catenin, suggesting these sequences bind to the same site on β-catenin.

TABLE 1A

Structures of sulfono-γ-AApeptides investigated for the disruption β-catenin/BCL9 interaction. The critical side chains are shown in bold.

| Peptide | Sequence |
|---|---|
| 1 | Ac-SQEQLEHRERSLQTLRDIQRMLF-NH₂ (SEQ ID NO: 1) |
| 2 | |
| 3 | |
| 4 | |

TABLE 1A-continued
Structures of sulfono-γ-AApeptides investigated for the disruption β-catenin/BCL9 interaction. The critical side chains are shown in bold.
| Peptide | Sequence |
|---|---|
| 5 | 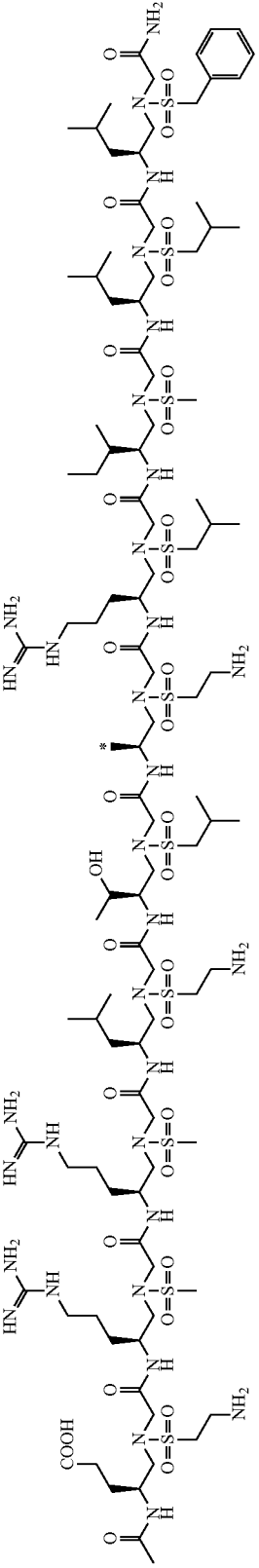 |
| 6 | 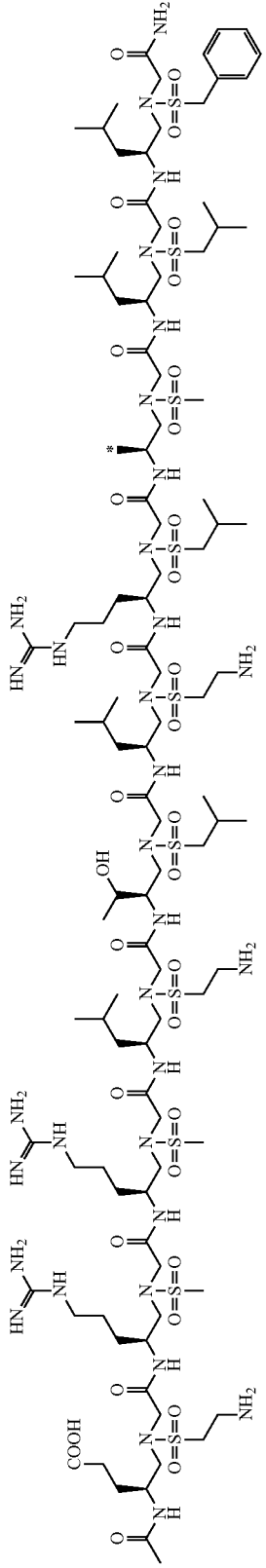 |
| 7 | 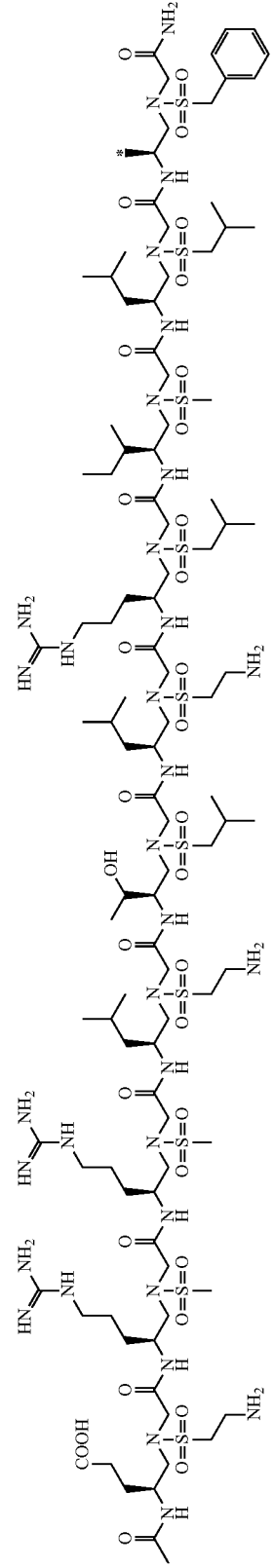 |

TABLE 1A-continued

Structures of sulfono-γ-AApeptides investigated for the disruption β-catenin/BCL9 interaction. The critical side chains are shown in bold.

| Peptide | Sequence |
|---|---|
| 8 | |
| 9 | |
| 10 | |

TABLE 1A-continued
Structures of sulfono-γ-AApeptides investigated for the disruption β-catenin/BCL9 interaction. The critical side chains are shown in bold.
| Peptide | Sequence |
|---|---|
| 11 | 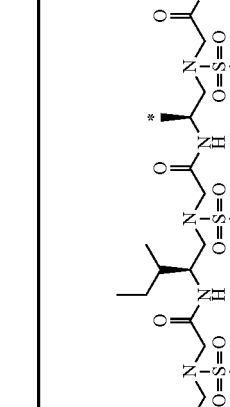 |
| 12 | 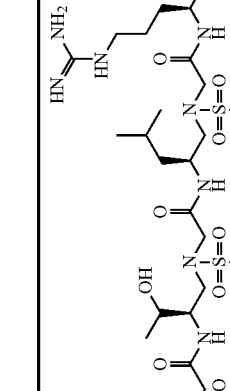 |

TABLE 1B

Activity of peptides for the disruption
of β-catenin and BCL9 interaction

| Peptide | $K_d$ (μM) | $IC_{50}$ (μM) | $K_i$ (μM) |
| --- | --- | --- | --- |
| 1 | 0.97 | 1.28 ± 0.29 | 1.13 ± 0.24 |
| 2 | 0.43 | 0.74 ± 0.15 | 0.64 ± 0.11 |
| 3 | 0.86 | 1.04 ± 0.21 | 0.92 ± 0.17 |
| 4 | 0.82 | 1.10 ± 0.14 | 0.98 ± 0.11 |
| 5 | 1.97 | 2.71 ± 0.37 | 2.43 ± 0.32 |
| 6 | 0.16 | 0.54 ± 0.13 | 0.46 ± 0.10 |
| 7 | 0.70 | 1.00 ± 0.10 | 0.89 ± 0.08 |
| 8 | 3.89 | 8.01 ± 0.82 | 7.20 ± 0.72 |
| 9 | 5.14 | 12.9 ± 2.15 | 11.6 ± 1.92 |
| 10 | 2.51 | 4.07 ± 0.59 | 3.65 ± 0.51 |
| 11 | 8.26 | 17.4 ± 3.35 | 15.7 ± 3.00 |
| 12 | >10 | >10 | >10 |

Figure 3C:
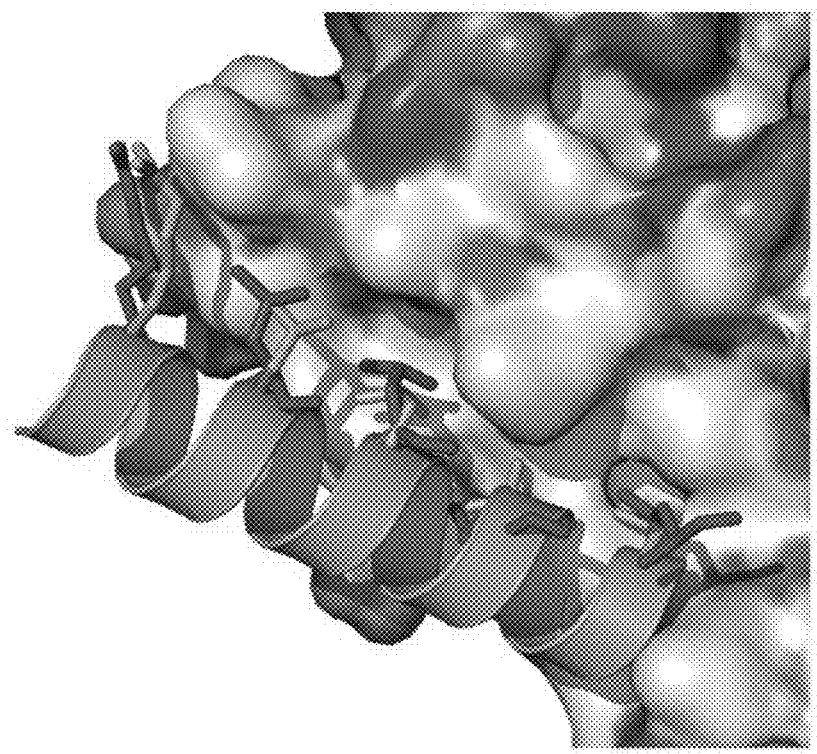
FIG. 3C is an overlay of peptide 6 with critical residues of BCL9 on the binding surface of β-catenin (PDB: 2GL7) using the PyMOL software.
Figure 3B:
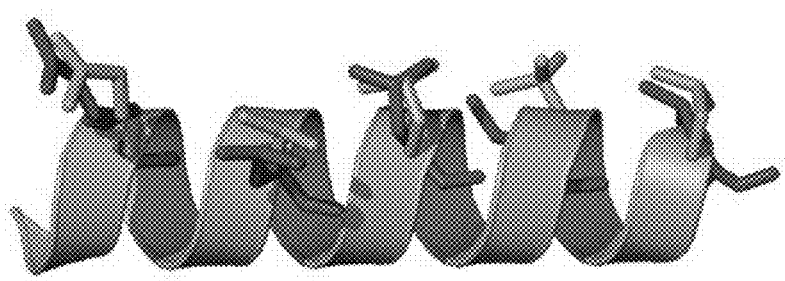
FIG. 3B is an overlay of peptide 6 with critical residues of the BCL9 helical peptide using the PyMOL software.
Figure 3A:
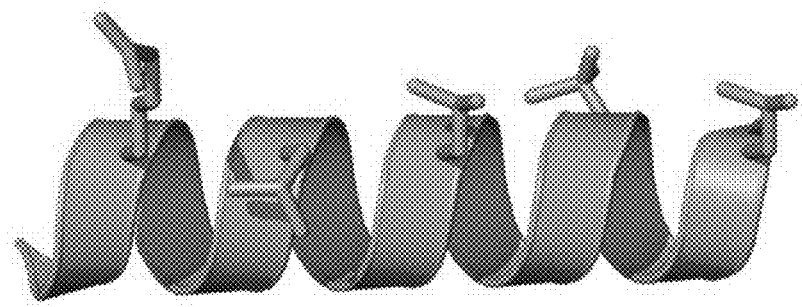
FIG. 3A is a proposed structure of peptide 6 with critical side chains 2a, 4a, 6a, 8b, 10a shown in stick presentation.

The excellent binding activity of sulfono-γ-AApeptides was further rationalized by the modeling studies. The structure of 6 was built on the scaffold of the crystal structure (She F, et al. (2018) Angew. Chem. Int. Ed. 57(31):9916-9920), and then superimpose with the BCL9 helical domain by overlaying the helical backbone orientations using the PyMOL software (FIG. 3A) (Schrödinger L. (2015) The PyMOL Molecular Graphics System. Version 2.1.1.). As shown in FIGS. 3B and 3C, the side chains of critical residues of the BCL9 peptide overlap very well with the side chains of 2a, 4a, 6a, 8b, 10a of sulfono-γ-AApeptide 6. As a result, the helical sulfono-γ-AApeptide 6 could bind to the groove of β-catenin tightly through both hydrophilic and hydrophobic interactions using these side chains.

Circular Dichroism Measurements.

Figure 4:
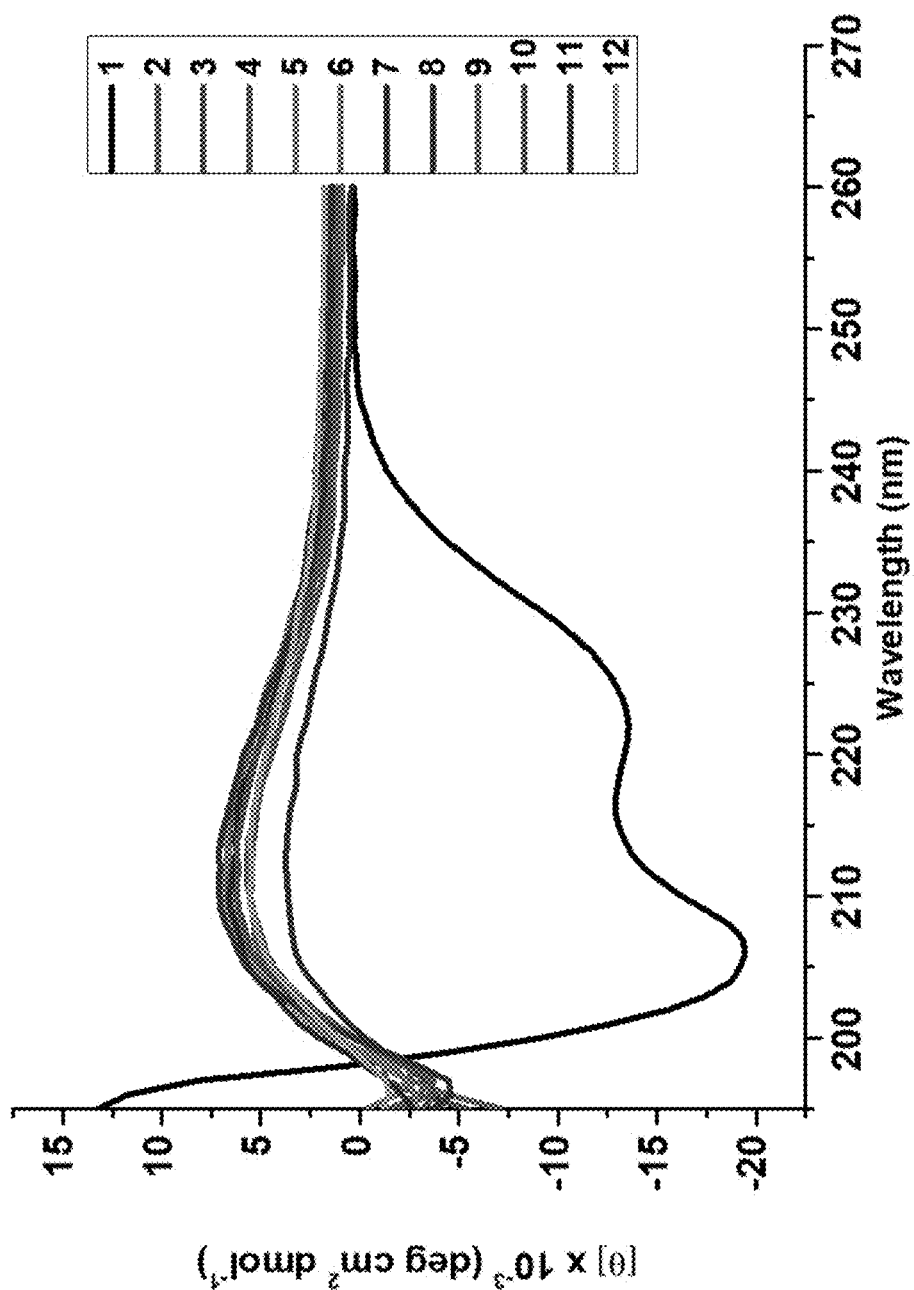
FIG. 4 is a circular dichroism spectra of BCL9 peptide 1 and sulfono-γ-AApeptides 2-12 (100 μM) measured at room temperature in PBS buffer.

It was hypothesized that sulfono-γ-AApeptides should adopt well defined helices in solution as they generally possess better activity than the natural BCL9 peptide 1, which is the natural binding partner of β-catenin. Circular dichroism (CD) spectroscopic studies were next conducted to investigate the helicity of regular peptide 1 and homogeneous sulfono-γ-AApeptides 2-12. CD studies were performed in PBS buffer between 190 nm and 260 nm. As shown in FIG. 4, each sulfono-γ-AApeptide revealed a marked cotton effect with the strong positive maximum around 210 nm, which is consistent with the previously reported CD spectra of helical sulfono-γ-AApeptides (She F, et al. (2018) Angew. Chem. Int. Ed. 57(31):9916-9920), suggesting that sequences 2-12 adopt a similar left-handed helical conformation. As anticipated, the peptide 1 with the length of 23 residues, also adopted helical conformation in solution.

Cell Permeability Test.

Figure 5:
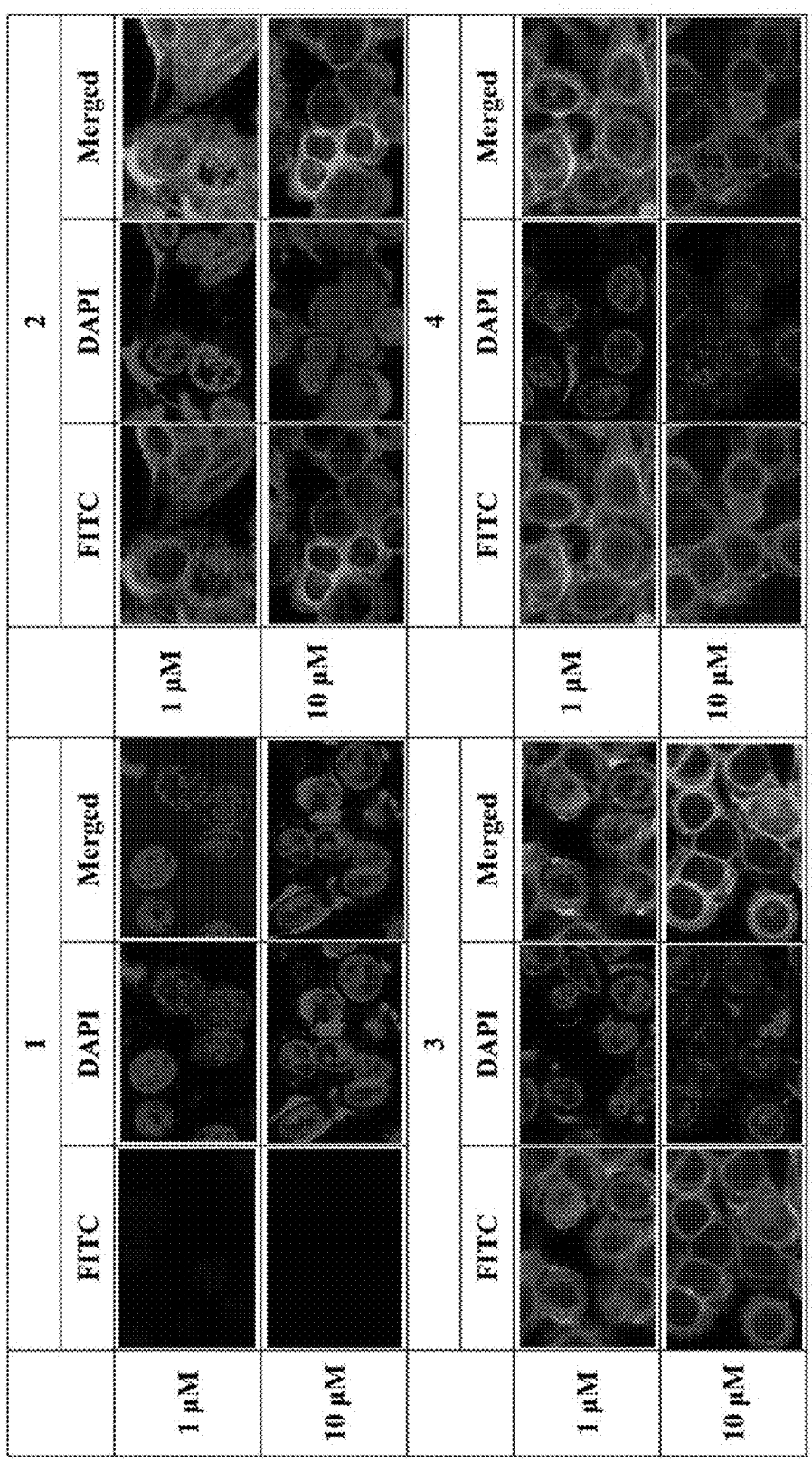
FIG. 5 contains Confocal fluorescence microscopy images of SW480 cells treated with 1 μM and 10 μM of the FITC-labeled peptide 1 and sulfono-γ-AApeptides 2-4 for 2 h.

The inhibition of intracellular PPIs remains challenging in chemical biology and drug discovery (Wilson A J (2009) Chem. Soc. Rev. 38(12):3289-3300; Nero T L, et al. (2014) Nat. Rev. Cancer 14:248-262; Arkin Michelle R, et al. (2014) Chem. Biol. 21(9):1102-1114). As an intracellular PPI inhibitor, it has to penetrate and cross the cell membrane. This may also be the reason why it is challenging to develop peptidomimetic-based inhibitors for β-catenin/BCL9 PPI as the sequences are considerably long. To determine whether the newly developed sulfono-γ-AApeptide inhibitors could permeate Wnt/β-catenin-dependent cancer cells, the cellular uptake of FITC-labeled derivatives of the sulfono-γ-AApeptides 2-4 and the BCL9 peptide 1 was next examined in SW480 cells by confocal fluorescence microscopy (FIG. 5). When SW480 cells were treated with FITC-labeled peptide 1, negligible green fluorescence was observed at 1 and 10 μM for 2 h, consistent with the observation that peptide 1 possesses poor cell permeability and exhibits no cellular activity (Hoggard L R, et al. (2015) J. Am. Chem. Soc. 137(38):12249-12260). However, it is surprising that when SW480 cells were treated with FITC-labeled sulfono-γ-AApeptides 2-4 at the same concentrations for 2 h (FIG. 5), strong and evenly diffused intracellular green fluorescence was noticed in cytoplasm, even at the concentration as low as 1 μM. The results suggest that sulfono-γ-AApeptides are highly cell permeable, possibly due to the existence of multi-sulfonamide groups on the molecular scaffold. As such, although the BCL9 peptide 1 was known for its cell impermeability as well as poor cellular activity toward Wnt/β-catenin-dependent cancer cells, it was hypothesized that the sulfono-γ-AApeptides could cross membranes and gain access to targets within the cytoplasm of living cells.

MTS Cell Viability Assay.

MTS tetrazolium cell viability assays were then performed to assess the effect of β-catenin/BCL9 inhibitors on the cell proliferation of colorectal cancer cells (SW480), which have hyperactive Wnt/β-catenin signaling (Table 2). Consistent to previous reports, the regular BCL9 peptide 1 showed very poor activity with an $IC_{50}$ of >200 μM. Intriguingly, the MTS assay of 2-7 showed that sulfono-γ-AApeptides inhibited cancer cell proliferation in dose-dependent manners. Compounds 2-4 exhibited excellent inhibitory activity with $IC_{50}$s of ~12 μM toward SW480 cells (Table 2). It is noted that these sequences are more selective toward SW480 cells than A549 cells (>3 fold) that have normal β-catenin signaling, suggesting the good specificity of the tested sulfono-γ-AApeptides. Interestingly, sequence 6, which is most active in vitro, displayed relatively weak activity, possibly due to some unknown side interactions. This initial encouraging result prompted us to further study their effects on Wnt/β-catenin signaling by TOPFlash and FOPFlash luciferase reporter assays (Zhang M, et al. J. Med. Chem. 61(7):2989-3007; Wisniewski J A, et al. (2016) ACS Med. Chem. Lett. 7(5):508-513; Hoggard L R, et al. (2015) J. Am. Chem. Soc. 137(38):12249-12260).

TABLE 2

MTS assay to monitor the inhibitory
activities of sulfono-γ-AApeptides
on the viability of cancer cells.
MTS $IC_{50}$ ± SD (μM)

| compound | hyperactive β-catenin signaling SW480 cell | Normal β-catenin signaling A549 cell |
| --- | --- | --- |
| 1 | >200 | >200 |
| 2 | 12.5 ± 2.86 | 39.9 ± 4.75 |
| 3 | 12.8 ± 2.90 | 43.7 ± 3.62 |
| 4 | 16.4 ± 4.40 | 43.2 ± 5.60 |
| 5 | 132 ± 18.9 | 230 ± 27.5 |
| 6 | 65.4 ± 7.06 | 150 ± 19.2 |
| 7 | 46.6 ± 5.57 | 120 ± 13.6 |

TOPFlash/FOPFlash Luciferase Reporter Assays.

Figure 6A:
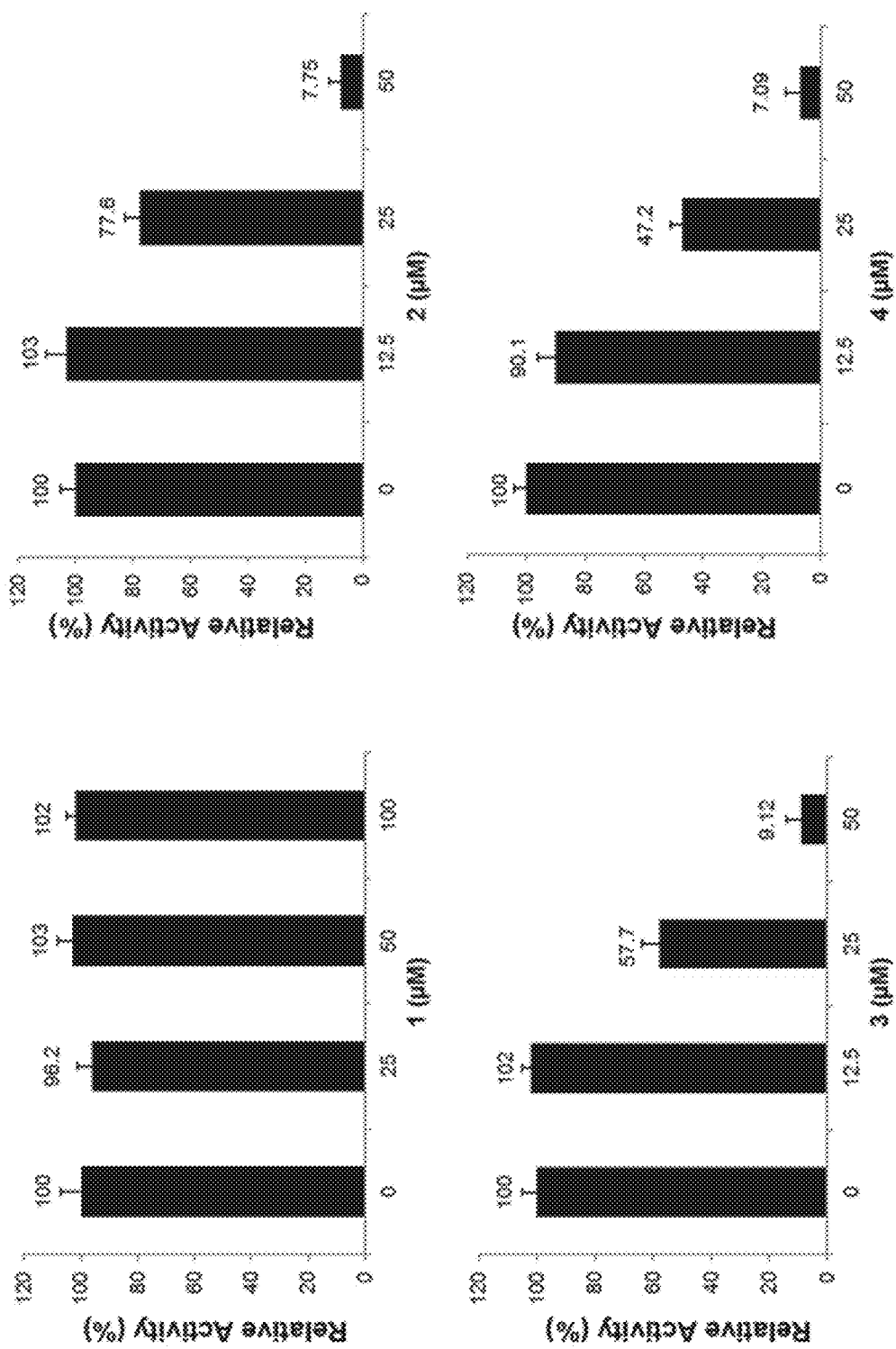
FIG. 6A contains bar graphs showing Wnt-responsive TOPFlash luciferase reporter assay results of inhibitors 1-4 in β-catenin activated SW480 cells.
Figure 6B:
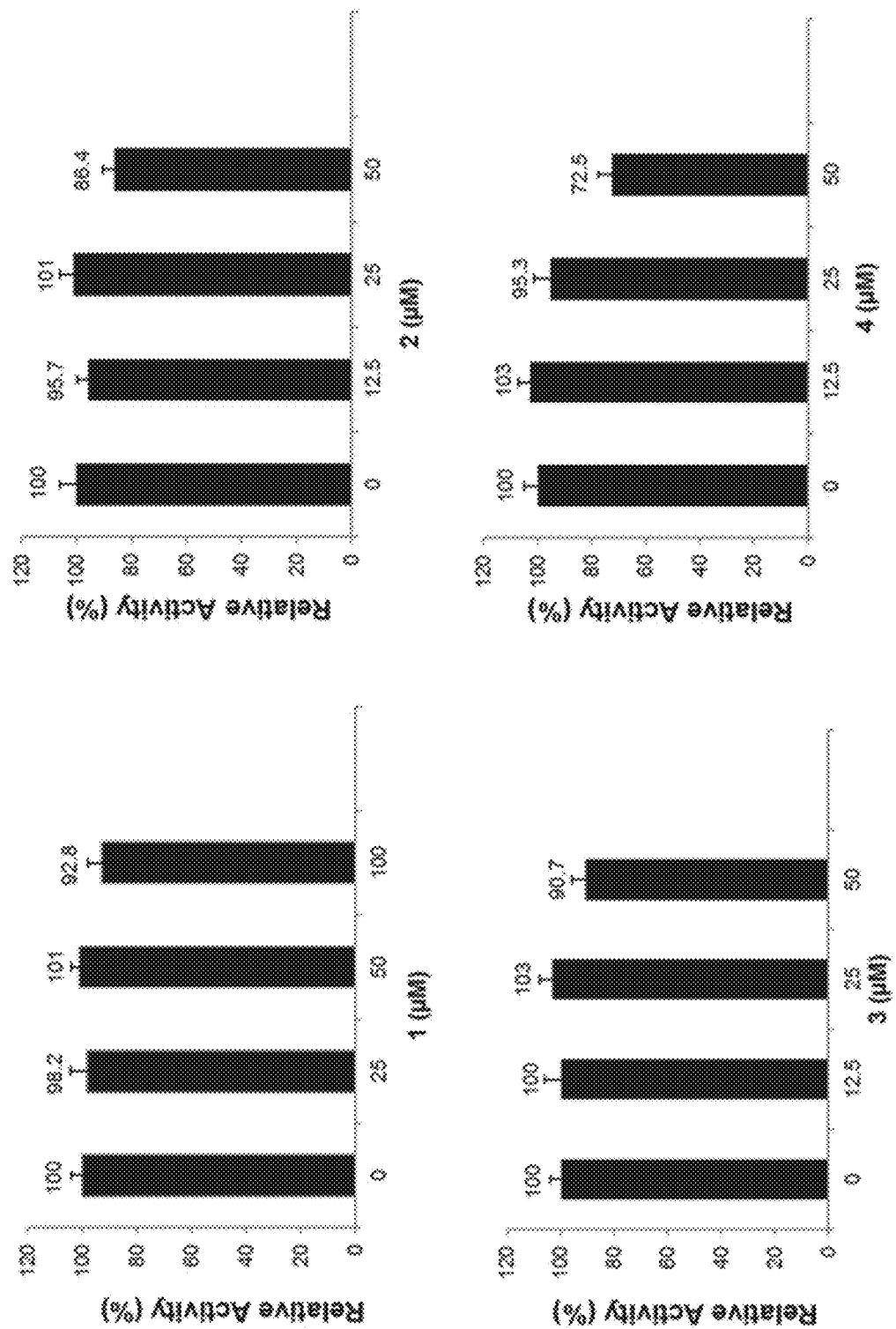
FIG. 6B contains bar graphs showing Wnt-responsive FOPFlash luciferase reporter assay results of inhibitors 1-4 in β-catenin activated SW480 cells.

Wnt-specific TOPFlash/FOPFlash luciferase reporter assays were used to evaluate the effects of these compounds on β-catenin-dependent transcription. For the TOPFlash reporter construct, the firefly luciferase reporter gene was placed downstream of three wild-type Tcf binding sites. For the FOPFlash reporter construct, the firefly luciferase reporter gene was place downstream of three mutant Tcf binding sites. The high expression of firefly luciferase in TOPFlash assays was controlled by tandem Tcf binding sites. The renilla luciferase reporter construct (pCMV-RL) was used as the internal control to normalize luciferase reporter signals and eliminate systematic errors such as cell viability, transfection effect, etc. The TOPFlash luciferase reporter assay was performed on the most potent sulfono-γ-AApeptides 2-4. Consistent to cell proliferation studies, the sulfono-γ-AApeptide inhibitors 2-4 suppressed the TOPFlash luciferase activities (FIG. 6A) in SW480 in a dose-dependent manner, with $IC_{50}$s estimated at 35.4, 26.5, and 20.6 µM, respectively (FIG. 13). At 50 µM, each compound inhibited more than 90% of luciferase activity. As expected, the regular BCL9 peptide 1 did not show any activity. Interestingly, in the follow-up FOPFlash luciferase reporter assay, the inhibitory activity of 2-4 dropped significantly (FIG. 6B). At the concentration of 50 µM, luciferase retain >85% of its activity. The renilla internal control values were constant in all TOFlash/FOPFlash assays (Table S2). Taken together, these results suggested that the three sulfono-γ-AApeptide inhibitors 2-4 selectively inhibit Wnt/β-catenin signaling transactivation while do not have general inhibition of the other transcriptional pathways.

Cellular Target Engagement.

Figure 7A:
FIG. 7A shows levels of β-catenin associated with 3-Bioton and 4-Biotin in SW480 cell lysate. Input: 5% of cell lysate.

Two experiments were conducted to examine whether these sulfono-γ-AApeptides can engage β-catenin in the cellular context. Biotinylated 3 (3-Biotin) and biotinylated 4 (4-Biotin) (the best two compounds in Luciferase Reporter Assays) were synthesized and incubated with SW480 cell lysates. The proteins that bind with these two sequences were then pulled down by streptavidin-conjugated beads and examined by Western blot analyses using β-catenin-specific antibody. As shown in FIG. 7A, both 3-Biotin and 4-Biotin can effectively bind with β-catenin in SW480 cell lysates at the concentration of 1 µM.

Figure 7B:
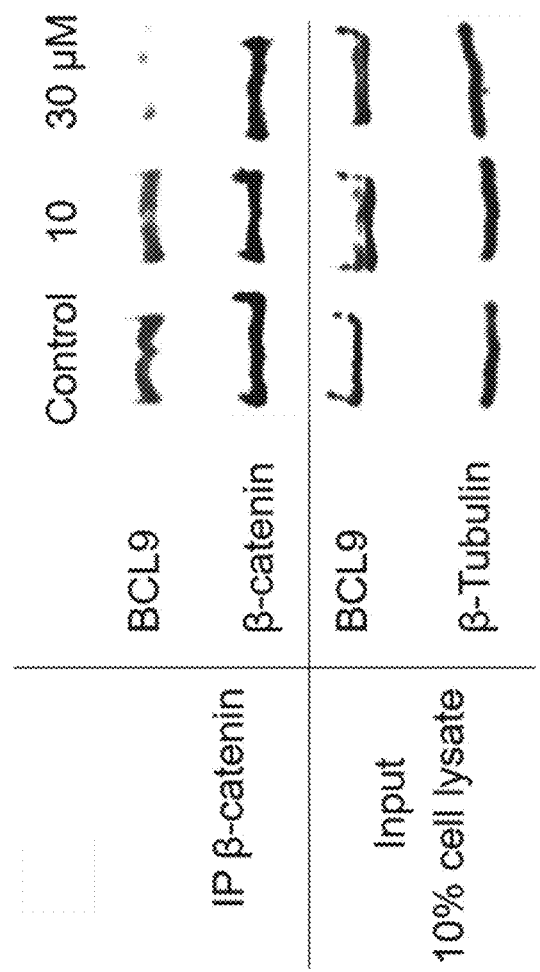
FIG. 7B shows co-IP experiments to evaluate the disruption of the β-catenin/BCL9 PPI by 4 in Wnt/β-catenin hyperactive cancer cells. IP, immunoprecipitation: IB, immunoblotting; input, 10% of the cell lysate. Each experiment was performed in duplicate.

Co-immunoprecipitation (co-IP) experiments were also performed with Wnt/β-catenin hyperactive HCT116 cancer cells to evaluate the effects of 4 on disruption of the β-catenin/BCL9 PPI in cells. As shown in FIG. 7B, inhibitor 4 disrupted the β-catenin/BCL9 PPI in a dose-dependent manner, while the input and immunoprecipitation controls were constant between different experiments.

Enzymatic Stability Study.

Figure 19:
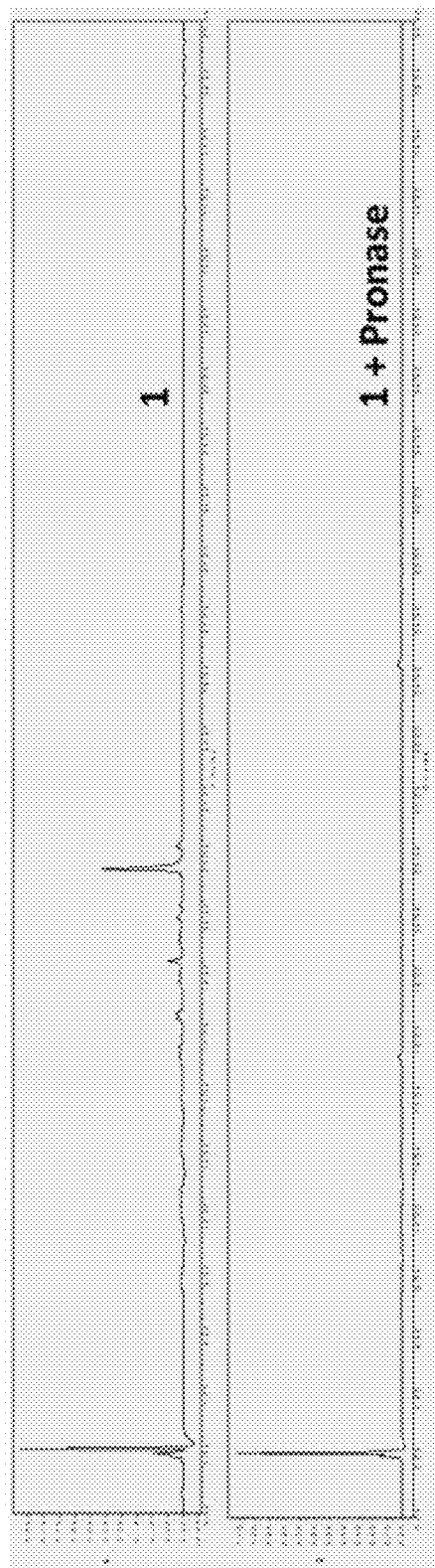
FIG. 19 shows analytic HPLC trace of 1 before and after incubation with Pronase (0.1 mg/mL) in 100 mM pH 7.8 ammonium bicarbonate buffer at 37° C.

In addition to cell permeability, the protease stability of the sequences is critical for their biological activity. The proteolytic stability of helical sulfono-γ-AApeptides 2-4 and the BCL9 peptide 1 was next evaluated in pronase, a mixture of broad scope endo- and exopeptidases isolated from *Streptomyces griseus* (Hook D F, et al. (2005) Chem. Biodiversity 2(5):591-632). The assays were conducted by incubating 0.1 mg/mL of three lead compounds 2-4 and the regular peptide 1 with 0.1 mg/mL pronase in 100 mM ammonium bicarbonate buffer (pH 7.8) at 37° C. for 24 h. The stability of the examined compounds was analyzed by HPLC-MS (FIGS. 19-22). The control peptide 1 was completely degraded by pronase with no intact peptide remaining (FIG. 19). It may explain why the peptide 1 showed weak cell permeability and completely abandoned its cellular activity. Strikingly, the linear sulfono-γ-AApeptides showed no detectable degradation (FIGS. 20-22), demonstrating extraordinarily high stability against enzymatic degradation, augmenting their potential in therapeutic applications.

In summary, disclosed herein is a series of helical sulfono-γ-AApeptides that mimic α-helix and disrupt protein-protein interactions. These unnatural helical peptidomimetics are able to disrupt cancer-related β-catenin/BCL9 protein-protein interaction with excellent potency and specificity. The cell-based studies indicated that sulfono-γ-AApeptides are cell permeable and can effectively inhibit growth of cancer cells that have hyperactive Wnt/β-catenin signaling. The TOPFlash/FOPFlash luciferase reporter assays demonstrated that sulfono-γ-AApeptides can selectively suppress transactivation of Wnt/β-catenin signaling. The protein pull-down and co-IP experiments demonstrated that these sulfono-γ-AApeptides can bind with β-catenin and disrupt β-catenin/BCL9 PPI in cells. Also disclosed herein is the successful application of unnatural peptidomimetics in disrupting β-catenin/BCL9 PPI, which has been long considered as the challenging target, providing a practical method for the development of novel foldameric peptidomimetics that serve as proteolytically stable and cell-penetrating inhibitors for a myriad of PPIs.

Methods

Sulfono-γ-AApeptide Building Block Preparation

Fmoc-protected amino acids and Fluorescein isothiocyanate (FITC) were purchased from Chem-impex (Wood Dale, IL). D-biotin was purchased from Sigma-Aldrich, Inc. Rink Amide-MBHA resin (0.646 mmol/g) was purchased from GL Biochem (Shanghai) Ltd. 1-Hydroxybenzotriazole wetted with no less than 20% wt. water (HOBt), 1-Ethyl-3-(3-dimethylaminopropyl) carbodiimide (EDC) and N, N-Diisopropylethylamine (DIPEA) were purchased from Oakwood Chemical (Estill, SC). Thin layer chromatography was performed on Sorbtech TLC plates (silica gel w/UV254), visualizing with UV-light 254 nm. Flash column chromatography was performed with ICN silica gel (60 Å, 230-400 mesh, 32-63 µm). $^1$H NMR spectra were recorded at 400 MHz using TMS as internal standard. $^{13}$C NMR spectra were recorded at 100 MHz using TMS as internal standard. The multiplicities are reported as follows: singlet (s), doublet (d), doublet of doublets (dd), triplet (t), quartet (q), multiplet (m). Coupling constants are reported in Hertz (Hz). High resolution mass spectra were obtained on an Agilent 6220 using electrospray ionization time-of-flight (ESI-TOF). Other chemicals and all solvents were purchased from Sigma-Aldrich (St. Louis, MO) or Fisher and used without further purification.

Synthetic Routes

The sulfono-γ-AApeptide building blocks BB1-14 were synthesized based on previously report and Fmoc-protected amino acids were used as the initial starting materials.1 BB1-7 were synthesized based on route 1, BB8-10 were synthesized based on route 2, BB11-14 were synthesized based on route 3 (Scheme 1).

Scheme 1. General synthetic route to prepare sulfono-γ-AApeptide building blocks.

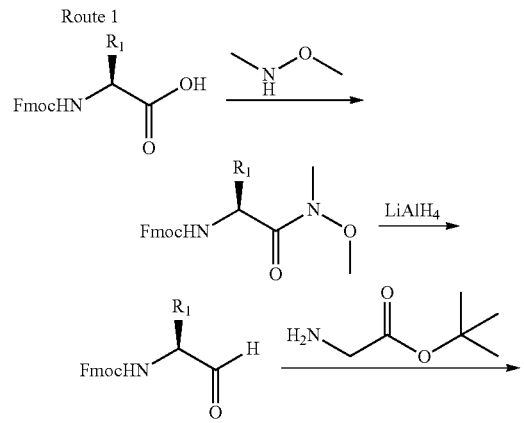

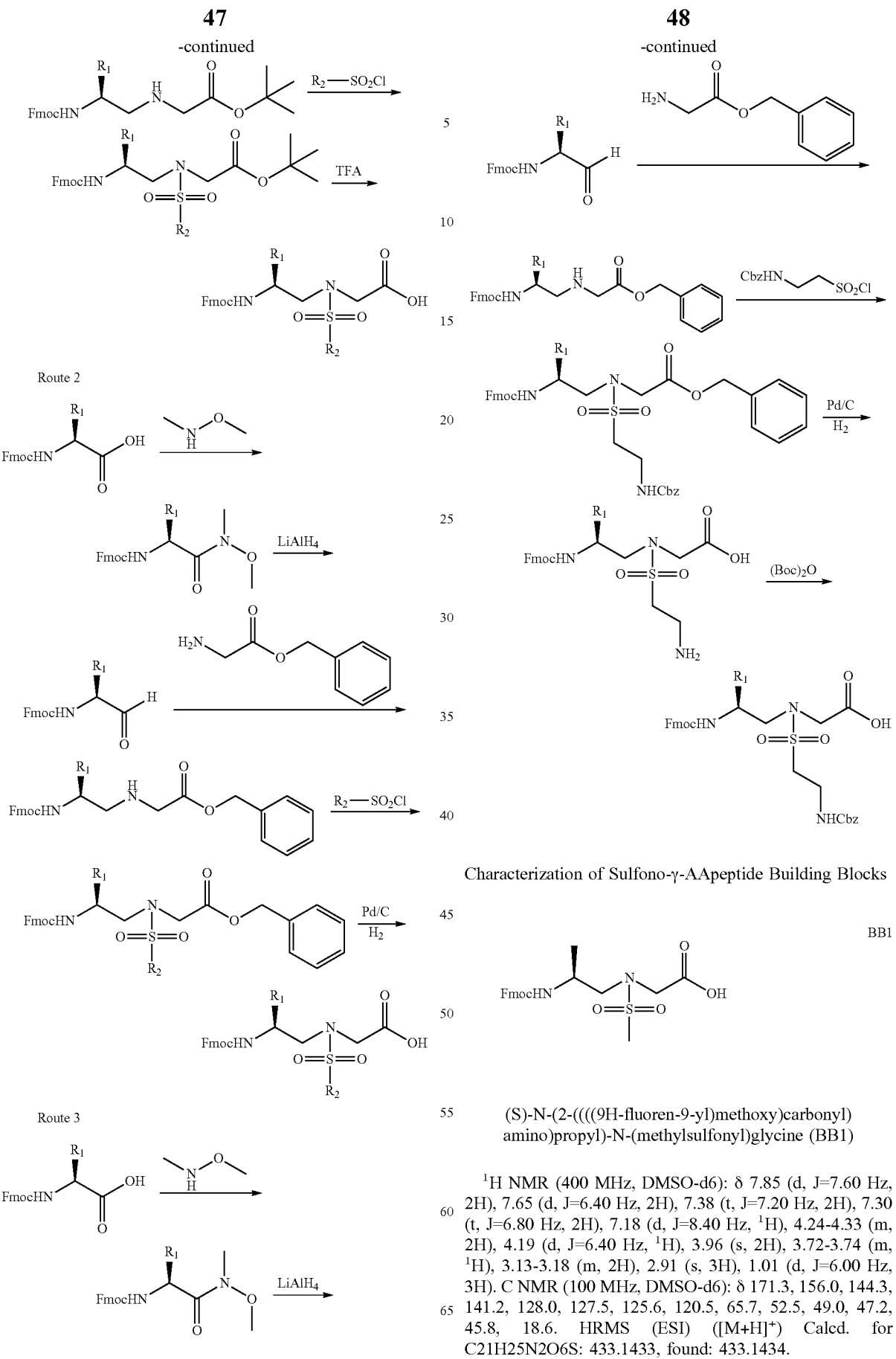
Characterization of Sulfono-γ-AApeptide Building Blocks
(S)-N-(2-((((9H-fluoren-9-yl)methoxy)carbonyl)amino)propyl)-N-(methylsulfonyl)glycine (BB1)
$^1$H NMR (400 MHz, DMSO-d6): δ 7.85 (d, J=7.60 Hz, 2H), 7.65 (d, J=6.40 Hz, 2H), 7.38 (t, J=7.20 Hz, 2H), 7.30 (t, J=6.80 Hz, 2H), 7.18 (d, J=8.40 Hz, $^1$H), 4.24-4.33 (m, 2H), 4.19 (d, J=6.40 Hz, $^1$H), 3.96 (s, 2H), 3.72-3.74 (m, $^1$H), 3.13-3.18 (m, 2H), 2.91 (s, 3H), 1.01 (d, J=6.00 Hz, 3H). C NMR (100 MHz, DMSO-d6): δ 171.3, 156.0, 144.3, 141.2, 128.0, 127.5, 125.6, 120.5, 65.7, 52.5, 49.0, 47.2, 45.8, 18.6. HRMS (ESI) ([M+H]$^+$) Calcd. for $C_{21}H_{25}N_2O_6S$: 433.1433, found: 433.1434.

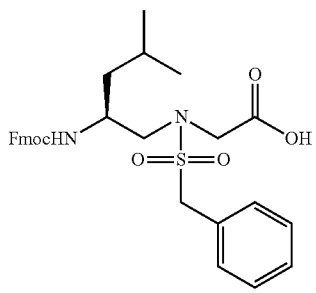

BB2

(S)-N-(2-((((9H-fluoren-9-yl)methoxy)carbonyl)amino)-4-methylpentyl)-N-(benzylsulfonyl)glycine (BB2)

$^1$H NMR (400 MHz, DMSO-d6): δ 7.83 (d, J=7.60 Hz, 2H), 7.64 (d, J=7.20 Hz, 2H), 7.36-7.38 (m, 3H), 7.34 (s, 1H), 7.31 (t, J=4.00 Hz, 3H), 7.25 (t, J=7.20 Hz, 2H), 7.17 (d, J=9.20 Hz, 1H), 4.41 (t, J=13.60 Hz, 2H), 4.34 (q, J=6.40, 3.60 Hz, 1H), 4.28 (q, J=10.40, 6.80 Hz, 1H), 4.17 (t, J=6.40 Hz, 1H), 3.91 (q, J=28.00, 18.80 Hz, 2H), 3.66-3.71 (m, 1H), 3.24 (dd, J=14.80, 5.60 Hz, 1H), 3.07 (q, J=14.40, 8.80 Hz, 1H), 1.46-1.55 (m, 1H), 1.18-1.28 (m, 2H), 0.81 (q, J=10.00, 6.00 Hz, 6H). $^{13}$C NMR (100 MHz, DMSO-d6): δ 171.2, 156.4, 144.3, 144.2, 141.2, 131.3, 130.1, 128.7, 128.5, 128.0, 127.4, 125.6, 120.5, 65.6, 57.8, 52.7, 49.3, 48.2, 47.3, 41.3, 24.6, 23.7, 22.0. HRMS (ESI) ([M+H]$^+$) Calcd. for C$_{30}$H$_{35}$N$_2$O$_6$S: 551.2216, found: 551.2211.

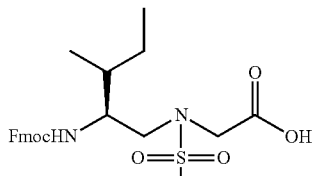

BB3

N-((2S,3R)-2-((((9H-fluoren-9-yl)methoxy)carbonyl)amino)-3-methylpentyl)-N-(methylsulfonyl)glycine (BB3)

$^1$H NMR (400 MHz, DMSO-d6): δ 7.84 (d, J=7.20 Hz, 2H), 7.67 (d, J=7.60 Hz, 2H), 7.37 (t, J=7.60 Hz, 2H), 7.26-7.31 (m, 2H), 7.17 (d, J=9.60 Hz, 1H), 4.31 (d, J=7.20 Hz, 2H), 4.19 (t, J=6.40 Hz, 1H), 3.97 (q, J=21.20, 19.20 Hz, 2H), 3.56-3.61 (m, 1H), 3.42 (dd, J=14.40, 2.80 Hz, 1H), 3.09 (q, J=14.40, 10.40 Hz, 1H), 2.91 (s, 3H), 1.31-1.40 (m, 2H), 0.99-1.08 (m, 1H), 0.80 (t, J=6.80 Hz, 6H). $^{13}$C NMR (100 MHz, DMSO-d6): δ 171.3, 156.5, 144.3, 141.2, 128.0, 127.4, 125.6, 120.5, 65.6, 54.4, 48.9, 48.7, 47.3, 37.6, 25.1, 15.6, 11.8. HRMS (ESI) ([M+H]$^+$) Calcd. for C$_{24}$H$_{31}$N$_2$O$_6$S: 475.1903, found: 475.1912.

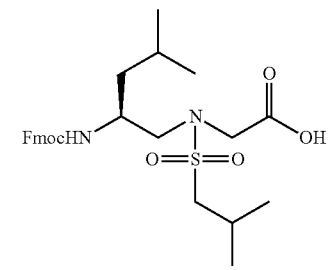

BB4

(S)-N-(2-((((9H-fluoren-9-yl)methoxy)carbonyl)amino)-4-methylpentyl)-N-(isobutylsulfonyl)glycine (BB4)

$^1$H NMR (400 MHz, DMSO-d6): δ 7.85 (d, J=7.20 Hz, 2H), 7.66 (t, J=3.20 Hz, 2H), 7.38 (t, J=6.80 Hz, 2H), 7.27-7.31 (m, 2H), 7.13 (d, J=8.80 Hz, 1H), 4.33 (q, J=10.00, 7.20 Hz, 1H), 4.26 (t, J=6.80 Hz, 1H), 4.16 (t, J=6.40 Hz, 1H), 3.94 (s, 2H), 3.68-3.69 (m, 1H), 3.22-3.26 (m, 1H), 3.09 (q, J=14.00, 8.80 Hz, 1H), 2.88-2.99 (m, 2H), 2.02-2.08 (m, 1H), 1.52 (brs, 1H), 1.18-1.25 (m, 2H), 0.93-0.95 (m, 6H), 0.81 (dd, J=12.00, 6.40 Hz, 6H). $^{13}$C NMR (100 MHz, DMSO-d6): δ 171.2, 156.3, 144.3, 144.2, 141.2, 128.0, 127.4, 125.6, 120.5, 65.6, 59.4, 51.9, 48.6, 48.1, 47.3, 41.3, 24.7, 23.7, 22.6, 22.0. HRMS (ESI) ([M+H]$^+$) Calcd. for C$_{27}$H$_{37}$N$_2$O$_6$S: 517.2372, found: 517.2370.

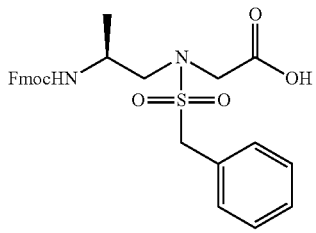

BB5

(S)-N-(2-((((9H-fluoren-9-yl)methoxy)carbonyl)amino)propyl)-N-(benzylsulfonyl)glycine (BB5)

$^1$H NMR (400 MHz, DMSO-d6): δ 7.84 (d, J=7.60 Hz, 2H), 7.64 (d, J=7.20 Hz, 2H), 7.31-7.38 (m, 7H), 7.25 (q, J=15.20, 7.60 Hz, 3H), 4.41 (q, J=22.80, 9.60 Hz, 2H), 4.28 (d, J=6.80 Hz, 2H), 4.17 (t, J=6.40 Hz, 1H), 3.90 (q, J=32.00, 18.40 Hz, 1H), 3.72 (q, J=13.20, 6.40 Hz, 1H), 3.10-3.24 (m, 2H), 1.02 (d, J=6.40 Hz, 3H). $^{13}$C NMR (100 MHz, DMSO-d6): δ 171.3, 156.1, 144.3, 141.1, 131.3, 130.1, 128.7, 128.6, 128.0, 127.5, 125.6, 120.5, 65.8, 57.7, 53.2, 49.5, 47.2, 45.9, 32.0, 18.7. HRMS (ESI) ([M+H]$^+$) Calcd. for C$_{27}$H$_{29}$N$_2$O$_6$S: 509.1746, found: 509.1740.

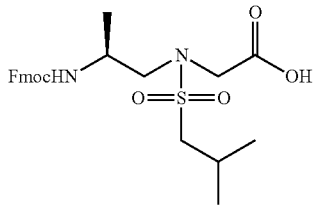

BB6

(S)-N-(2-((((9H-fluoren-9-yl)methoxy)carbonyl)amino)propyl)-N-(isobutylsulfonyl)glycine (BB6)

$^1$H NMR (400 MHz, DMSO-d6): δ 7.81 (d, J=7.60 Hz, 2H), 7.62 (d, J=6.40 Hz, 2H), 7.34 (t, J=7.20 Hz, 2H), 7.26 (t, J=7.20 Hz, 2H), 7.16 (d, J=9.60 Hz, 1H), 4.22 (d, J=6.40 Hz, 2H), 4.14 (d, J=6.40 Hz, 1H), 3.92 (s, 2H), 3.68 (t, J=6.40 Hz, 1H), 3.11-3.16 (m, 2H), 2.91 (t, J=6.00 Hz, 2H), 1.97-2.07 (m, 1H), 0.97 (d, J=6.40 Hz, 3H), 0.92 (d, J=1.60 Hz, 3H), 0.90 (s, 3H). $^{13}$C NMR (100 MHz, DMSO-d6): δ 171.2, 156.0, 144.2, 141.1, 128.0, 127.4, 125.6, 120.5, 65.7, 59.3, 52.4, 48.7, 47.1, 45.7, 24.6, 22.5, 18.7. HRMS (ESI) ([M+H]$^+$) Calcd. for $C_{24}H_{31}N_2O_6S$: 475.1903, found: 475.1908.

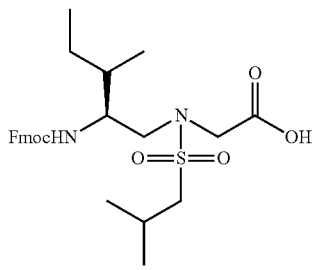

BB7

N-((2S,3S)-2-((((9H-fluoren-9-yl)methoxy)carbonyl)amino)-3-methylpentyl)-N-(isobutylsulfonyl)glycine (BB7)

$^1$H NMR (400 MHz, DMSO-d6): δ 7.84 (d, J=7.20 Hz, 2H), 7.67 (d, J=7.20 Hz, 2H), 7.37 (t, J=7.20 Hz, 2H), 7.26-7.30 (m, 2H), 7.19 (d, J=9.60 Hz, 1H), 4.31 (q, J=10.00, 7.20 Hz, 1H), 4.24 (t, J=6.80 Hz, 1H), 4.18 (t, J=6.80 Hz, 1H), 3.95 (q, J=28.40, 18.40 Hz, 2H), 3.54-3.59 (m, 1H), 3.43 (dd, J=14.80, 2.80 Hz, 1H), 3.10 (q, J=14.40, 10.40 Hz, 1H), 2.98 (q, J=14.00, 6.40 Hz, 1H), 2.88 (q, J=14.00, 6.80 Hz, 1H), 1.99-2.09 (m, 1H), 1.28-1.40 (m, 2H), 0.99-1.09 (m, 1H), 0.92 (d, J=6.40 Hz, 6H), 0.75-0.81 (m, 5H), 0.62-0.70 (m, 1H). $^{13}$C NMR (100 MHz, DMSO-d6): δ 171.3, 156.5, 144.3, 144.2, 141.2, 128.0, 127.4, 125.6, 120.5, 65.7, 59.7, 54.3, 48.6, 47.3, 37.6, 25.1, 24.7, 22.6, 22.5, 15.6, 11.8. HRMS (ESI) ([M+H]$^+$) Calcd. for $C_{27}H_{37}N_2O_6S$: 517.2372, found: 517.2380.

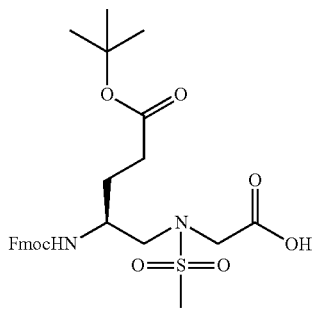

BB8

(S)-N-(2-((((9H-fluoren-9-yl)methoxy)carbonyl)amino)-5-(tert-butoxy)-5-oxopentyl)-N-(methylsulfonyl)glycine (BB8)

$^1$H NMR (400 MHz, DMSO-d6): δ 7.87 (d, J=7.60 Hz, 2H), 7.68 (d, J=6.80 Hz, 2H), 7.40 (t, J=6.80 Hz, 2H), 7.32 (t, J=7.20 Hz, 2H), 7.17 (d, J=8.80 Hz, 1H), 4.33 (d, J=6.80 Hz, 2H), 4.22 (d, J=6.40 Hz, 1H), 3.97 (s, 2H), 3.67 (brs, 1H), 3.27-3.30 (m, 1H), 3.14 (q, J=14.40, 8.40 Hz, 1H), 2.93 (s, 3H), 2.18-2.20 (m, 2H), 1.74 (s, 1H), 1.38 (s, 1H), 1.38 (brs, 10H). $^{13}$C NMR (100 MHz, DMSO-d6): δ 172.3, 171.2, 156.4, 144.3, 141.2, 128.1, 127.5, 125.6, 120.6, 80.0, 65.7, 51.3, 49.4, 48.7, 47.3, 31.8, 28.2, 27.6. HRMS (ESI) ([M+H]+) Calcd. for $C_{27}H_{35}N_2O_8S$: 547.2114, found: 547.2119.

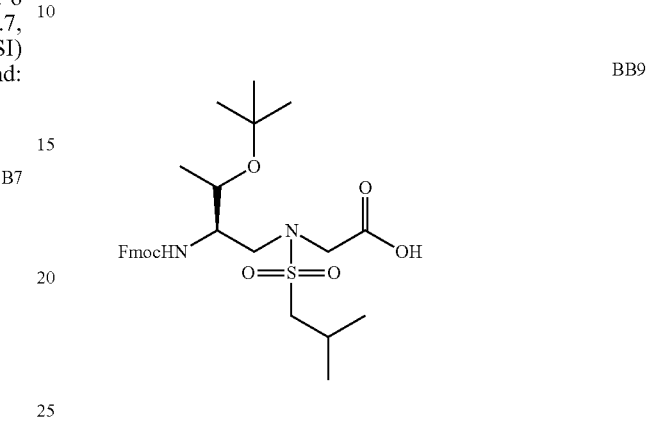

BB9

N-((2R,3S)-2-((((9H-fluoren-9-yl)methoxy)carbonyl)amino)-3-(tertbutoxy)butyl)-N-(isobutylsulfonyl)glycine (BB9)

$^1$H NMR (400 MHz, DMSO-d6): δ 7.84 (d, J=7.20 Hz, 2H), 7.67 (d, J=7.20 Hz, 2H), 7.37 (t, J=7.20 Hz, 2H), 7.27-7.31 (m, 2H), 7.19 (d, J=9.20 Hz, 1H), 4.26-4.35 (m, 2H), 4.19 (t, J=6.80 Hz, 1H), 4.04 (d, J=18.80 Hz, 1H), 3.89 (d, J=18.40 Hz, 1H), 3.65-3.68 (m, 1H), 3.51-3.57 (m, 2H), 3.18 (q, J=14.80, 10.80 Hz, 1H), 2.89-3.01 (m, 2H), 2.01-2.11 (m, 1H), 1.09 (s, 9H), 0.94 (d, J=6.80 Hz, 6H), 0.90 (d, J=6.00 Hz, 3H). $^{13}$C NMR (100 MHz, DMSO-d6): δ 171.3, 156.4, 144.3, 144.1, 141.2, 128.0, 127.4, 125.7, 125.6, 120.5, 73.8, 67.2, 65.7, 59.9, 55.1, 48.8, 47.3, 46.7, 28.4, 24.7, 22.6, 22.6, 17.7. HRMS (ESI) ([M+H]$^+$) Calcd. for $C_{29}H_{41}N_2O_7S$: 561.2634, found: 561.2634.

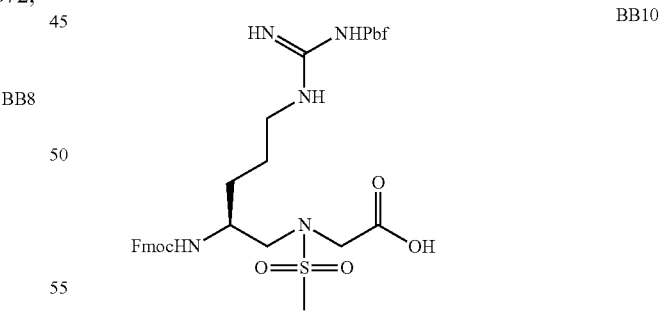

BB10

(S)-N-(2-((((9H-fluoren-9-yl)methoxy)carbonyl)amino)-5-(3-((2,2,4,6,7-pentamethyl-2,3-dihydrobenzofuran-5-yl)sulfonyl)guanidino)pentyl)-N-(methylsulfonyl)glycine (BB10).

$^1$H NMR (400 MHz, DMSO-d6): δ 7.83 (d, J=7.20 Hz, 2H), 7.64 (d, J=7.20 Hz, 2H), 7.36 (t, J=7.20 Hz, 2H), 7.26-7.30 (m, 2H), 7.13 (d, J=9.20 Hz, 1H), 6.39-6.68 (m, 2H), 4.26-4.34 (m, 3H), 4.18 (t, J=6.40 Hz, 1H), 3.95 (s, 2H), 3.61 (brs, 1H), 3.23 (dd, J=14.40, 4.80 Hz, 1H), 3.10 (q, J=14.40, 8.80 Hz, 1H), 2.94-3.00 (m, 2H), 2.89 (s, 5H), 2.47 (s, 3H), 2.40 (s, 3H), 1.97 (s, 3H), 1.38 (d, J=4.00 Hz, 1H), 1.34 (s, 6H), 1.18-1.29 (m, 2H). $^{13}$C NMR (100 MHz, DMSOd6): δ 171.2, 157.9, 156.4, 144.3, 141.2, 137.8, 134.5, 131.9, 128.0, 127.5, 125.6, 124.8, 120.5, 116.7, 86.7, 65.6, 51.5, 49.9, 48.8, 47.2, 42.9, 29.6, 28.7, 19.4, 18.0, 12.7. HRMS (ESI) ([M+H]$^+$) Calcd. for $C_{37}H_{48}N_5O_9S_2$: 770.2893, found: 770.2899.

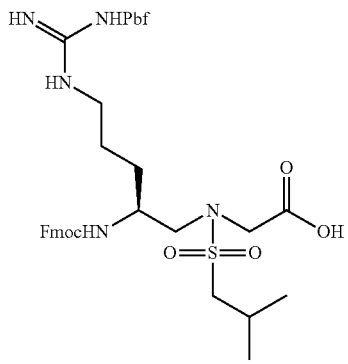

BB11

(S)-N-(2-(((((9H-fluoren-9-yl)methoxy)carbonyl)amino)-5-(3-((2,2,4,6,7-pentamethyl-2,3-dihydrobenzofuran-5-yl)sulfonyl)guanidino)pentyl)-N-(isobutylsulfonyl)glycine (BB11). $^1$H NMR (400 MHz, DMSO-d6): δ 7.82 (d, J=7.60 Hz, 2H), 7.65 (q, J=7.20, 3.60 Hz, 2H), 7.36 (t, J=7.20 Hz, 2H), 7.26-7.30 (m, 2H), 7.16 (d, J=9.20 Hz, $^1$H), 6.41-6.67 (m, 2H), 4.25-4.33 (m, 2H), 4.18 (t, J=6.80 Hz, $^1$H), 3.97 (t, J=19.60 Hz, 2H), 3.62 (brs, $^1$H), 3.27 (dd, J=14.40, 4.40 Hz, $^1$H), 3.14 (q, J=14.40, 8.80 Hz, $^1$H), 2.97-3.01 (m, 2H), 2.93 (q, J=9.60, 2.80 Hz, 2H), 2.88 (s, 2H), 2.48 (s, 3H), 2.41 (s, 3H), 2.02-2.10 (m, $^1$H), 1.97 (s, 3H), 1.39-1.41 (m, 2H), 1.34 (s, 6H), 1.23-1.29 (m, 2H), 0.94 (q, J=6.40, 3.20 Hz, 6H), 0.77-0.80 (m, $^1$H). $^{13}$C NMR (100 MHz, DMSO-d6): δ 171.3, 156.4, 144.3, 144.2, 141.2, 137.9, 132.0, 128.0, 127.4, 125.6, 124.8, 120.5, 117.0, 116.8, 86.7, 65.7, 59.5, 51.4, 49.9, 48.6, 47.3, 42.9, 29.7, 28.6, 24.7, 22.6, 19.4, 18.0, 12.6. HRMS (ESI) ([M+H]+) Calcd. for $C_{40}H_{54}N_5O_9S_2$: 812.3363, found: 812.3360.

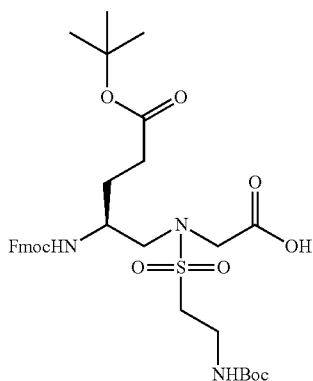

BB12

(S)-N-(2-(((((9H-fluoren-9-yl)methoxy)carbonyl)amino)-5-(tert-butoxy)-5-oxopentyl)-N-((2-((tert-butoxycarbonyl)amino)ethyl)sulfonyl)glycine (BB12). $^1$H NMR (400 MHz, DMSO-d6): δ 7.84 (d, J=7.60 Hz, 2H), 7.65 (t, J=6.80 Hz, 2H), 7.37 (t, J=7.20 Hz, 2H), 7.29 (t, J=7.20 Hz, 2H), 7.16 (d, J=9.20 Hz, $^1$H), 6.84 (d, J=5.20 Hz, $^1$H), 4.29 (d, J=6.80 Hz, 2H), 4.18 (t, J=6.80 Hz, $^1$H), 3.98 (s, 2H), 3.63 (brs, $^1$H), 3.28 (q, J=12.80, 5.60 Hz, 3H), 3.21 (q, J=10.00, 5.60 Hz, 2H), 3.14 (q, J=14.40, 8.40 Hz, $^1$H), 2.09-2.22 (m, 2H), 1.71-1.73 (m, $^1$H), 1.44-1.50 (m, $^1$H), 1.35 (s, 9H), 1.32 (s, 9H). $^{13}$C NMR (100 MHz, DMSO-d6): δ 172.3, 171.1, 156.4, 155.7, 144.3, 144.2, 141.2, 128.0, 127.4, 125.6, 120.5, 80.0, 78.5, 65.7, 51.7, 51.2, 49.3, 47.2, 35.2, 31.8, 28.6, 28.1, 27.5. HRMS (ESI) ([M+H]$^+$) Calcd. for $C_{33}H_{46}N_3O_{10}S$: 676.2904, found: 676.2901.

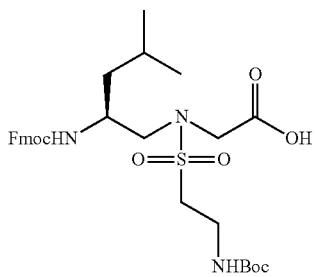

BB13

(S)-N-(2-(((((9H-fluoren-9-yl)methoxy)carbonyl)amino)-4-methylpentyl)-N-((2-((tert-butoxycarbonyl)amino)ethyl)sulfonyl)glycine (BB13). $^1$H NMR (400 MHz, DMSO-d6): δ 7.78 (d, J=7.20 Hz, 2H), 7.60 (t, J=6.00 Hz, 2H), 7.32 (t, J=7.20 Hz, 2H), 7.21-7.26 (m, 2H), 7.08 (d, J=9.20 Hz, $^1$H), 6.80 (brs, $^1$H), 4.25 (d, J=5.60 Hz, 2H), 4.12 (t, J=6.80 Hz, $^1$H), 3.93 (s, 2H), 3.64-3.65 (m, $^1$H), 3.23 (t, J=5.60 Hz, 2H), 3.16 (t, J=4.00 Hz, 2H), 3.05 (q, J=14.00, 8.40 Hz, $^1$H), 1.99 (s, $^1$H), 1.43-1.48 (m, $^1$H), 1.27 (s, 9H), 1.11-1.23 (m, 2H), 0.76 (q, J=12.40, 6.80 Hz, 6H), 0.66 (dd, J=22.40, 4.80 Hz, $^1$H). $^{13}$C NMR (100 MHz, DMSO-d6): δ 171.1, 156.2, 155.7, 144.3, 144.1, 141.1, 127.9, 127.4, 125.5, 120.4, 78.4, 65.5, 51.8, 51.6, 48.7, 48.1, 47.2, 41.2, 35.1, 31.0, 28.5, 24.6, 23.6, 21.9. HRMS (ESI) ([M+H]$^+$) Calcd. for $C_{30}H_{42}N_3O_8S$: 604.2693, found: 604.2689.

BB14

(S)-N-(2-(((((9H-fluoren-9-yl)methoxy)carbonyl)amino)propyl)-N-((2-(tertbutoxycarbonyl)amino)ethyl)sulfonyl)glycine (BB14)

$^1$H NMR (400 MHz, DMSOd6): δ 7.84 (d, J=7.60 Hz, 2H), 7.65 (t, J=5.20 Hz, 2H), 7.37 (t, J=7.20 Hz, 2H), 7.29 (t, J=7.20 Hz, 2H), 7.19 (d, J=8.40 Hz, $^1$H), 6.86 (brs, $^1$H), 4.24-4.31 (m, 2H), 4.16-4.21 (m, $^1$H), 3.98 (s, 2H), 3.70-3.73 (m, $^1$H), 3.28 (t, J=6.00 Hz, 2H), 3.20 (t, J=8.00 Hz, 3H), 2.02 (s, $^1$H), 1.32 (s, 9H), 1.02 (d, J=6.40 Hz, 3H). $^{13}$C NMR (100 MHz, DMSO-d6): δ 171.2, 156.0, 155.7, 144.3, 144.3, 141.1, 128.0, 127.5, 125.5, 120.5, 78.5, 65.7, 52.4, 51.5, 48.8, 47.2, 45.8, 35.2, 28.6, 18.6. HRMS (ESI) ([M+H]$^+$) Calcd. for $C_7H_{36}N_3O_8S$: 562.2223, found: 562.2217.

Preparation of BCL9 Peptides and Sulfono-γ-AApeptides

Solid-phase synthesis of the peptides were conducted in the peptide synthesis vessels on a Burrell Wrist-Action shaker. All peptides were analyzed and purified on a Waters Breeze 2 HPLC system installed with both analytic module (1 mL/min) and preparative module (16 mL/min), by employing a method using 5-100% linear gradient of solvent B (0.1% TFA in acetonitrile) in solvent A (0.1% TFA in water) over 35 min, followed by 100% solvent B over 15 min. The pure products were then collected and lyophilized on a Labcono lyophilizer, and the purity of the compounds was determined to be >95% by analytical HPLC. Masses of γ-AApeptides were obtained on an Agilent 6220 using electrospray ionization time-of-flight (ESI-TOF).

General Synthetic Route afterwards washed DCM (×3) and DMF (×3). A premixed solution of the sulfono-γ-AApeptide Building Block (2 equiv.), HOBt (4 equiv.), and DIC (4 equiv.) in 2 mL DMF was added to the resin and shaken for 4 h to complete the coupling reaction. After wash with DCM and DMF, the resin was treated with 20% piperidine/DMF solution for 15 min (×2). Another Fmoc protected regular amino acid/sulfono-γ-AApeptide building block (2 equiv.) was attached on the resin following the procedure in the first coupling step, and Fmoc protecting group was removed after the coupling reaction was done. The reaction cycles were repeated until the desired sulfono-γ-AApeptides were synthesized. For the capped sequence, the N-terminus of the sequence was capped with acetic anhydride (1 mL) in pyridine (2 mL) (15

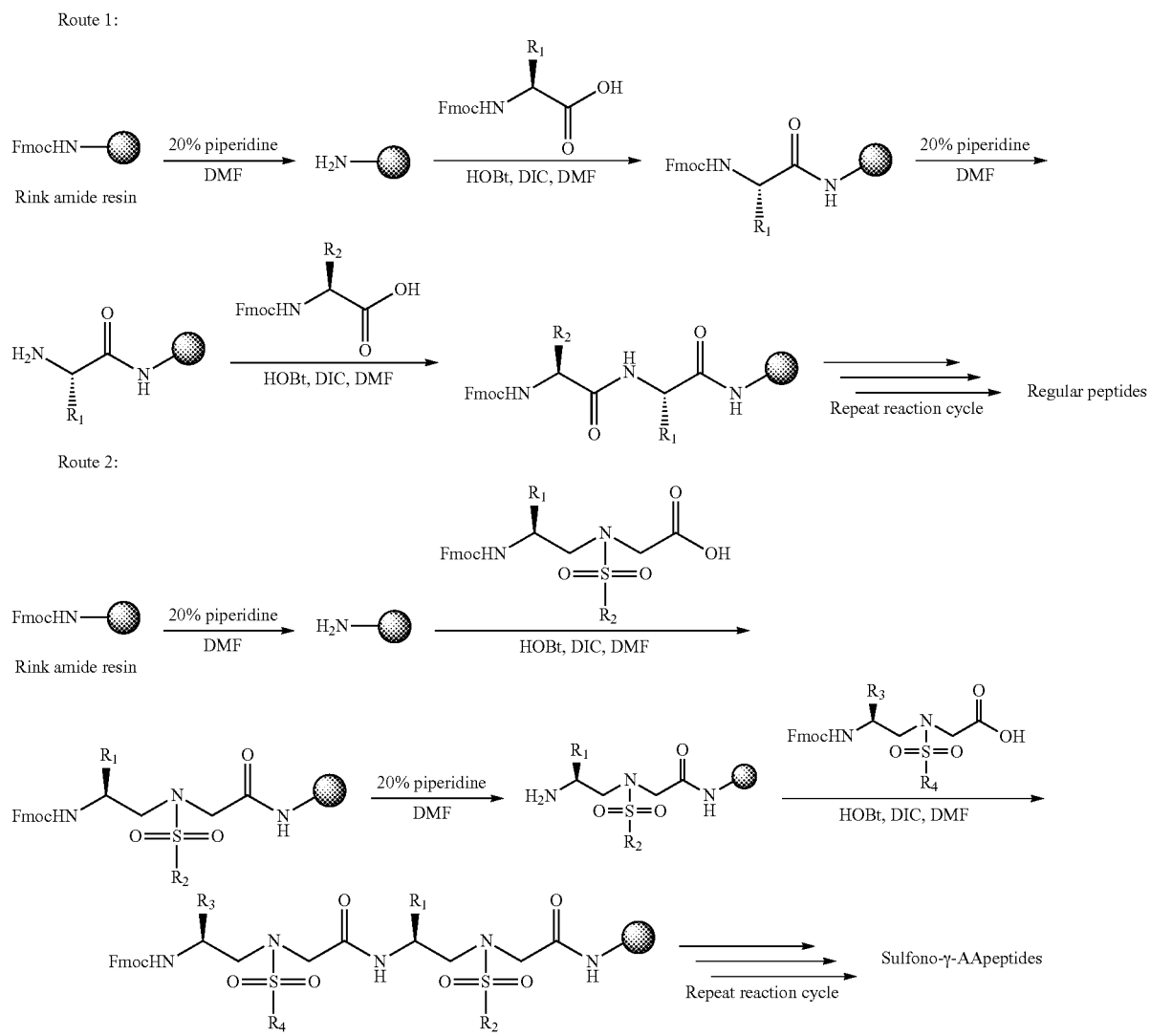

Scheme 2. General synthetic route to prepare regular peptides and sulfono-γ-AApeptides.

The regular peptides were prepared based on route 1, the sulfono-γ-AApeptides were prepared based on route 2. The synthesis was carried out on 100 mg Rink Amide-MBHA resin (0.646 mmol/g) under room temperature at atmosphere. The resin was swelled in DMF for 5 min before use, followed by treatment with 20% piperidine/DMF solution (2 mL) for 15 min (×2) to remove Fmoc protecting group, min×2), followed by treatment with TFA/DCM (6 mL, 1:1, v/v) for 3 h. The cleavage solution was collected, and the beads were washed with DCM (3 mL×2). The solution was combined and evaporated under air flow to give the crude product, which was analyzed and purified by Water HPLC system, at the 1 mL/min and 16 mL/min flow rate for analytic and preparative HPLC, respectively. The gradient eluting method of 5% to 100% of solvent B (0.1% TFA in acetonitrile) in A (0.1% TFA in water) over 50 min was performed. All the sulfono-γ-AApeptides were obtained with decent yield (39.39-46.72%) with a purity >95% after prep-HPLC purification.

For the FITC-labeled sulfono-γ-AApeptides synthesis, after installation of the last sulfono-γ-AApeptide building block, the Fmoc protecting group was then removed, afterwards washed with DCM (×3) and with DMF (×3). A premixed solution of Fmoc-β-Ala-OH (2 equiv.), HOBt (4 equiv.), and DIC (4 equiv.) in 2 mL DMF was added to the resin and shaken for 2 h to complete the coupling reaction. The Fmoc protecting group was then removed, FITC (2 equiv.) in 2 mL DMF and DIPEA (6 equiv.) was added to the resin and shaken for overnight to complete the reaction. After wash with DMF (×3) and DCM (×3), the resin was cleaved using TFA/DCM (6 mL, 1:1, v/v) for 3 h. The pure FITC-labeled sulfono-γ-AApeptides (>95%) were obtained using the same abovementioned method by HPLC.

Figure 8A:
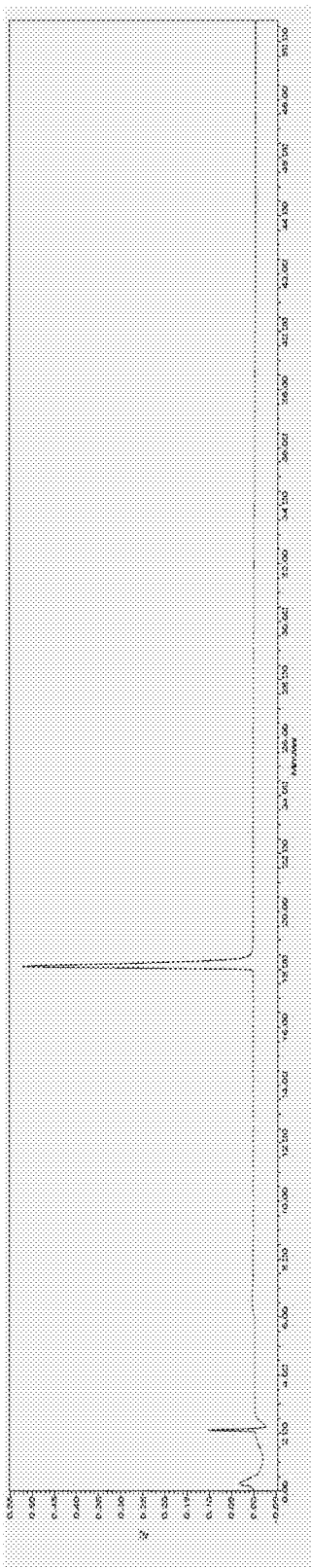
FIGS. 8A to 8Z are HPLC spectra of regular peptides (FIG. 8A, 8M) and sulfono-γ-AApeptides (FIGS. 8B-8L, 8N-8Z).

For the biotinylated sulfono-γ-AApeptides synthesis, a premixed solution of biotin (2 equiv.), HOBt (4 equiv.), and DIC (4 equiv.) in 2 mL DMF was added to the resin after dealloc and shaken for 24 h to complete the coupling reaction. After wash with DMF (×3) and DCM (×3), the resin was cleaved using TFA/DCM (6 mL, 1:1, v/v) for 3 h. The pure biotinylated sulfono-γ-AApeptides (>95%) were obtained using the same abovementioned method by HPLC. HPLC Trace 1
(SEQ ID NO: 1)
Ac-SQEQLEHRERSLQTLRDIQRMLF-NH$_2$ HRMS (ESI) ([M+H]$^+$) Calcd. for C$_{125}$H$_{209}$N$_{42}$O$_{39}$S: 2954.5383, found: 591.9159 [M+5H]$^{5+}$, 739.6416 [M+4H]$^{4+}$, 985.8539 [M+3H]$^{3+}$, 1478.2743 [M+2H]$^{2+}$ (FIG. 8A).

2

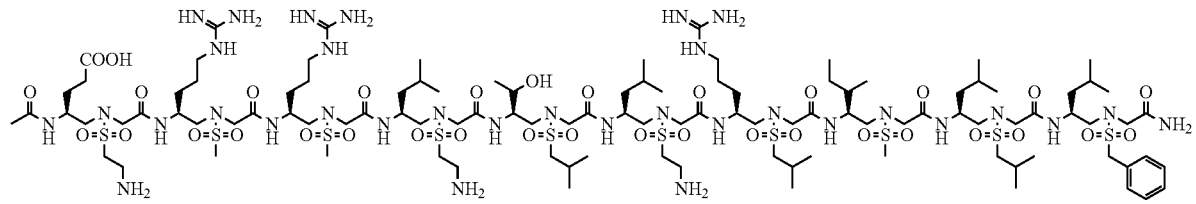 [SMILES: CCC(C)[C@@H](CN(CC(=O)N[C@@H](CC(C)C)CN(CC(=O)N[C@@H](CC(C)C)CN(CC(N)=O)S(=O)(=O)Cc1ccccc1)S(=O)(=O)CC(C)C)S(C)(=O)=O)NC(=O)CN(C[C@H](CCCNC(=N)N)NC(=O)CN(C[C@H](CC(C)C)NC(=O)CN(C[C@@H](NC(=O)CN(C[C@H](CC(C)C)NC(=O)CN(C[C@H](CCCNC(=N)N)NC(=O)CN(C[C@H](CCCNC(=N)N)NC(=O)CN(C[C@H](CCC(=O)O)NC(C)=O)S(=O)(=O)CCN)S(C)(=O)=O)S(C)(=O)=O)S(=O)(=O)CCN)C(C)O)S(=O)(=O)CC(C)C)S(=O)(=O)CCN)S(=O)(=O)CC(C)C]

Figure 8B:
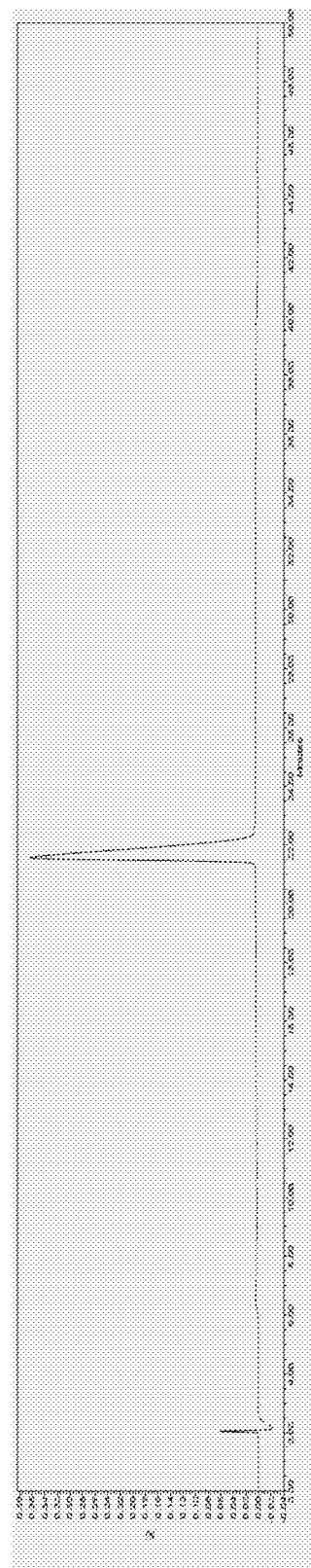

HRMS (ESI) ([M+H]$^+$) Calcd. for C$_{107}$H$_{212}$N$_{33}$O$_{34}$S$_{10}$: 2823.3082, found: 707.0802 [M+4H]$^{4+}$, 942.4420 [M+3H]$^{3+}$, 1413.1570 [M+2H]$^{2+}$ (FIG. 8B).

3

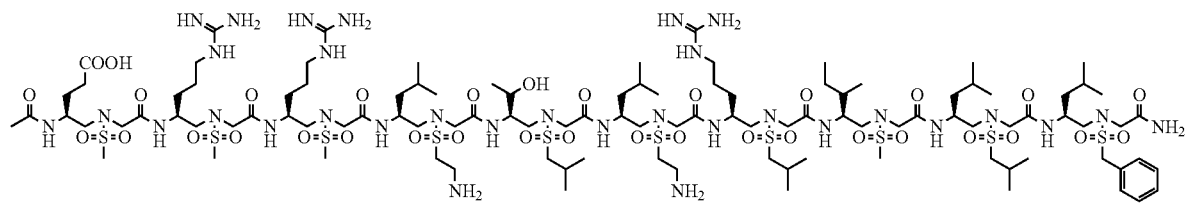

Figure 8C:
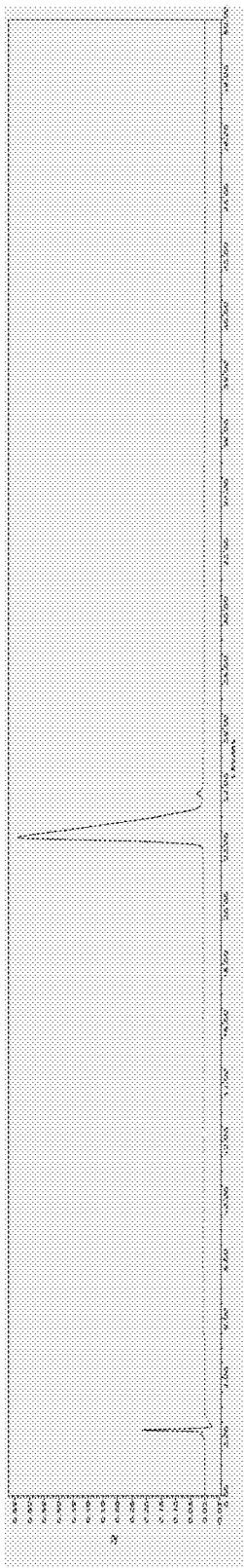

HRMS (ESI) ([M+H]$^+$) Calcd. for C$_{106}$H$_{209}$Na$_{32}$O$_{34}$S$_{10}$: 2794.2816, found: 699.8256 [M+4H]$^{4+}$, 932.7664 [M+3H]$^{3+}$, 1398.6429 [M+2H]$^{2+}$ (FIG. 8C).

4

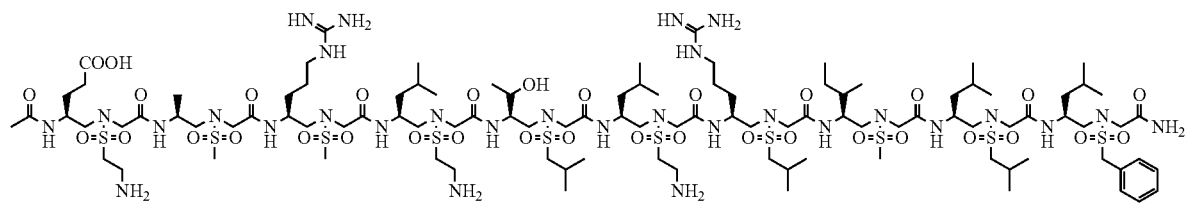

Figure 8D:
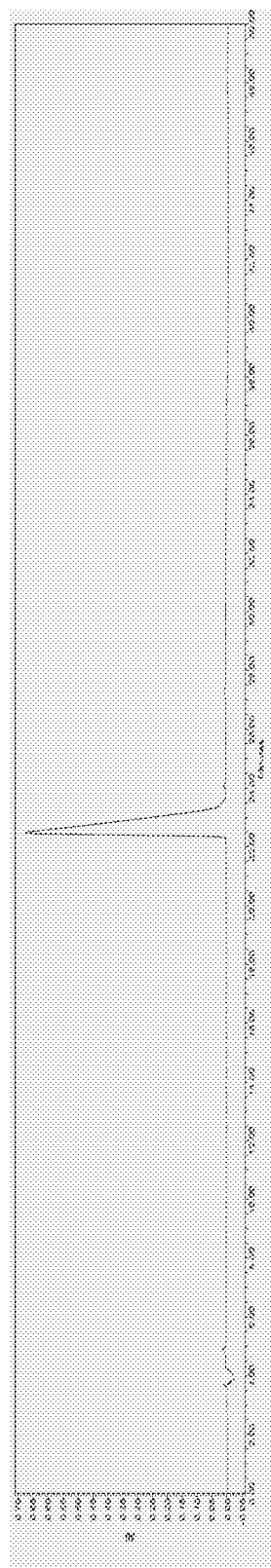
Figure 8E:
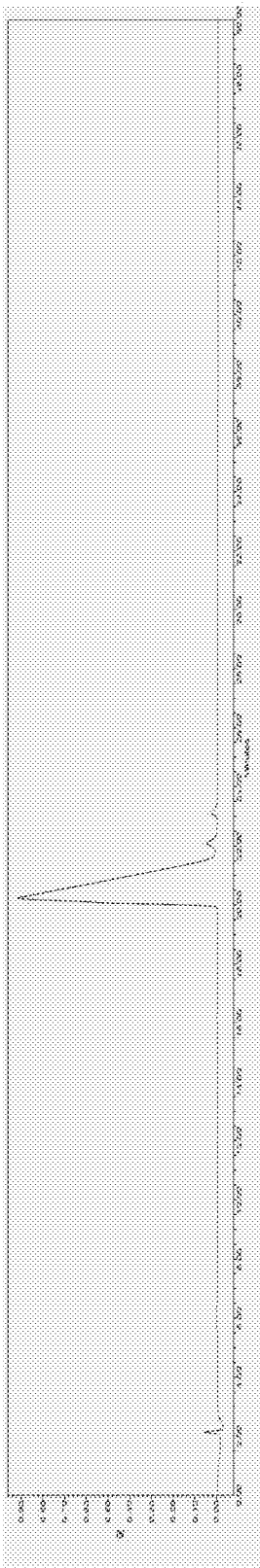
Figure 8F:
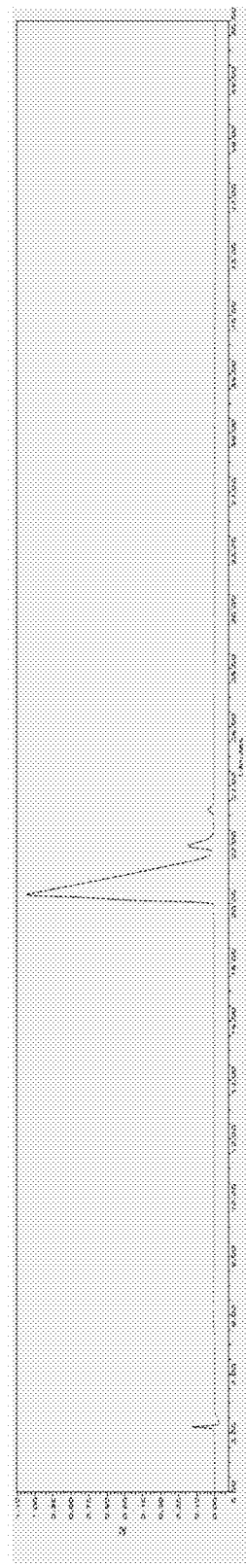
Figure 8G:
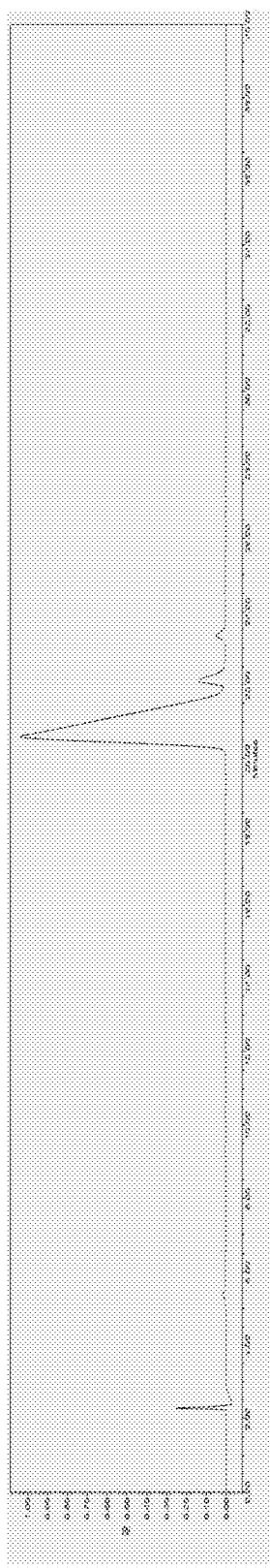
Figure 8H:
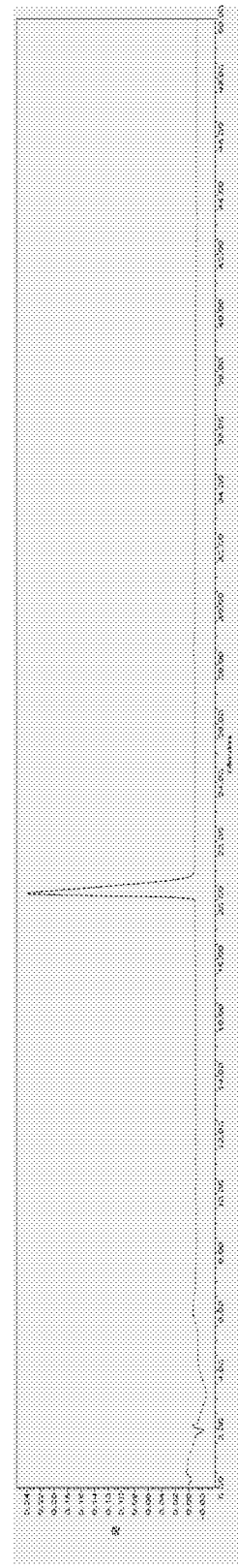

HRMS (ESI) ([M+H]$^+$) Calcd. for $C_{104}H_{205}N_{30}O_{34}S_{10}$: 2738.2442, found: 548.8560 [M+5H]$^{5+}$, 685.8159 [M+4H]$^{4+}$, 914.0856 [M+3H]$^{2+}$ (FIG. 8D).
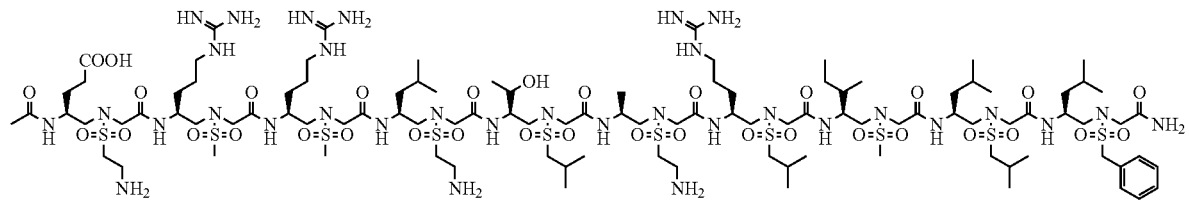
5
HRMS (ESI) ([M+H]$^+$) Calcd. for $C_{104}H_{206}N_{33}O_4S_1O$: 2781.2612, found: 696.5706 [M+4H]$^{4+}$, 928.4252 [M+3H]$^{3+}$, 1392.1317 [M+2H]$^{2+}$ (FIG. 8E).
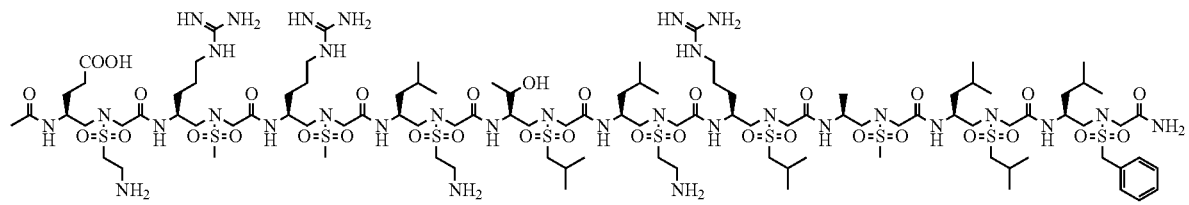
6
HRMS (ESI) ([M+H]$^+$) Calcd. for $C_{104}H_{206}N_{33}O_{34}S_{10}$: 2781.2612, found: 696.5704 [M+4H]$^{4+}$, 928.4238 [M+3H]$^{3+}$, 1392.1294 [M+2H]$^{2+}$ (FIG. 8F).
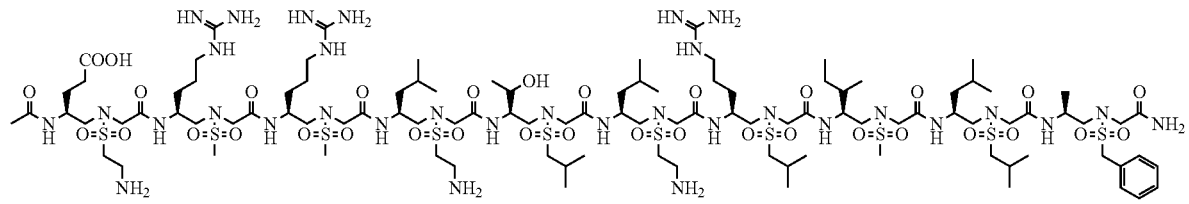
7
HRMS (ESI) ([M+H]$^+$) Calcd. for $C_{104}H_{206}N_{33}O_{34}S_{10}$: 2781.2612, found: 696.5699 [M+4H]$^{4+}$, 928.4243 [M+3H]$^{3+}$, 1392.1294 [M+2H]$^{2+}$ (FIG. 8G).
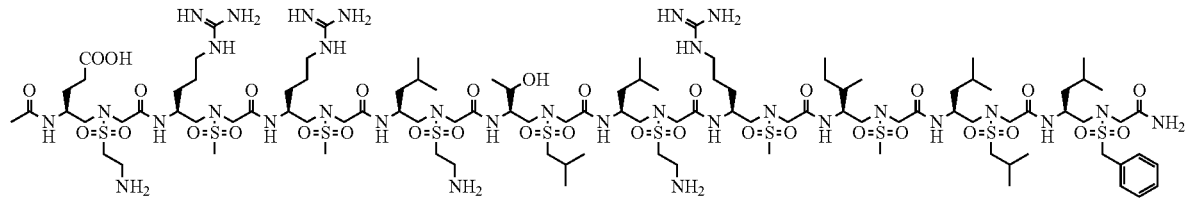
8
HRMS (ESI) ([M+H]$^+$) Calcd. for $C_{104}H_{206}N_{33}O_{34}S_{10}$: 2781.2612, found: 696.5706 [M+4H]$^{4+}$, 928.4256 [M+3H]$^{3+}$, 1392.1323 [M+2H]$^{2+}$ (FIG. 8H).

Figure 8I:
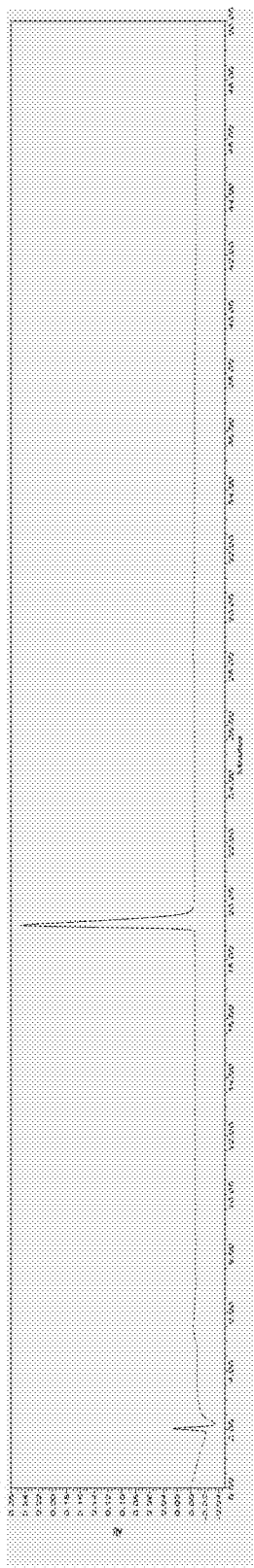
Figure 8J:
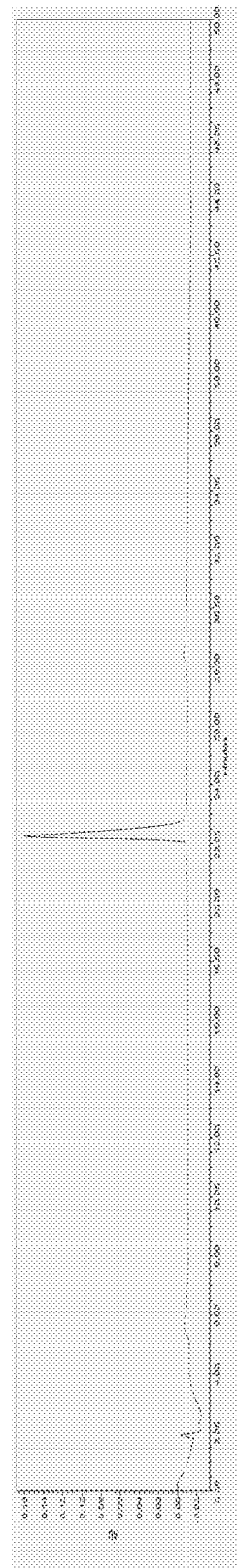

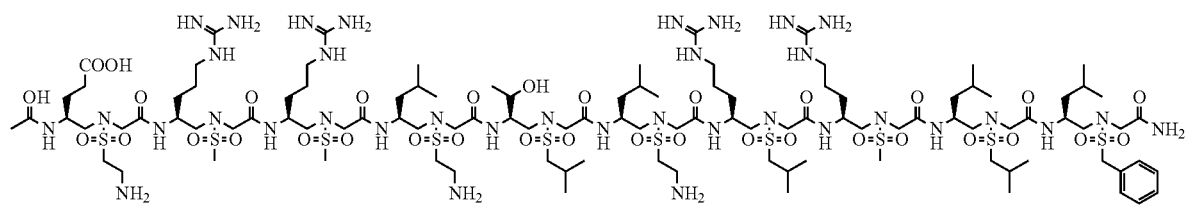
9
HRMS (ESI) ([M+H]⁺) Calcd. for $C_{107}H_{213}N_{36}O_{34}S_{10}$: 2866.3252, found: 717.8380 [M+4H]⁴⁺, 956.7816 [M+3H]³⁺, 1434.6666 [M+2H]²⁺ (FIG. 8I).
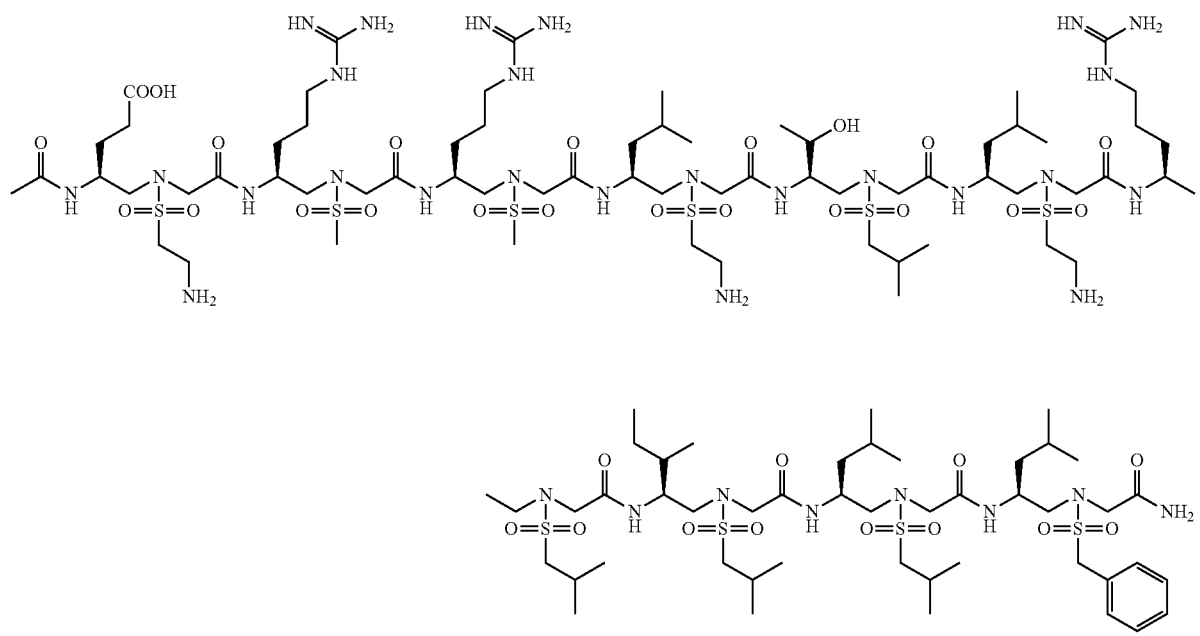
10
HRMS (ESI) ([M+H]⁺) Calcd. for $C_{110}H_{218}N_{33}O_3S_{10}$: 2865.3551, found: 717.5952 [M+4H]⁴⁺, 956.4579 [M+3H]³⁺, 1434.1813 [M+2H]²⁺ (FIG. 8J).
11
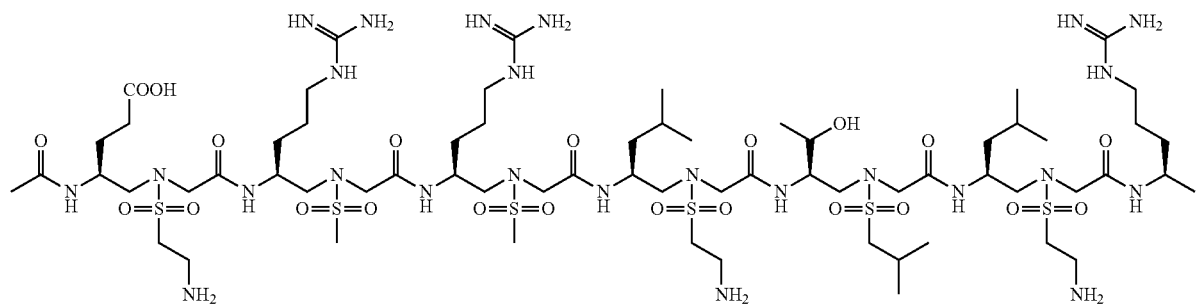

Figure 8K:
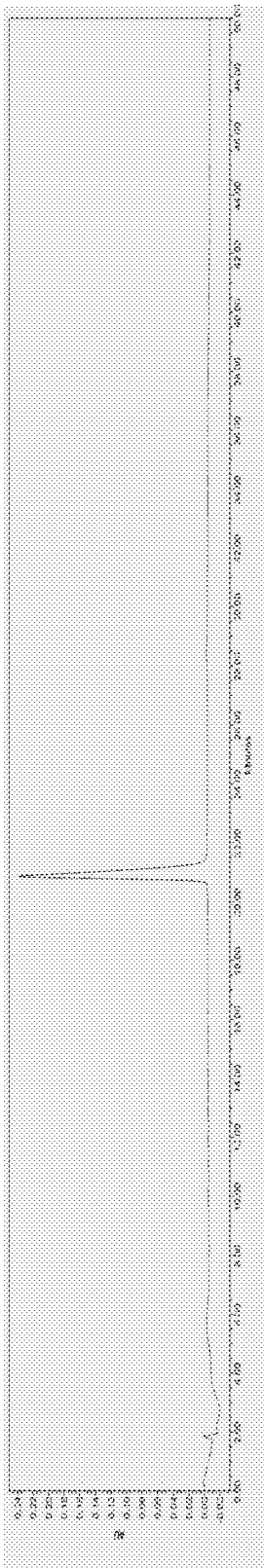
Figure 8L:
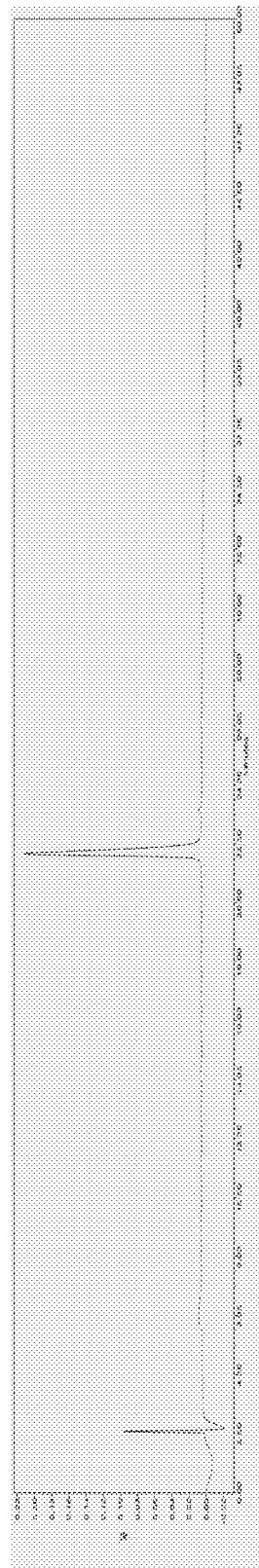
Figure 8M:
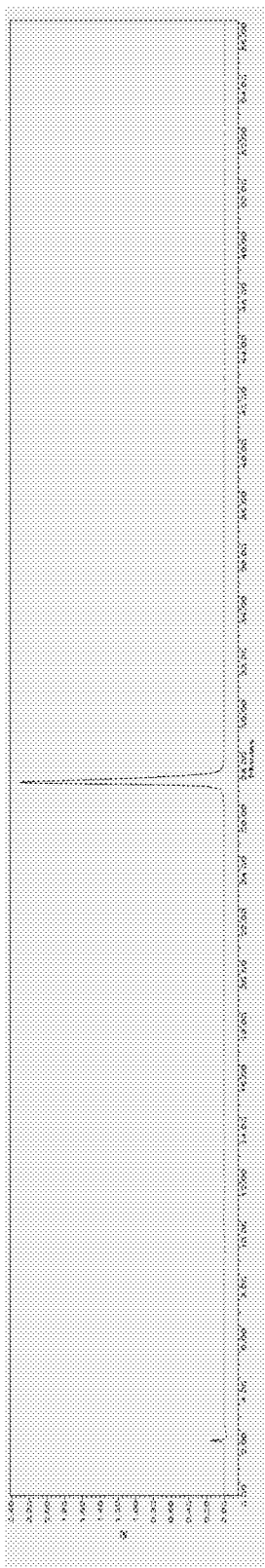

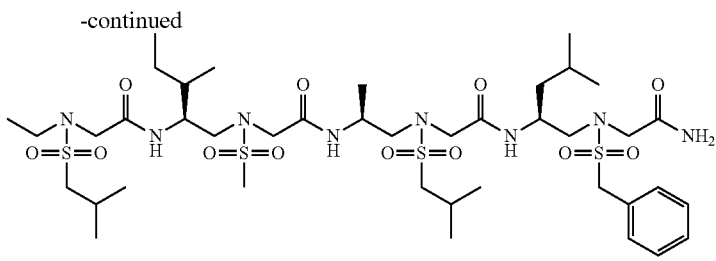
HRMS (ESI) ([M+H]$^+$) Calcd. for $C_{110}H_{218}N_{33}O_3S_{10}$: 2865.3551, found: 717.5952 [M+4H]$^{4+}$, 956.4579 [M+3H]$^{3+}$, 1434.1813 [M+2H]$^{2+}$ (FIG. 8K).
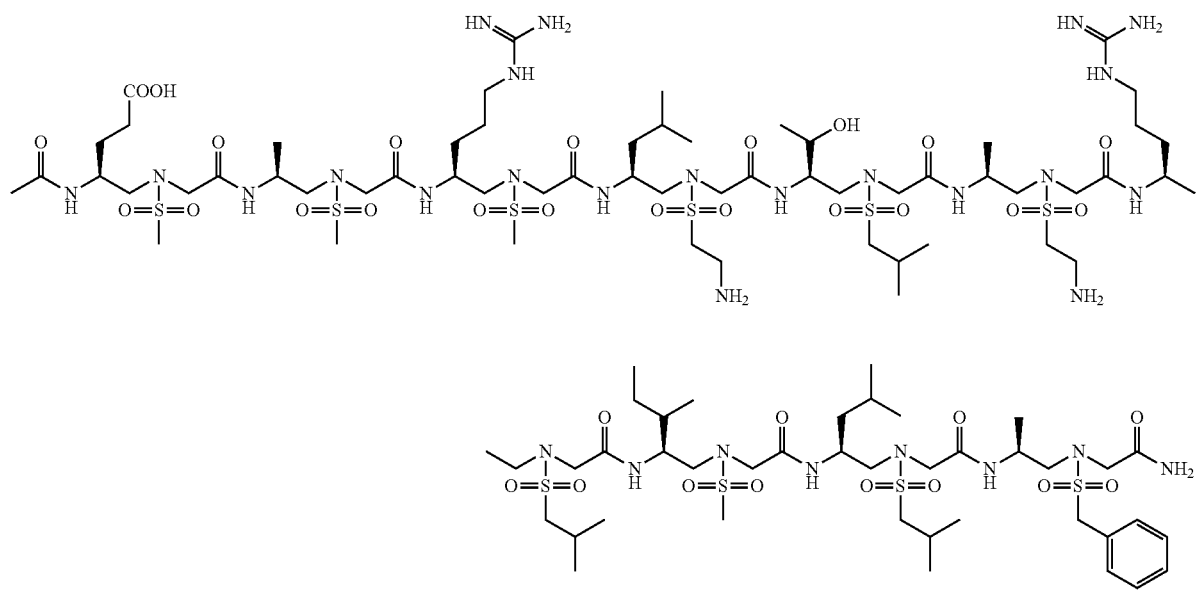
HRMS (ESI) ([M+H]$^+$) Calcd. for $C_{97}H_{190}N_{29}O_3S_{10}$: 2625.1237, found: 657.5362 [M+4H]$^{4+}$, 876.3809 [M+3H]$^{3+}$, 1314.0647 [M+2H]$^{2+}$ (FIG. 8L).
```
1-FITC
        (SEQ ID NO: 1, underlined portion)
Flu-Beta-Ala-SQEQLEHRERSLQTLRDIQRMLF
```
HRMS (ESI) ([M+H]$^+$) Calcd. for $C_{147}H_{225}N_{44}O_{44}S_2$: 3374.6163, found: 675.7287 [M+5H]$^{5+}$, 844.4084 [M+4H]$^{4+}$, 1125.5406 [M+3H]$^{3+}$, 1687.8041 [M+2H]$^{2+}$ (FIG. 8M).
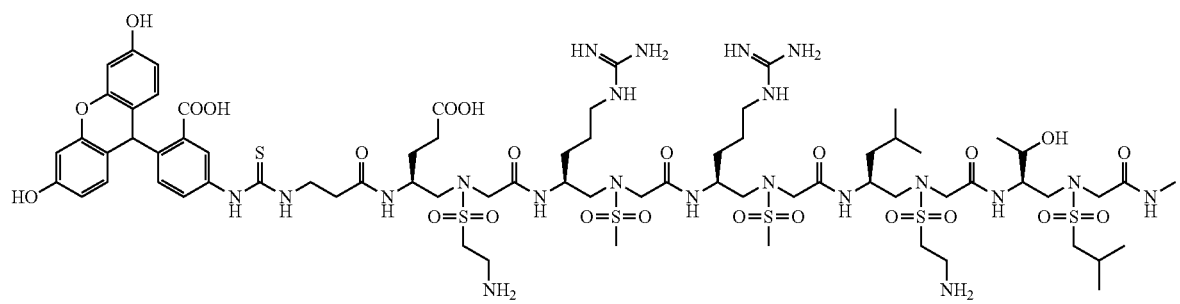

Figure 8N:
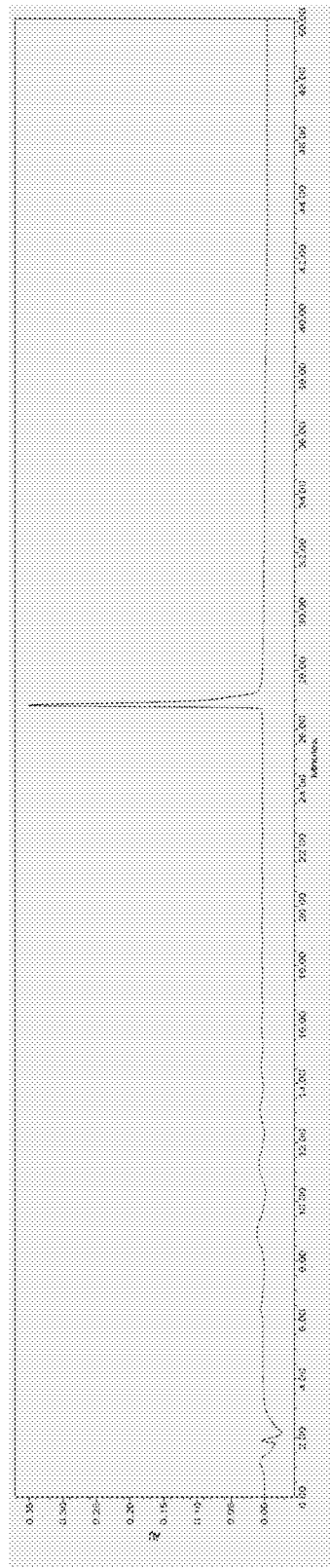
Figure 8O:
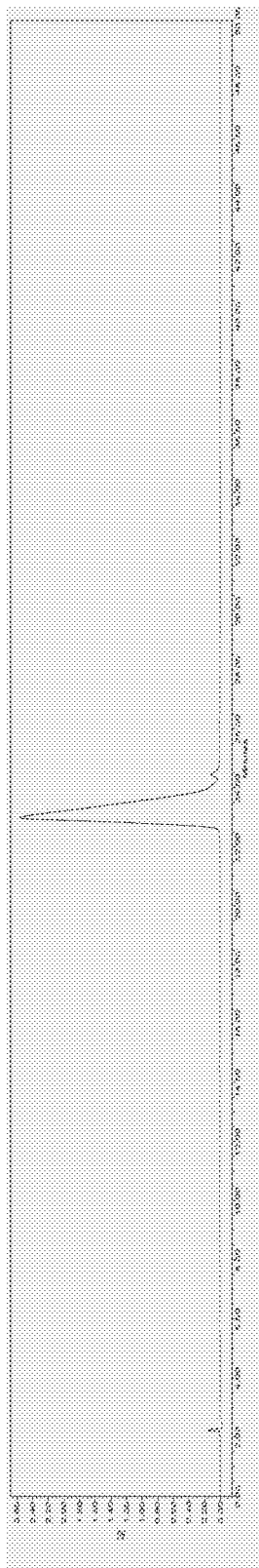

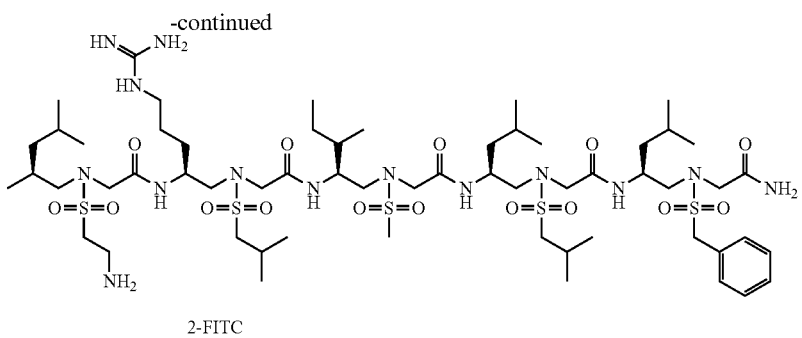
2-FITC
HRMS (ESI) ([M+H]$^+$) Calcd. for $C_{129}H_{228}N_{35}O_{39}S_{11}$: 3243.3861, found: 649.4835 [M+5H]$^{5+}$, 811.6012 [M+4H]$^{4+}$, 1081.7983 [M+3H]$^{3+}$, 1622.1922 [M+2H]$^{2+}$ (FIG. 8N).
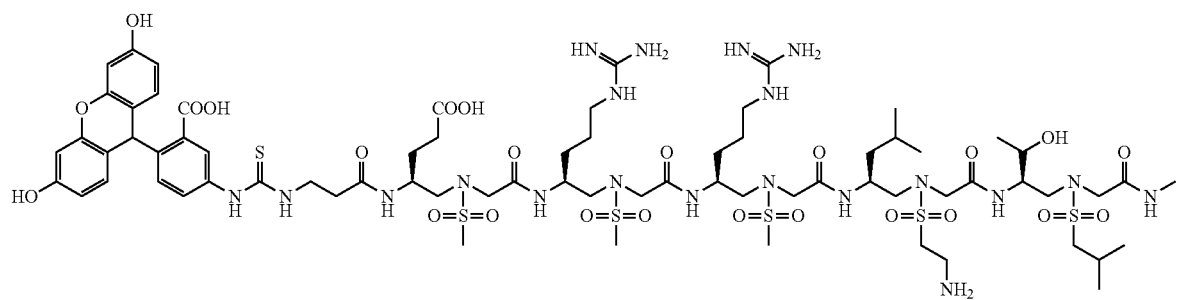
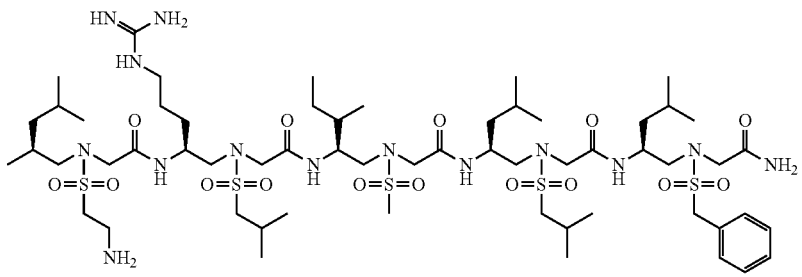
3-FITC
HRMS (ESI) ([M+H]$^+$) Calcd. for $C_{128}H_{225}Na_{34}O_{39}S_{11}$: 3214.3596, found: 643.6762 [M+5H]$^{5+}$, 804.3418 [M+4H]$^{4+}$, 1072.1186 [M+3H]$^{3+}$, 1607.6726 [M+2H]$^{2+}$ (FIG. 8O).
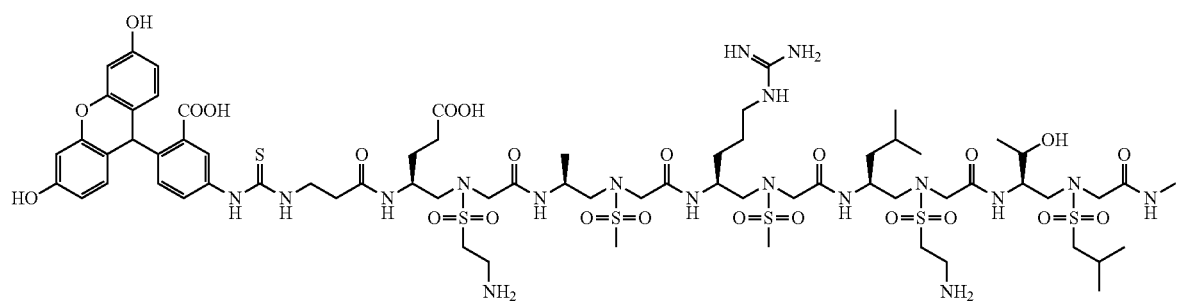

Figure 8P:
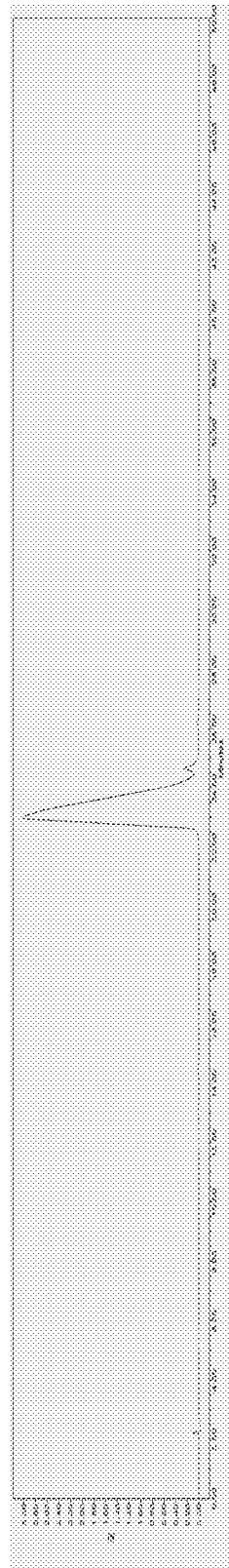
Figure 8Q:
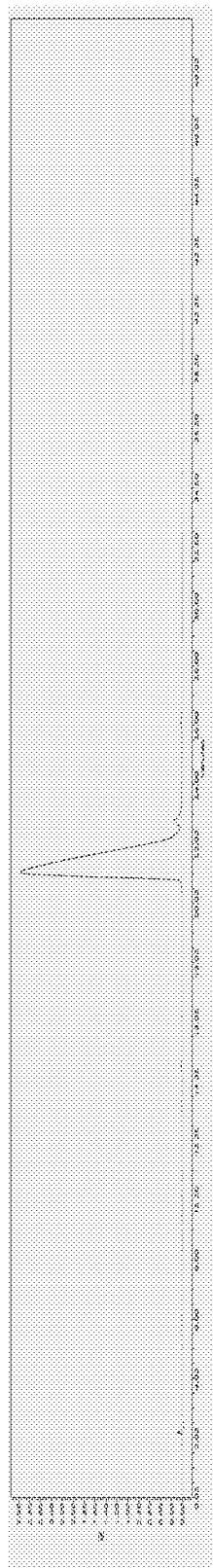

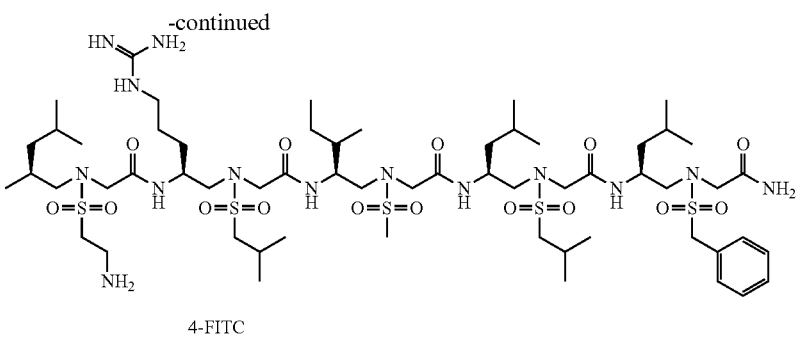
4-FITC
HRMS (ESI) ([M+H]$^+$) Calcd. for $C_{126}H_{221}N_{32}O_{39}S_{11}$: 3158.3221, found: 632.4701 [M+5H]$^{5+}$, 790.3345 [M+4H]$^{4+}$, 1053.4426 [M+3H]$^{3+}$, 1579.6599 [M+2H]$^{2+}$ (FIG. 8P).
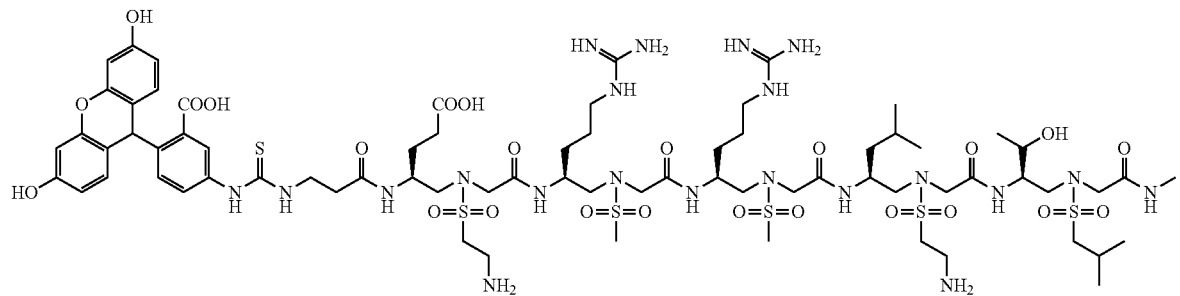
15
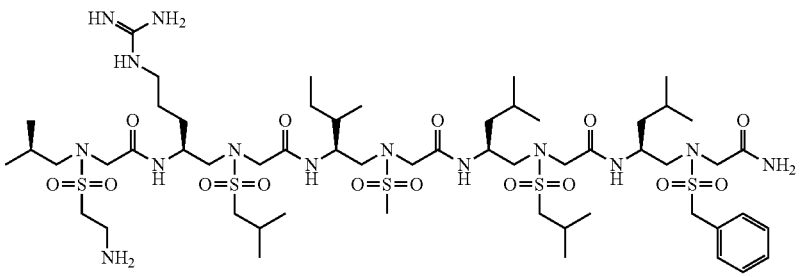
5-FITC
HRMS (ESI) ([M+H]$^+$) Calcd. for $C_{126}H_{222}N_{35}O_{39}S_{11}$: 3201.3392, found: 641.0726 [M+5H]$^{5+}$, 801.0880 [M+4H]$^{4+}$, 1067.7806 [M+3H]$^{3+}$, 1601.1656 [M+2H]$^{2+}$ (FIG. 8Q).
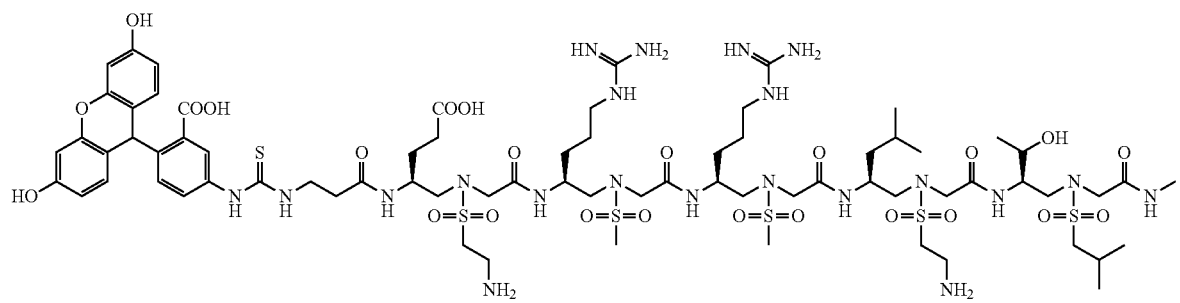

Figure 8R:
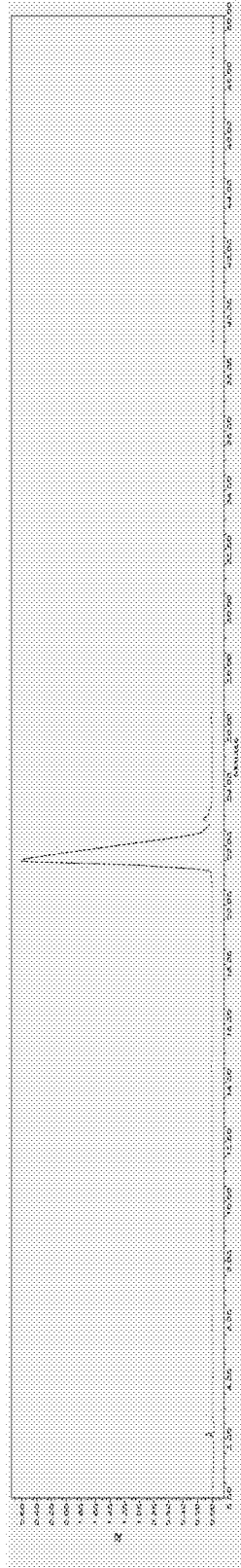
Figure 8S:
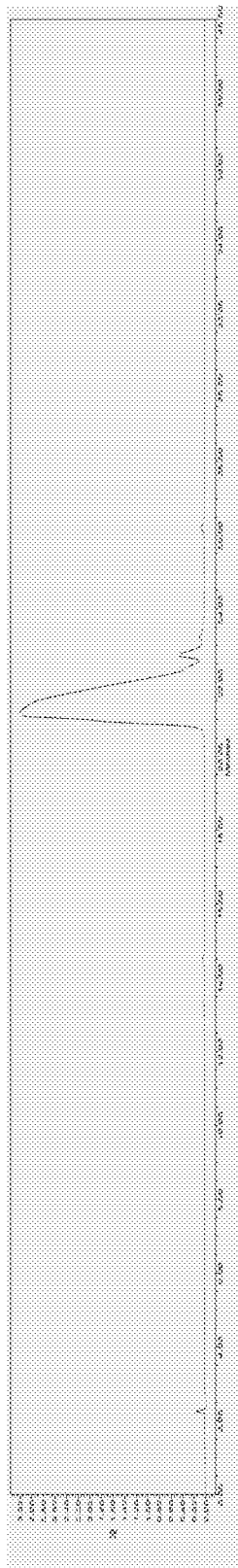

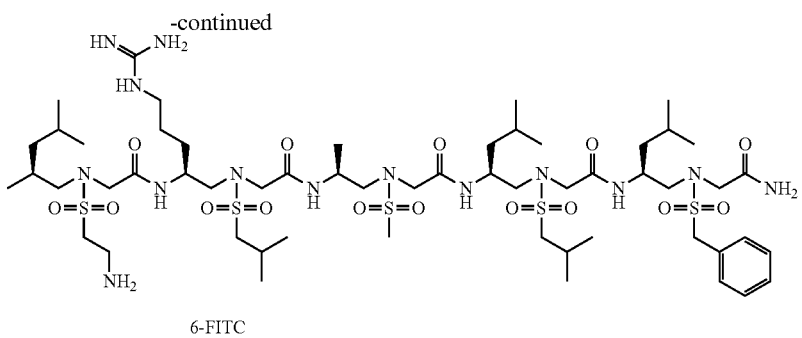
6-FITC
HRMS (ESI) ([M+H]$^+$) Calcd. for $C_{126}H_{222}N_{35}O_{39}S_{11}$: 3201.3392, found: 641.0728 [M+5H]$^{5+}$, 801.0878 [M+4H]$^{4+}$, 1067.7796 [M+3H]$^{3+}$, 1601.1652 [M+2H]$^{2+}$ (FIG. 8R).
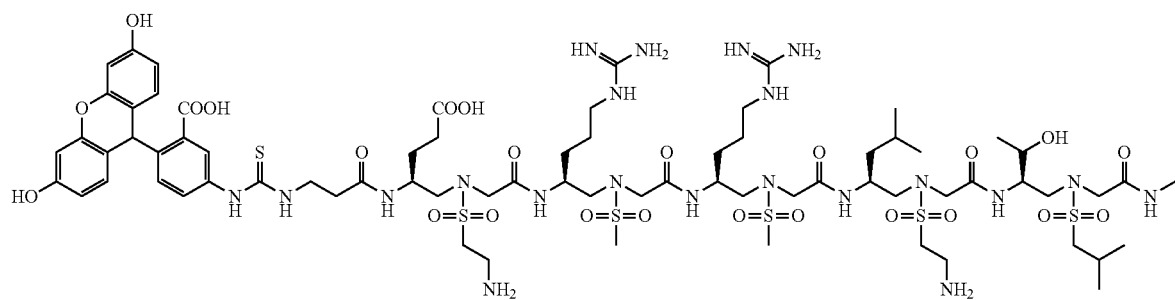
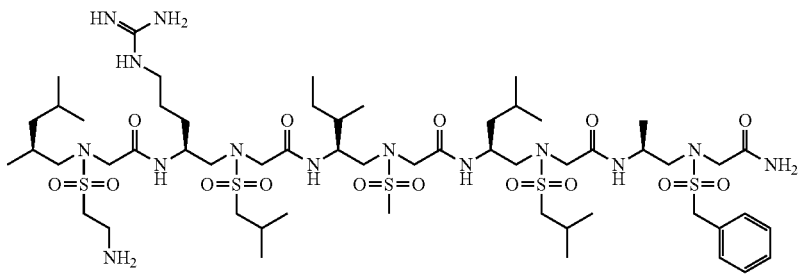
7-FITC
HRMS (ESI) ([M+H]$^+$) Calcd. for $C_{126}H_{222}N_{35}O_{39}S_{11}$: 3201.3392, found: 641.0739 [M+5H]$^{5+}$, 801.0890 [M+4H]$^{4+}$, 1067.7820 [M+3H]$^{3+}$, 1601.1668 [M+2H]$^{2+}$ (FIG. 8S).
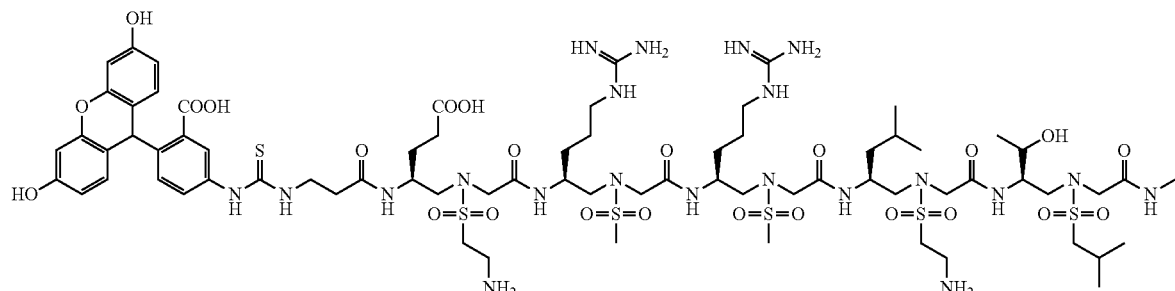

Figure 8T:
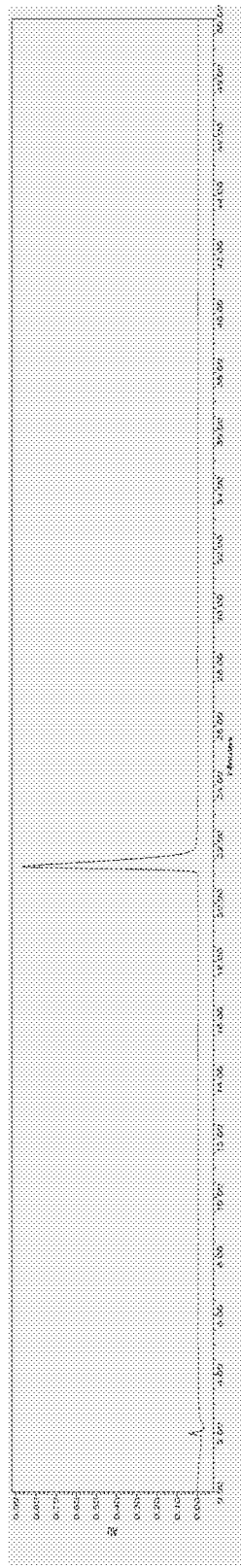
Figure 8U:
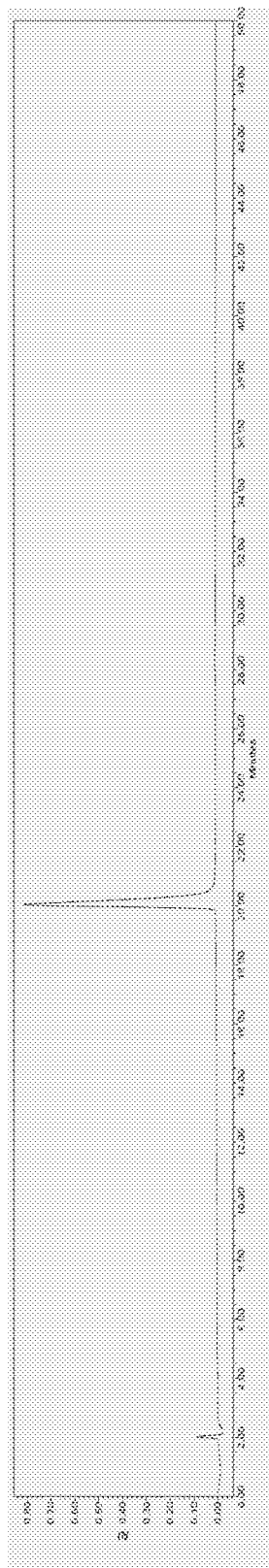

-continued
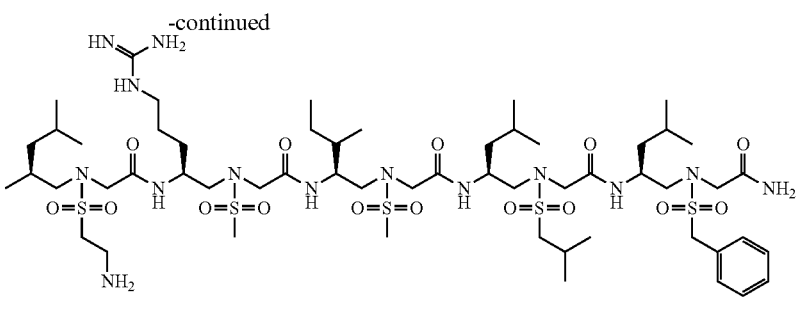
8-FITC
HRMS (ESI) ([M+H]$^+$) Calcd. for C$_{126}$H$_{222}$N$_{35}$O$_{39}$S$_{11}$: 3201.3392, found: 641.0731 [M+5H]$^{5+}$, 801.0882 [M+4H]$^{4+}$, 1067.7811 [M+3H]$^{3+}$, 1601.1670 [M+2H]$^{2+}$ (FIG. 8T).
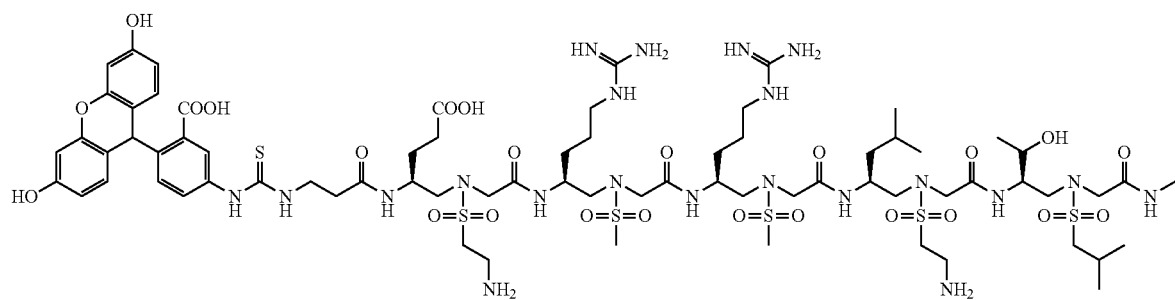
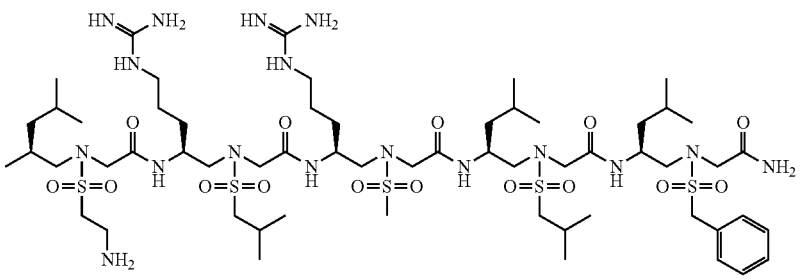
9-FITC
HRMS (ESI) ([M+H]$^+$) Calcd. for C$_{129}$H$_{299}$N$_{38}$O$_{39}$S$_{11}$: 3286.4032, found: 658.0845 [M+5H]$^{5+}$, 822.3523 [M+4H]$^{4+}$, 1096.1327 [M+3H]$^{3+}$, 1644.1916 [M+2H]$^{2+}$ (FIG. 8U).
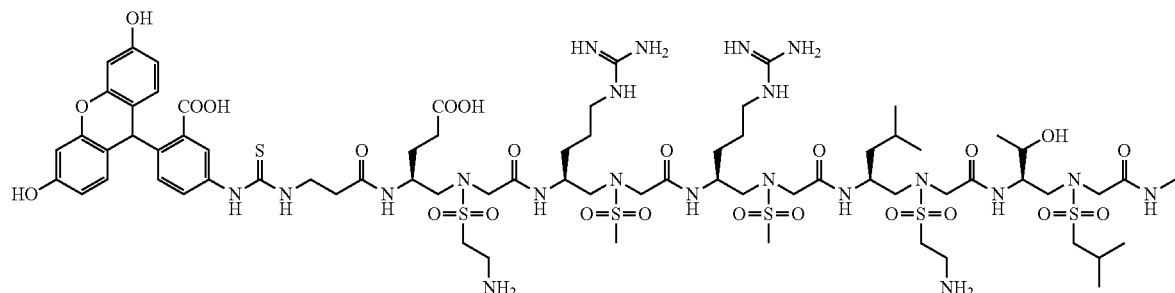

Figure 8V:
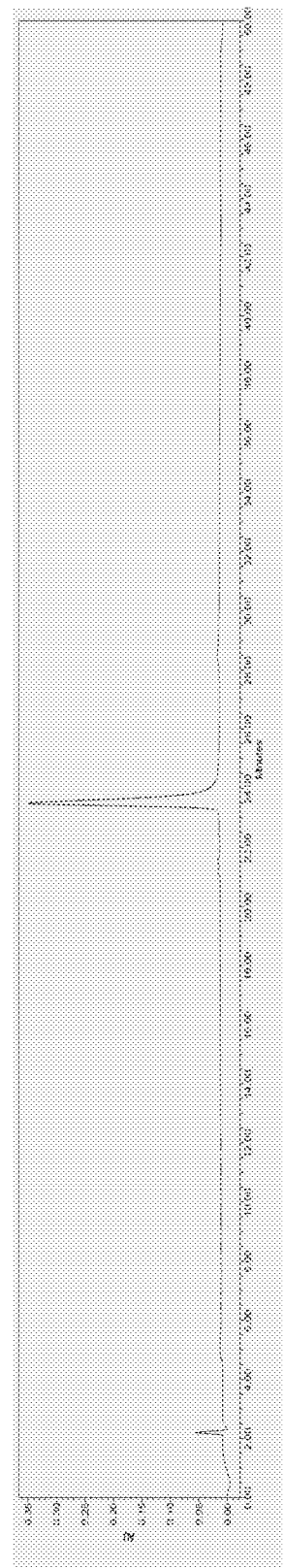
Figure 8W:
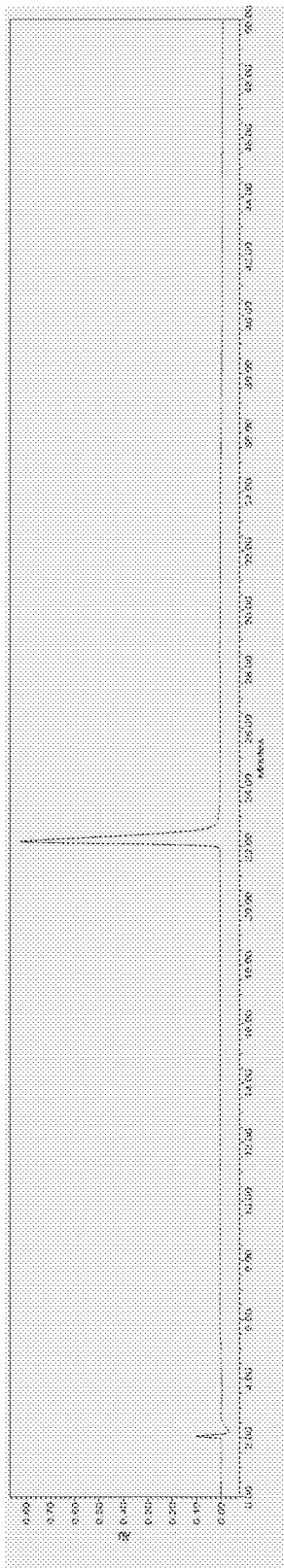

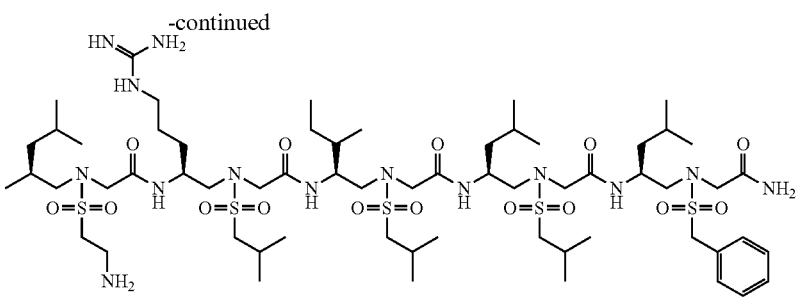
10-FITC
HRMS (ESI) ([M+H]⁺) Calcd. for $C_{132}H_{234}N_{35}O_{39}S_{11}$: 3285.4331, found: 657.8915 [M+5H]$^{5+}$, 822.1112 [M+4H]$^{4+}$, 1095.8114 [M+3H]$^{3+}$, 1643.2136 [M+2H]$^{2+}$ (FIG. 8V).
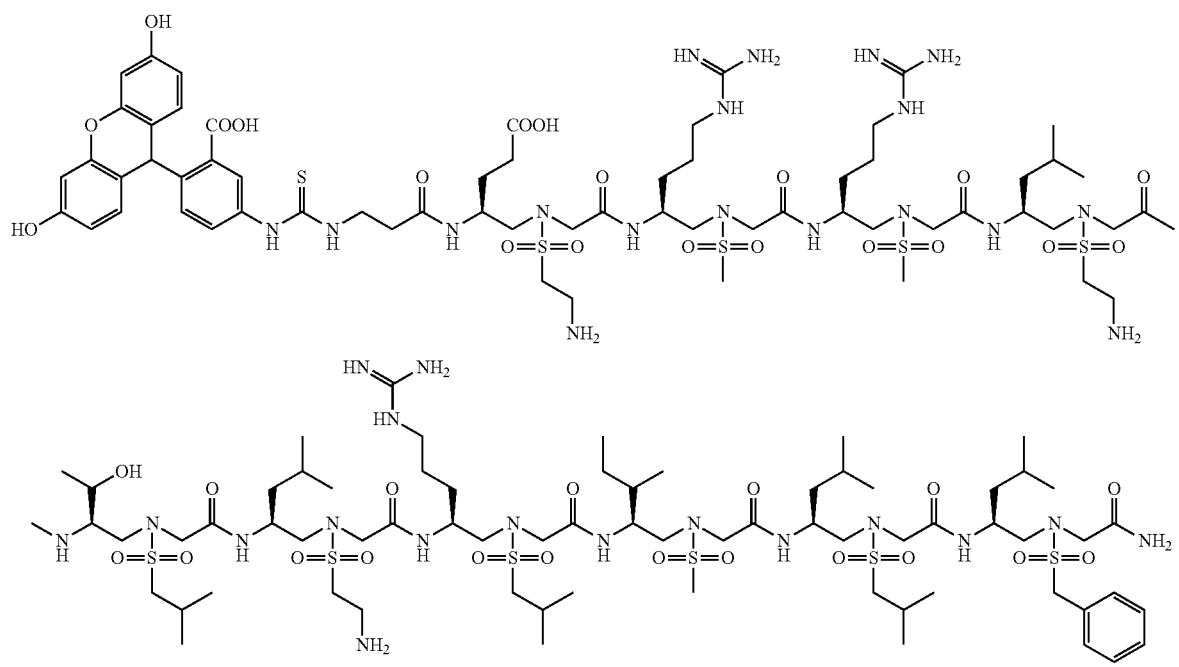
11-FITC
HRMS (ESI) ([M+H]⁺) Calcd. for $C_{126}H_{222}N_{35}O_{39}S_{11}$: 3201.3392, found: 641.0734 [M+5H]$^{5+}$, 801.0887 [M+4H]$^{4+}$, 1067.7812 [M+3H]$^{3+}$, 1601.1666 [M+2H]$^{2+}$ (FIG. 8w).
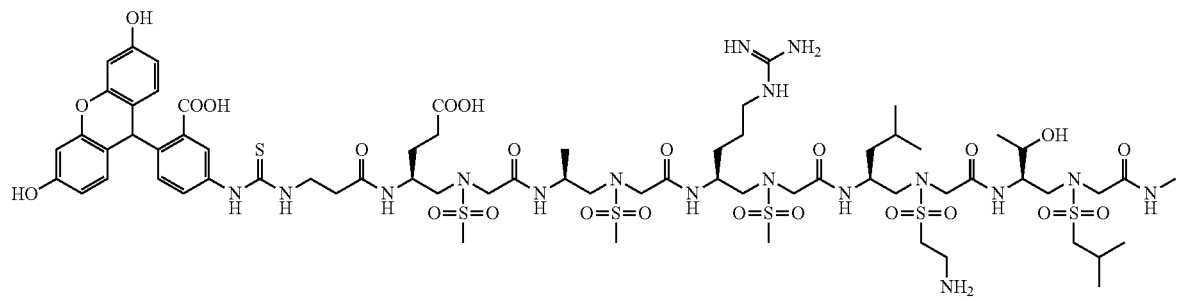

Figure 8X:
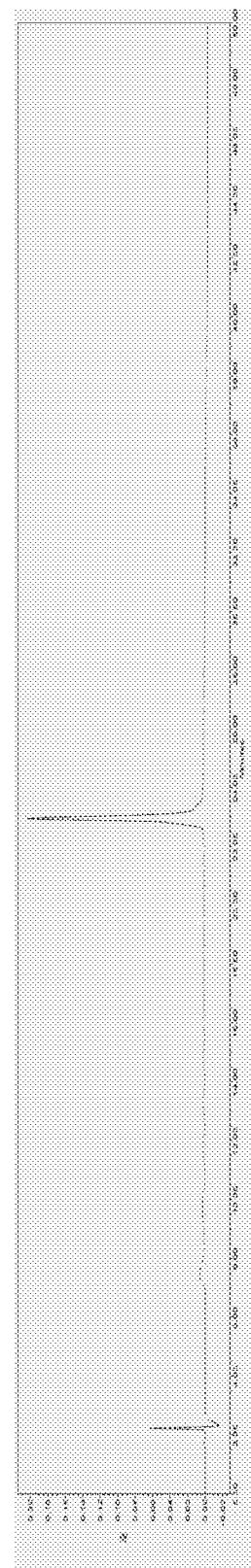
Figure 8Y:
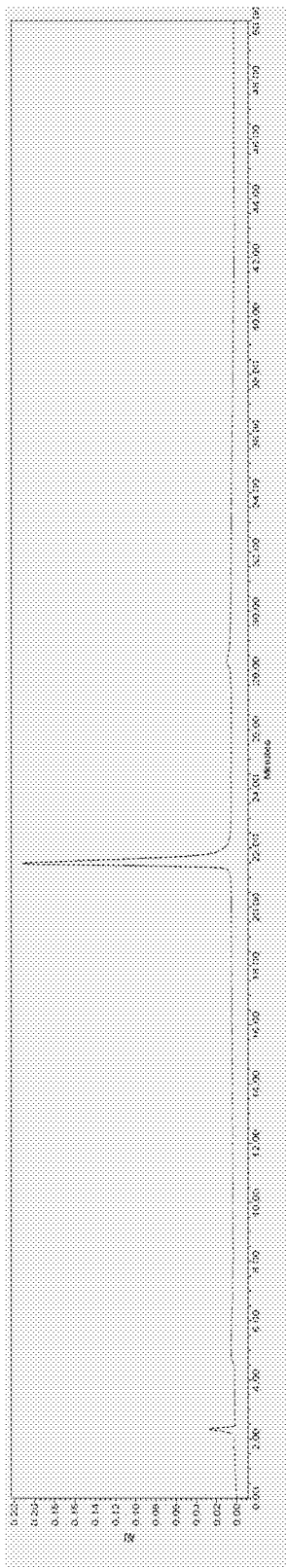

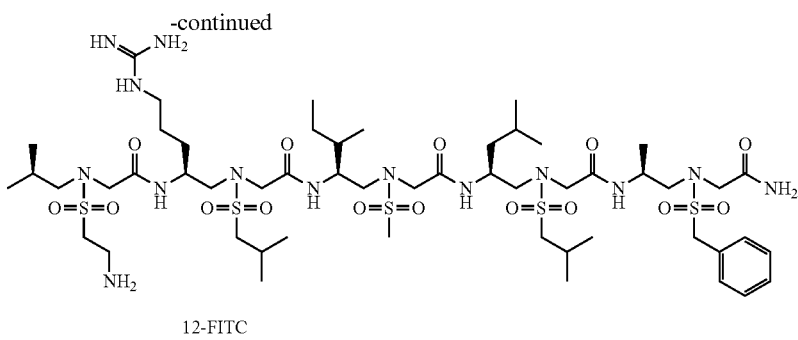
12-FITC
HRMS (ESI) ([M+H]⁺) Calcd. for $C_{119}H_{206}N_{31}O_{39}S_{11}$: 3045.2017, found: 784.5418 [M+4Na]⁴⁺ (FIG. 8X).
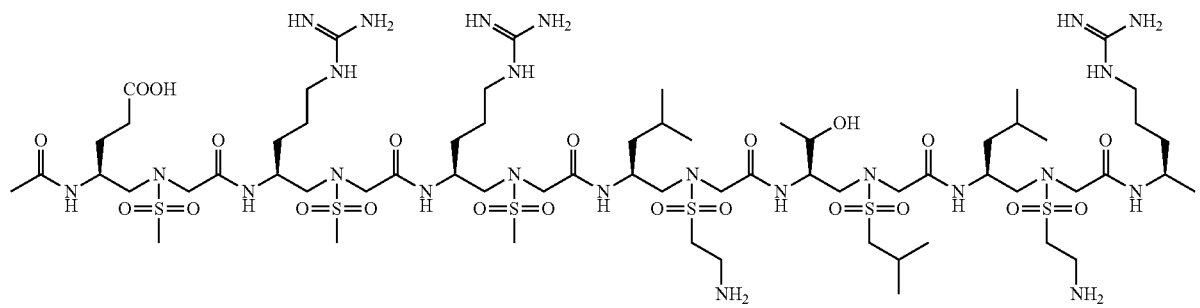
15
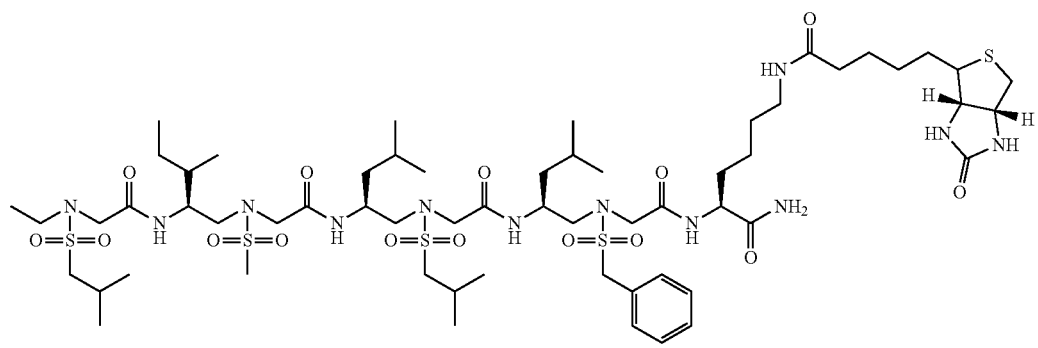
3-Biotin
HRMS (ESI) ([M+H]⁺) Calcd. for $C_{122}H_{235}N_{36}O_{37}S_{11}$: 3148.4542, found: 630.8994 [M+5H]⁵⁺, 788.3710 [M+4H]⁴⁺, 1050.8246 [M+3H]³⁺, 1575.7312 [M+2H]²⁺ (FIG. 8Y).

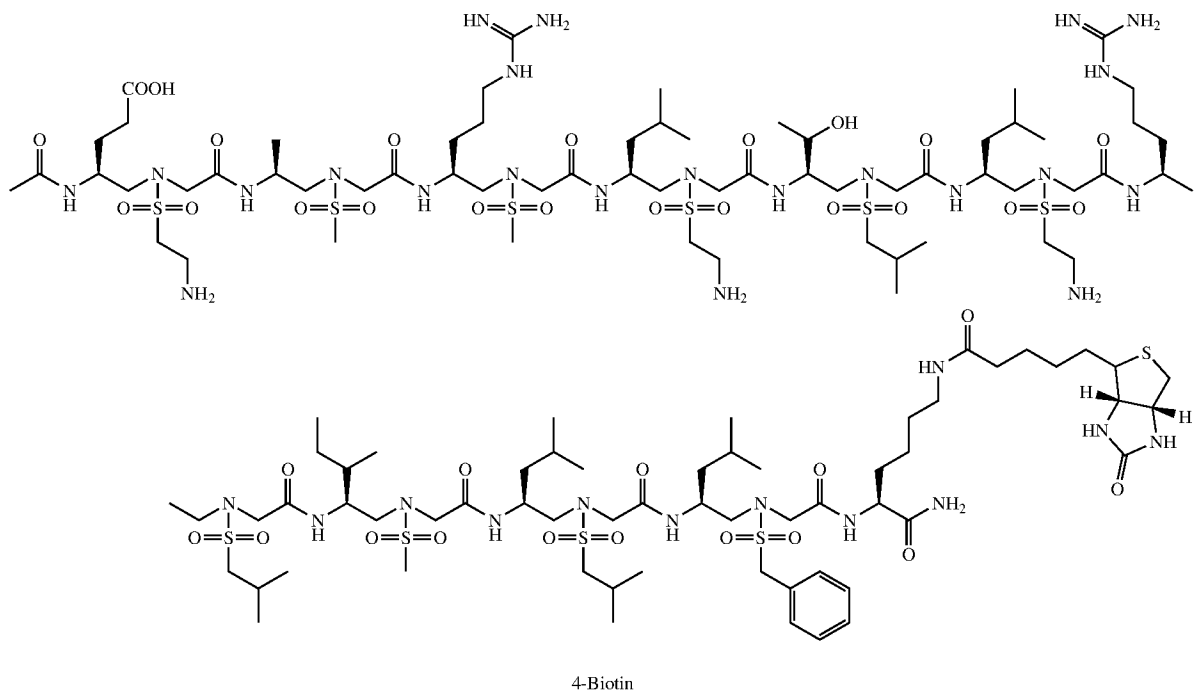

4-Biotin

Figure 8Z:
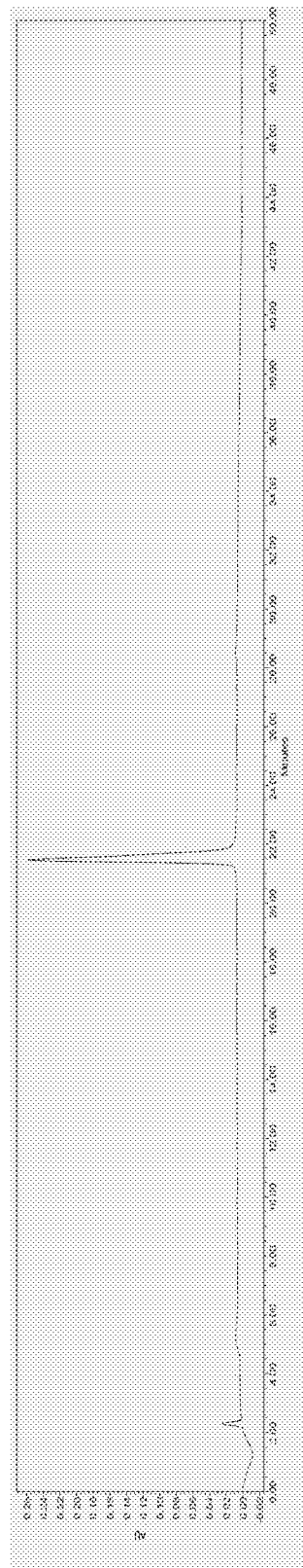
Figure 9A:
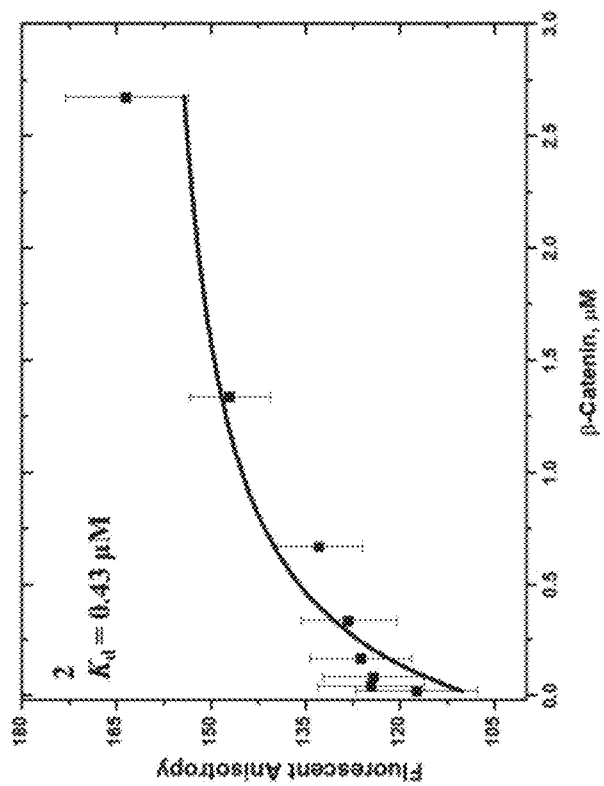
FIGS. 9A to 9L show Kd data of regular peptide 1 (FIG. 9A) and sulfono-γ-AApeptides 2-12 (FIGS. 9B-9L).
Figure 9B:
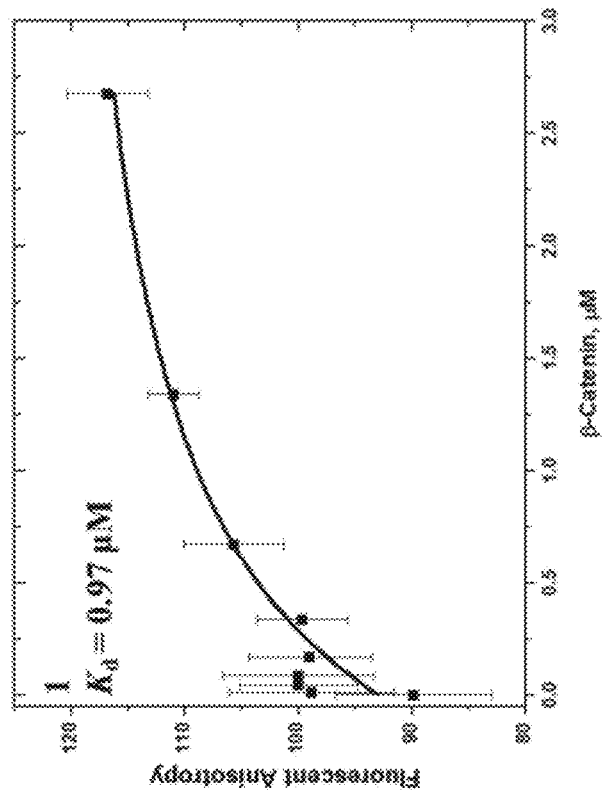
Figure 9D:
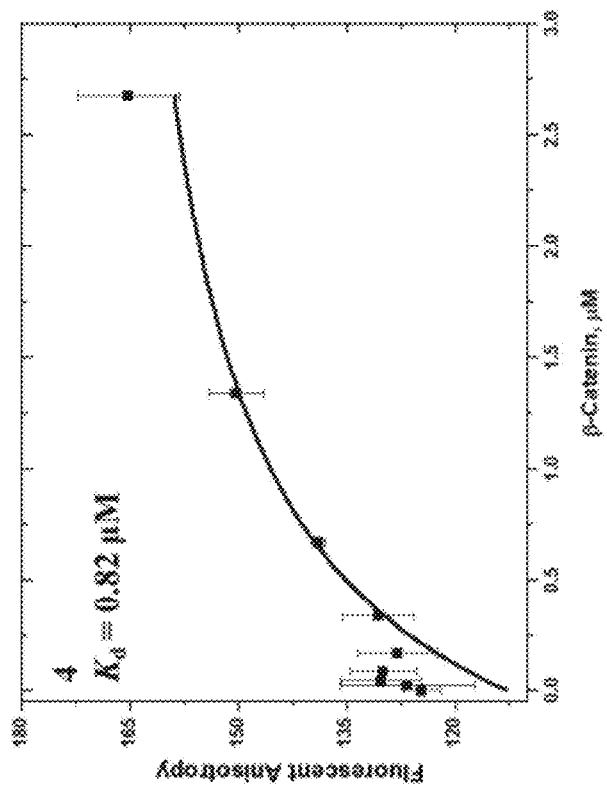
Figure 9C:
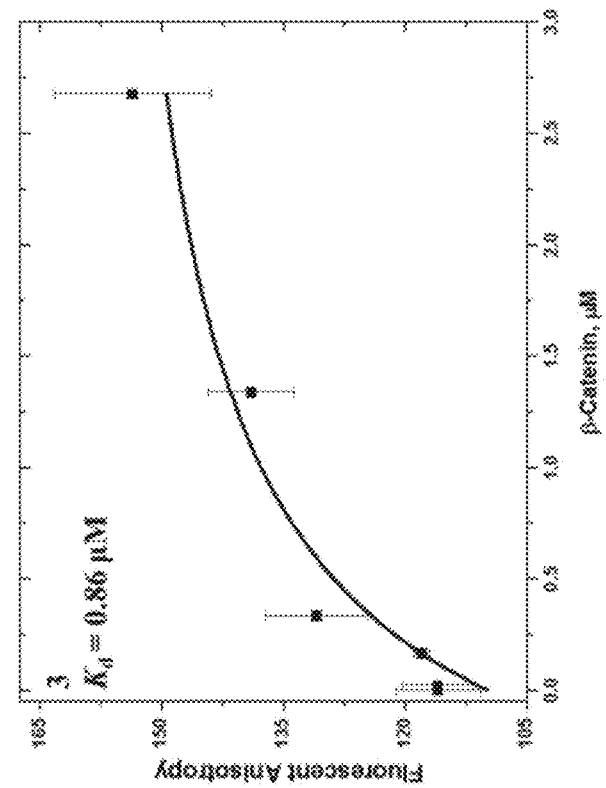
Figure 9F:
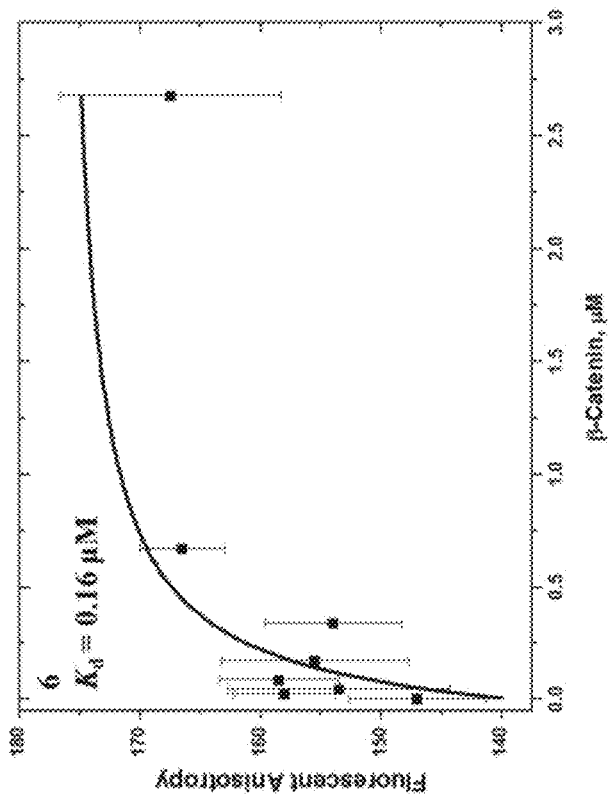
Figure 9E:
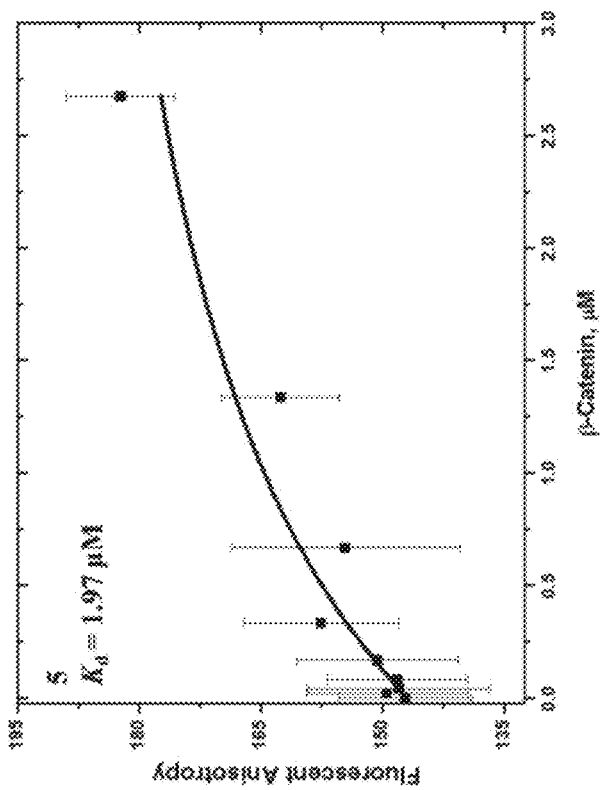
Figure 9H:
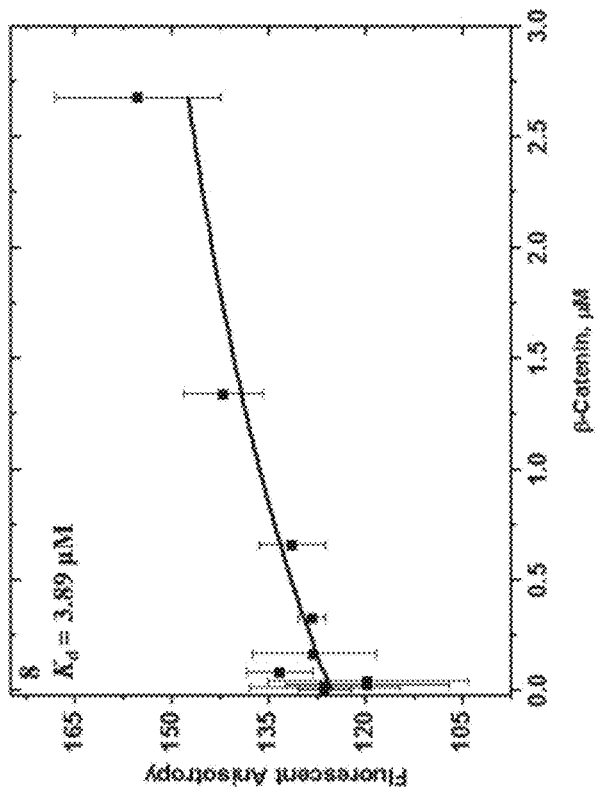
Figure 9G:
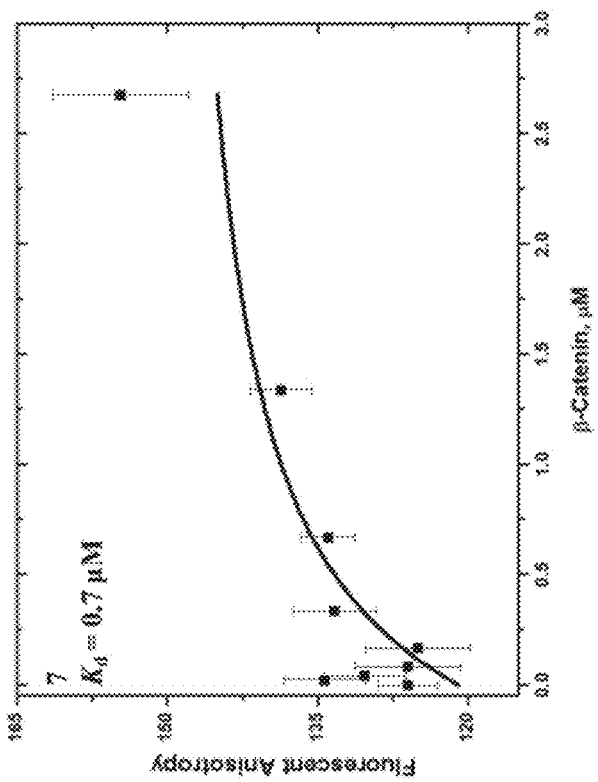
Figure 9I:
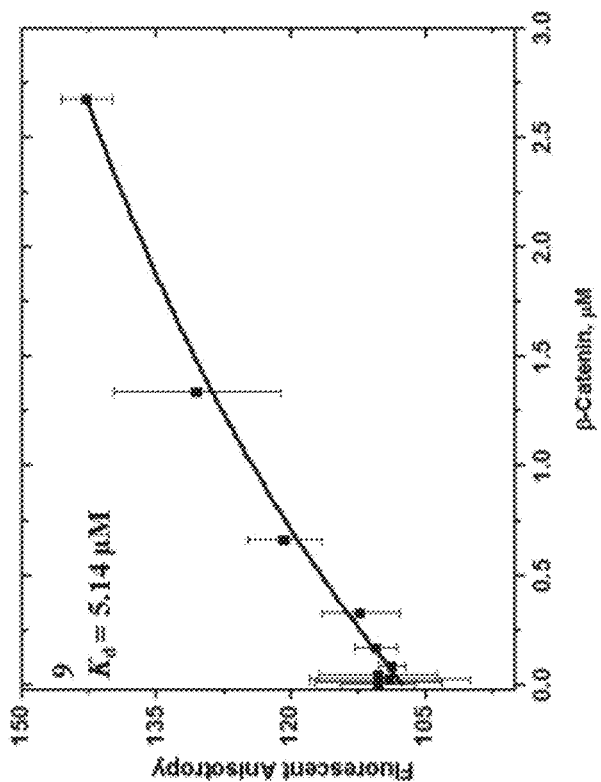
Figure 9J:
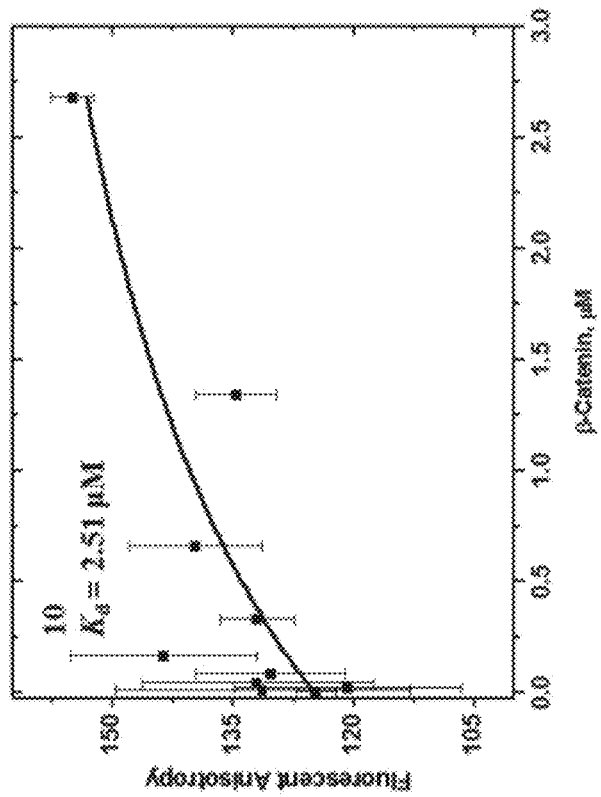
Figure 9L:
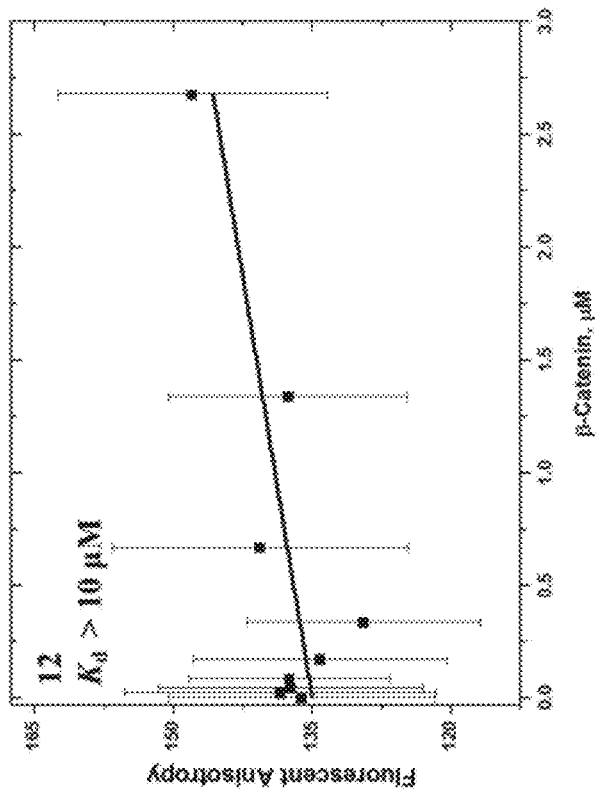
Figure 9K:
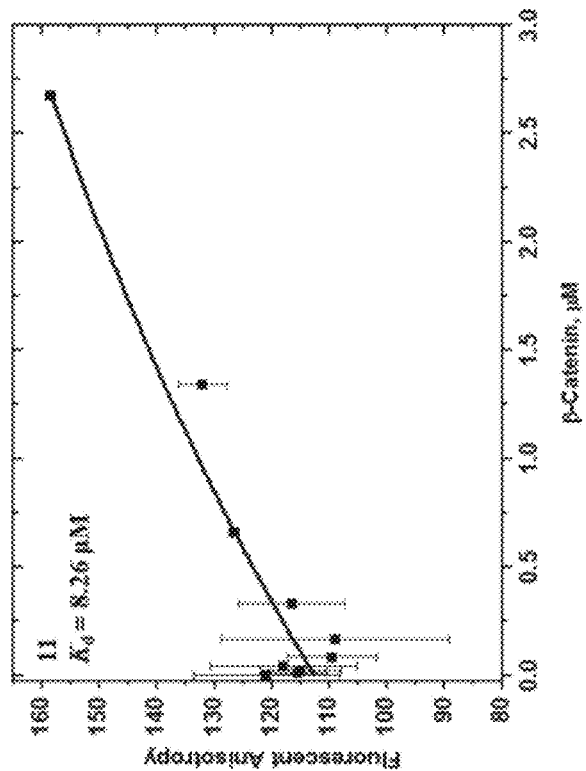
Figure 10B:
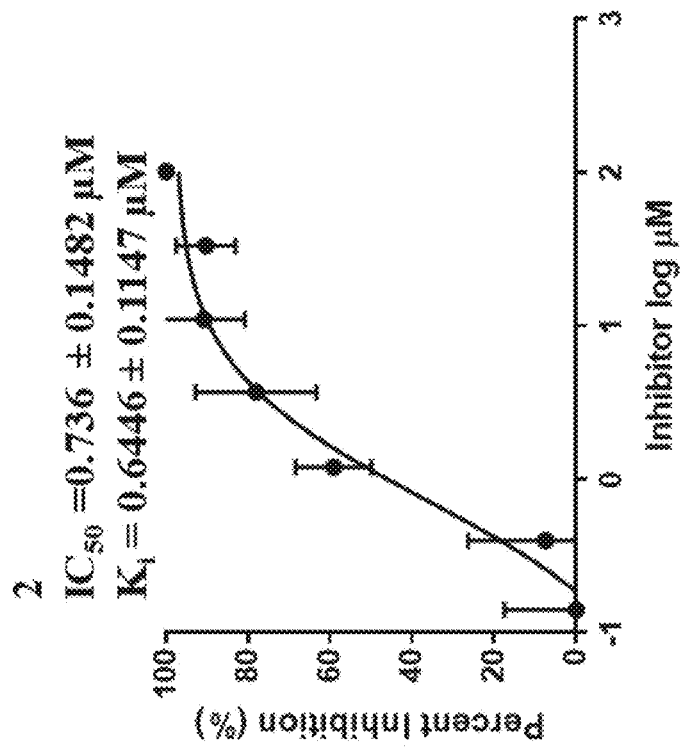
FIGS. 10A to 10K show Ki and IC50 data of regular peptide 1 (FIG. 10A) and sulfono-γ-AApeptides 2-11 (FIGS. 10B-10K).
Figure 10A:
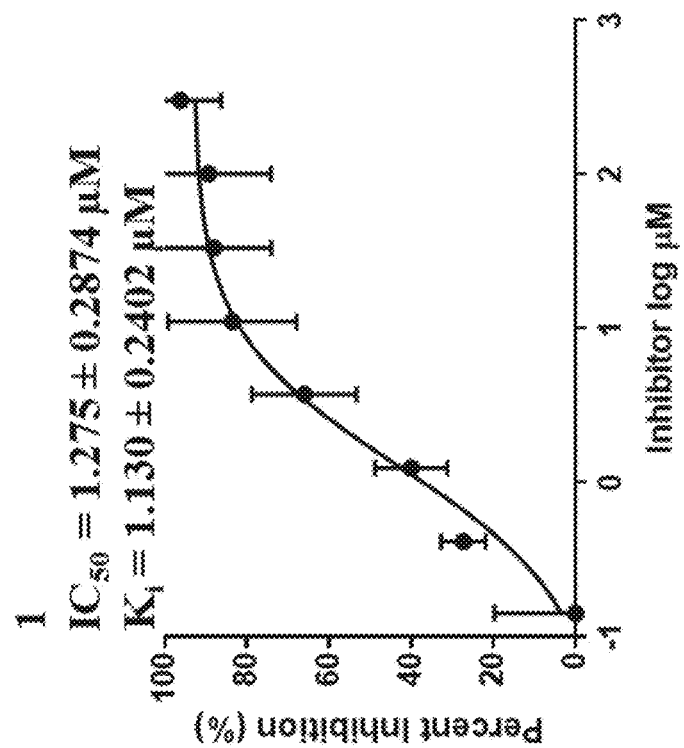
Figure 10D:
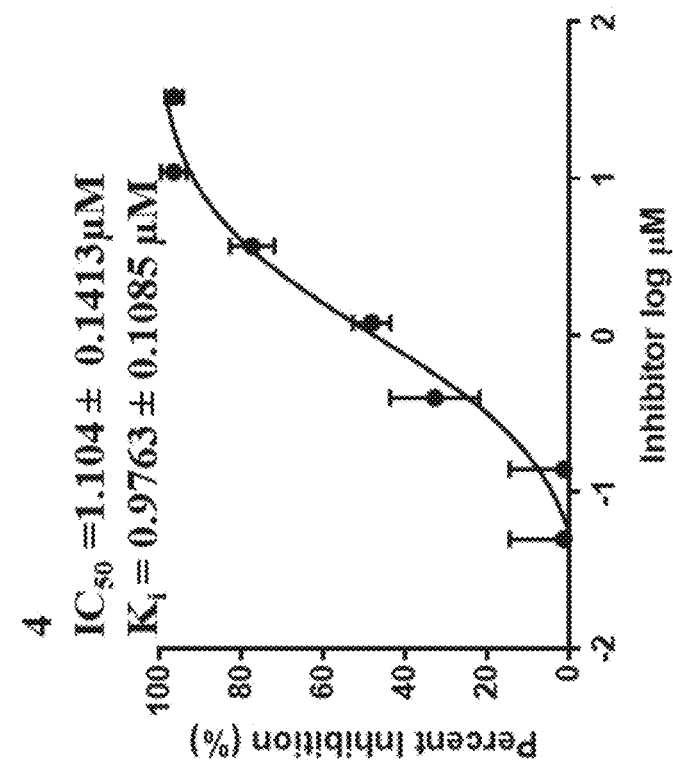
Figure 10C:
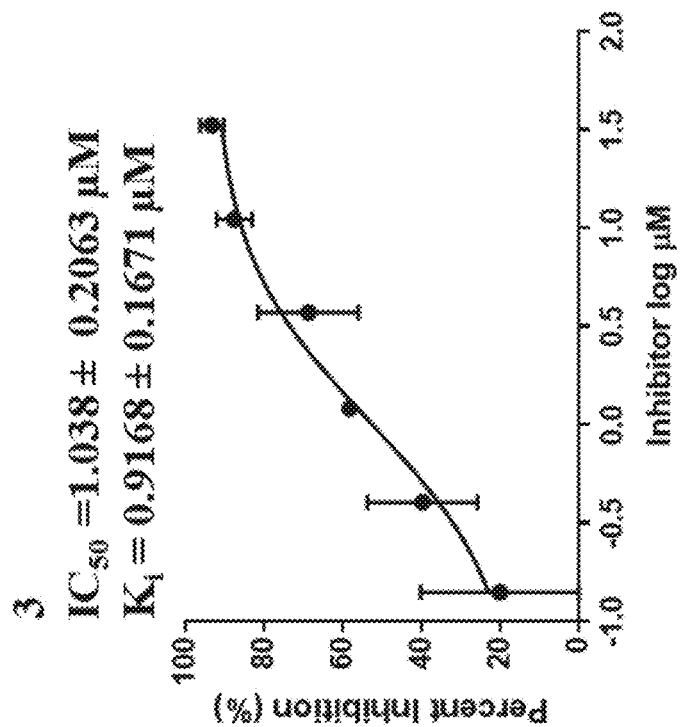
Figure 10F:
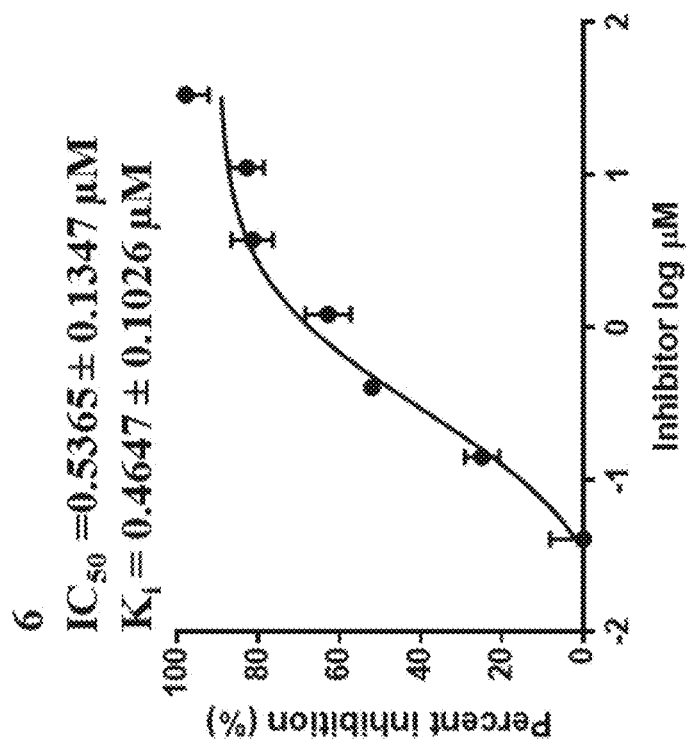
Figure 10E:
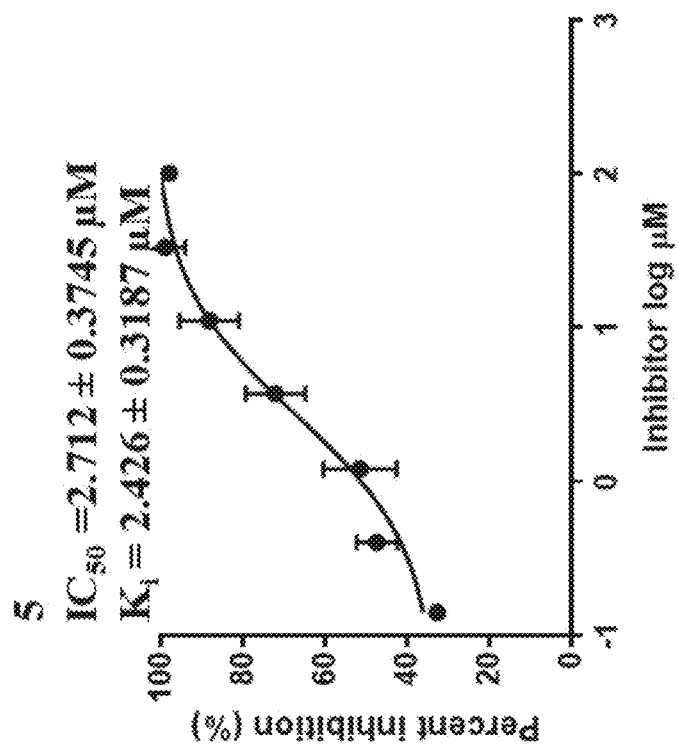
Figure 10H:
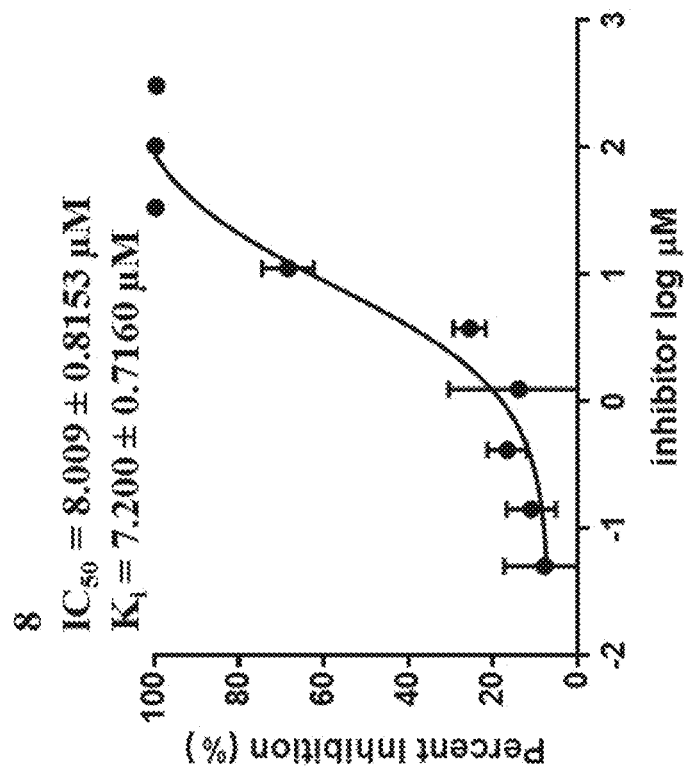
Figure 10G:
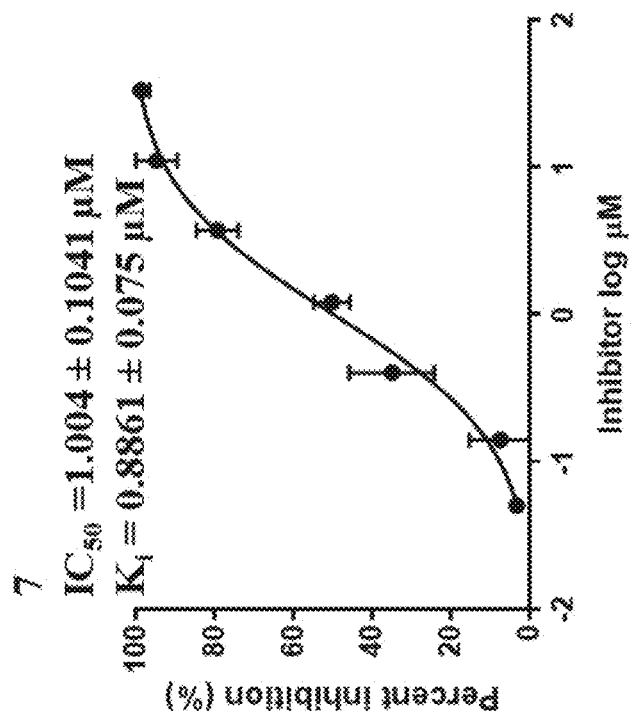
Figure 10J:
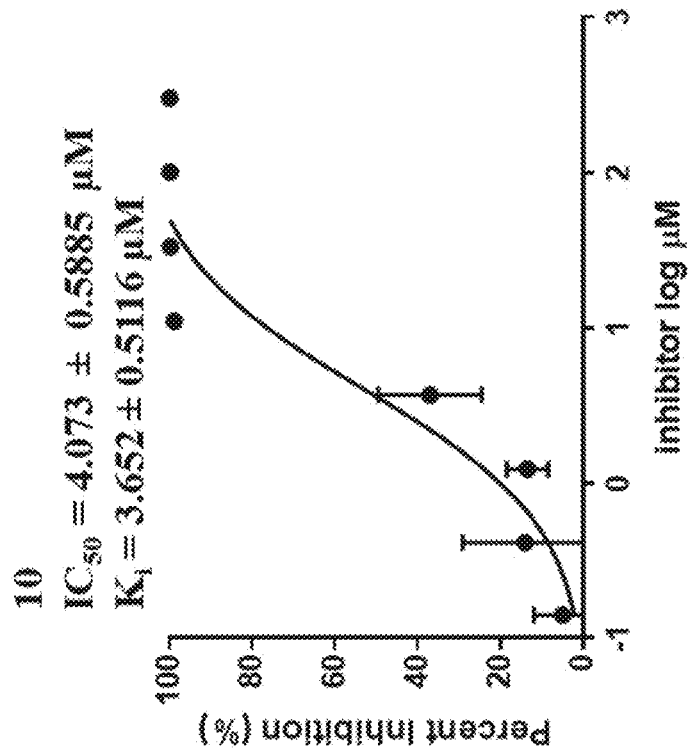
Figure 10I:
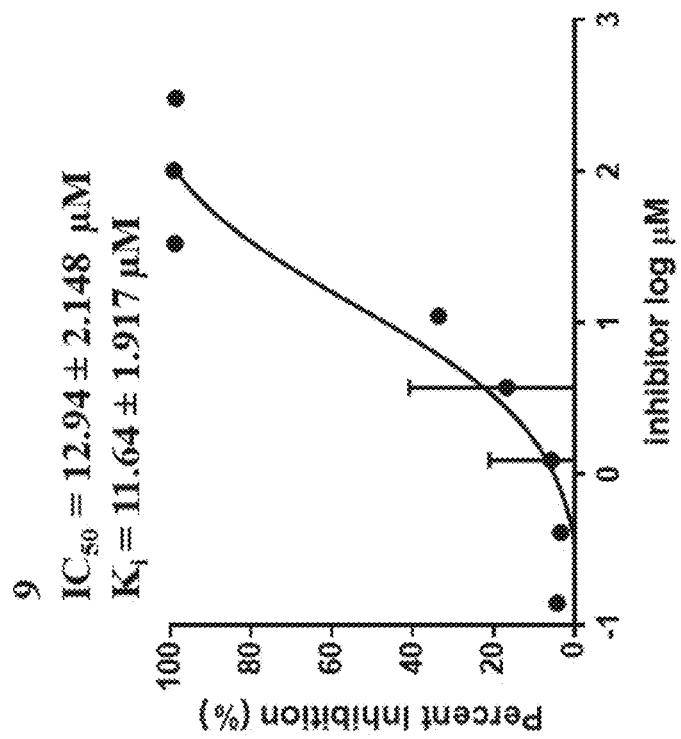
Figure 10K:
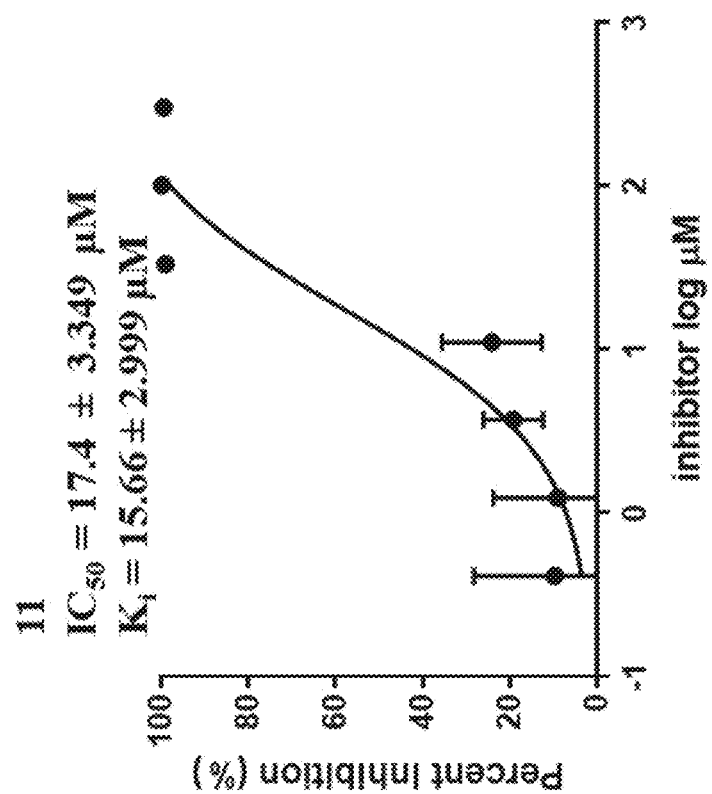

HRMS (ESI) ([M+H]$^+$) Calcd. for $C_{120}H_{231}N_{34}O_{37}S_{11}$: 3092.4167, found: 619.6883 [M+5H]$^{5+}$, 774.3566 [M+4H]$^{4+}$, 1032.1391 [M+3H]$^{3+}$, 1547.7030 [M+2H]$^{2+}$ (FIG. 8Z).

HPLC Purities and Retention Time of Pure Peptides.

TABLE 3

HPLC purities and retention time of regular peptide and sulfono-γ-AApeptides.[a]

| Peptide Name | Purity trace after HPLC purification (%) | Retention Time (min) |
|---|---|---|
| 1 | 100.0% | 18.10 |
| 2 | 100.0% | 21.58 |
| 3 | 99.09% | 22.31 |
| 4 | 100.0% | 22.48 |
| 5 | 98.76% | 20.22 |
| 6 | 97.98% | 20.30 |
| 7 | 97.87% | 20.59 |
| 8 | 100.0% | 22.23 |
| 9 | 100.0% | 19.18 |
| 10 | 98.96% | 22.26 |
| 11 | 99.76% | 20.86 |
| 12 | 100.0% | 21.66 |
| 1-FITC | 100.0% | 19.20 |
| 2-FITC | 100.0% | 22.60 |
| 3-FITC | 99.10% | 22.98 |
| 4-FITC | 98.79% | 23.00 |
| 5-FITC | 98.99% | 21.04 |
| 6-FITC | 99.01% | 21.51 |
| 7-FITC | 98.07% | 21.16 |
| 8-FITC | 99.99% | 21.23 |
| 9-FITC | 99.42% | 20.04 |
| 10-FITC | 99.19% | 23.49 |
| 11-FITC | 99.83% | 22.17 |
| 12-FITC | 100.0% | 22.95 |
| 3-Biotin | 98.71% | 21.47 |
| 4-Biotin | 100.0% | 21.47 |

[a]The gradient eluting method of 5% to 100% of solvent B (0.1% TFA in acetonitrile) in A (0.1% TFA in water) over 50 min was performed.

FP Assay to Measure the Binding of the Regular Peptide and Sulfono-γ-AApeptides with β-Catenin (Kd)

The binding affinity (Kd) of the regular amino acid and sulfono-γ-AApeptides was investigated by fluorescence polarization (FP). FP experiment was carried out by incubating 50 nM FITC labeled AApeptide with BCL9 (0.02 to 2.6 NM) in 1×PBS. Dissociation constants ($K_d$) were determined by plotting the fluorescence anisotropy values as a function of protein concentration, and the plots were fitted to the following equation. The Ln is the concentration of the peptide and the x stands for the concentration of the protein. The experiments were performed in triplicates and repeated for three times.

$$Y = [FPmin + (FPmin - FPmin)]\frac{\left(\frac{Kd+}{L_{st}}+x\right) - \sqrt{\left(\frac{Kd+}{L_{st}}+x\right)^2 - 4L_{st}x}}{2L_{st}}$$

FIGS. 9A to 9L show the &d data of regular peptide 1 and sulfono-γ-AApeptides 2-12.

Alphascreen Results of β-Catenin and BCL9 Interaction

For the competitive inhibition assays of β-catenin/BCL9 PPI, the negative control (equivalent to 0% inhibition) refers to 5.0 nM biotinylated BCL9, 40 nM His6-tagged FL-β-catenin, and 10 μg/mL of donor and acceptor beads in a final volume of 25 μL of assay buffer, but no tested inhibitor present. The positive control (equivalent to 100% inhibition) refers to 5.0 nM biotinylated BCL9 and 10 μg/mL of donor and acceptor beads in a final volume of 25 μL of assay buffer. For the β-catenin/BCL9 assay, 5 nM biotinylated BCL9 and 40 nM His6-tagged FL-β-catenin were incubated in assay buffer at 4° C. for 30 min. Different concentrations of the tested inhibitor were added and incubated in 20 μL of assay buffer at 4° C. for another 1 h. All of the above assay plates were covered and gently mixed on an orbital shaker. The donor and acceptor beads were then added to the plates to a final concentration of 10 µg/mL in 25 µL of assay buffer. The mixture was incubated for 1 h at 4° C. before detection. The $IC_{50}$ value was determined by nonlinear least-squares analysis of GraphPad Prism 5.0. The $K_i$ values were derived from the $IC_{50}$ values using a method reported by Nikolovska-Coleska et al. The assays were conducted under the conditions reported by Nikolovska-Coleska et al.'s equation for determining the $K_i$ values. All of the experiments were performed in triplicate. The results were expressed as mean±standard deviation.

FIGS. 10A to 10K show $K_i$ and $IC_{50}$ data of regular peptide 1 and sulfono-γ-AApeptides 2-11.

Circular Dichroism

Circular Dichroism (CD) spectra were measured on an Aviv 215 circular dichroism spectrometer using a 1 mm path length quartz cuvette, and compound solutions in PBS buffer were prepared using dry weight of the lyophilized solid followed by dilution to give the desired concentration (100 µM) and solvent combination. 10 scans were averaged for each sample, and 3 times of independent experiments were conducted and the spectra were averaged. The final spectra were normalized by subtracting the average blank spectra. Molar ellipticity [θ] (deg·cm2·dmol-1) was calculated using the equation:

$$[\theta]=\theta_{obs}/(n \times l \times c \times 10)$$

where Bobs is the measured ellipticity in millidegrees, while n is the number of side groups, l is path length in centimeter (0.1 cm), and c is the concentration of the sulfono-γ-AA peptide in molar units.

Figure 11:
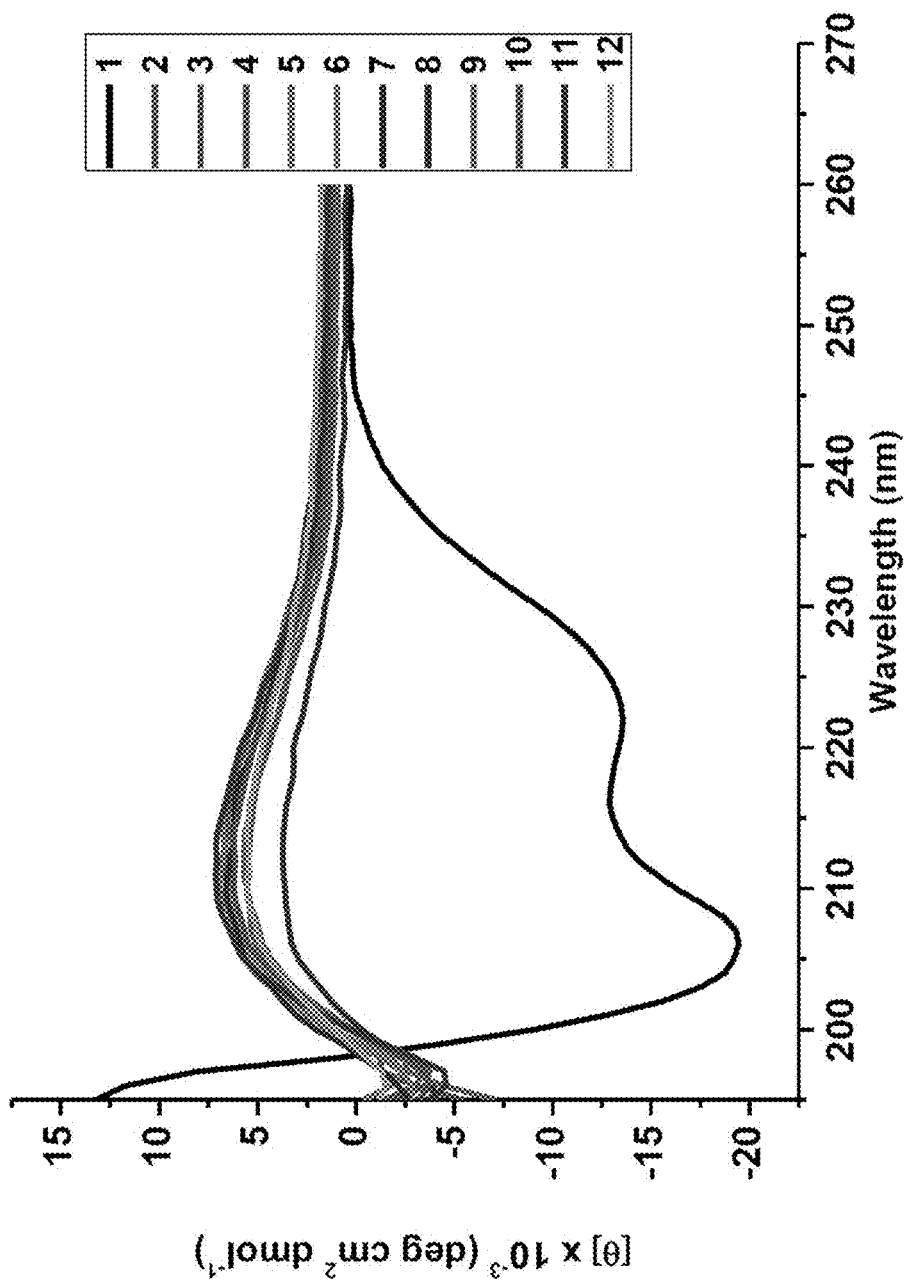
FIG. 11 shows circular dichroism spectra of regular peptide 1 and sulfono-γ-AApeptides 2-12 (100 μM) measured at room temperature in PBS buffer.
Figures 12E, 12F:
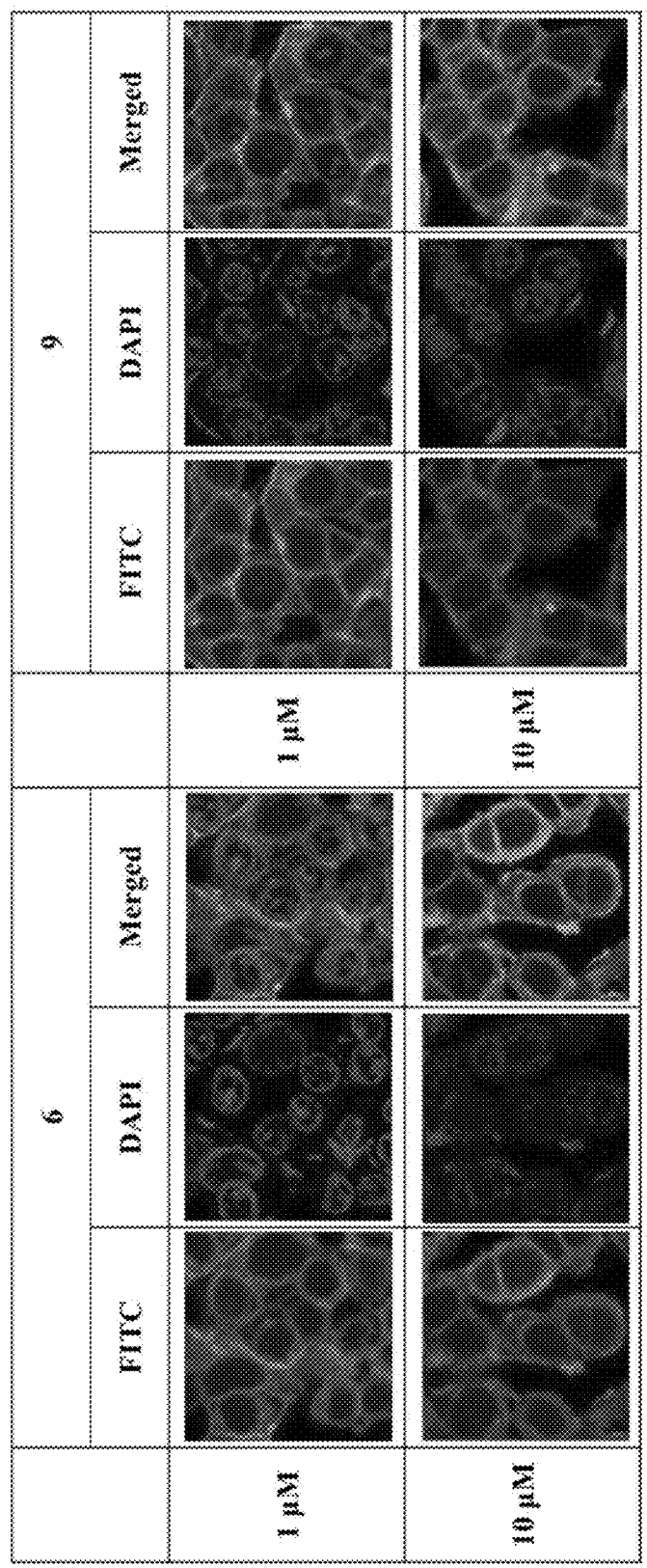

FIG. 11 shows circular dichroism spectra of regular peptide 1 and sulfono-γ-AApeptides 2-12 (100 µM) measured at room temperature in PBS buffer.

Cell Permeability Test

SW480 cells were plated on confocal dishes with 50% confluent and serum starved overnight, and then treated with different FITC-labeled peptides of 1 µM, and 10 µM for 2 hours. Then the cells were washed twice with PBS for 2 min. Next the cells were fixed with 100% MeOH for 5 min at room temperature, washed three times with PBS for 5 min. After which 0.1 µg/ml DAPI/PBS was added directly to cells in well, incubated for 15 min, washed with PBS, kept from light and observed by inverted microscope.

FIGS. 12A to 12F contain fluorescent microscopy images of SW480 cells treated with 1 µM and 10 µM of the FITC-labeled peptide 1 and sulfono-γ-AApeptides 2-4, 6 and 9 for 2 h.

MTs Cell Viability Assay

Colorectal cancer cell lines SW480 were seeded in 96-well plates at $5 \times 10^3$ cells/well, maintained overnight at 37° C., and incubated in the presence of inhibitors at various concentrations. Cell viability was monitored after 72 h using a freshly prepared mixture of one-part phenazine methosulfate (PMS, Sigma) solution (0.92 mg/mL) and 19 parts MTs agent (3-(4,5-dimethylthiazol-2-yl)-5-(3-carboxymethoxyphenyl)-2-(4-sulfophenyl)-2H-tetrazolium, inner salt, Promega) solution (2 mg/mL). Cells were incubated in 10 µL of this solution at 37° C. for 3 h, and A490 was measured. The effect of each compound is expressed as the concentration required to reduce A490 by 50% (IC50) relative to vehicle-treated cells. Experiments were performed in triplicate and repeated for three times.

TOPFlash/FOPFlash Luciferase Reporter Assay

FuGENE6 (E269A, Promega) 96-well plate format was used for the transfection of SW480 cells according to the manufacturer's instruction. SW480 cells were co-transfected with 60 ng of the TOPFlash or FOPFlash firefly luciferase reporter gene and 40 ng of renilla luciferase pCMV-RL normalization reporter. Cells were cultured in DMEM and 10% FBS at 37° C. for 24 h, and different concentrations of inhibitors or DMSO were added. After 24 h, the luciferase reporter activity was measured using the Dual-Glo system (E2940, Promega). Normalized luciferase activity in response to the treatment with inhibitors was compared with that obtained from the cells treated with DMSO. Experiments were performed in triplicate.

Figure 13B:
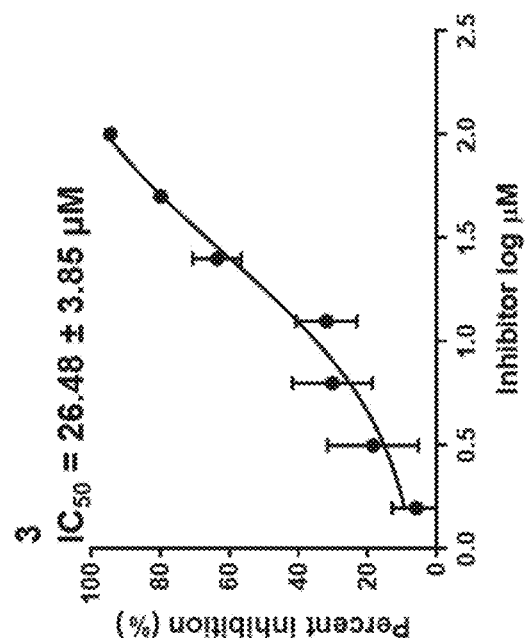
FIGS. 13A to 13C show Wnt-responsive TOPFlash luciferase reporter assay results of inhibitors 2 (FIG. 13A), 3 (FIG. 13B), and 4 (FIG. 13C) in β-catenin activated SW480 cells.
Figure 13A:
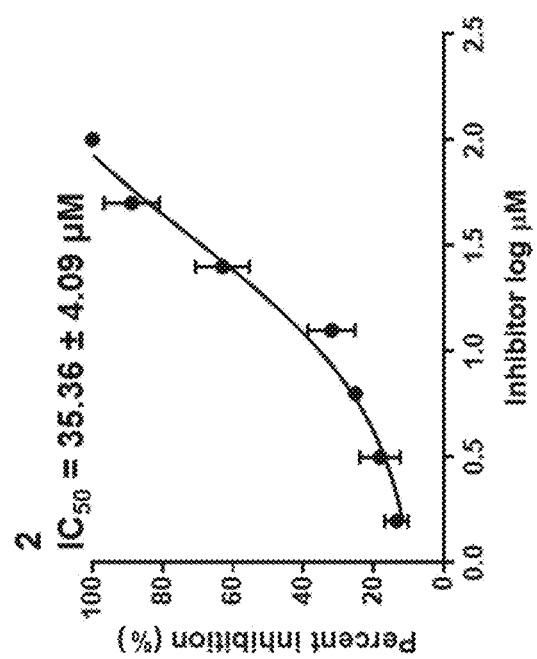
Figure 13C:
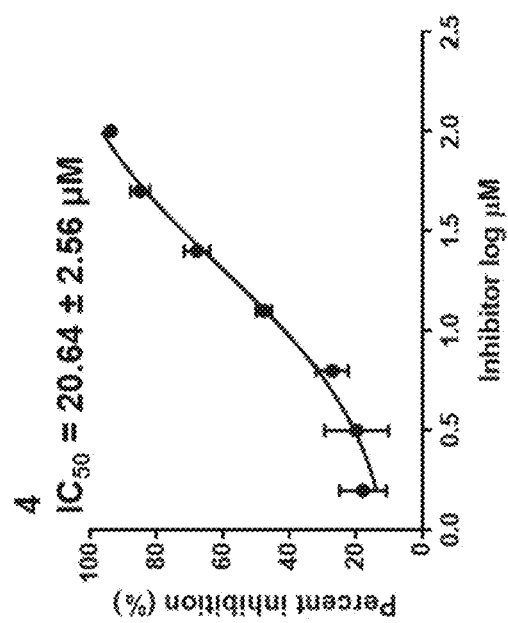

FIGS. 13A to 13C show Wnt-responsive TOPFlash luciferase reporter assay results of inhibitors 2-4 in β-catenin activated SW480 cells.

TABLE 4

Results of renilla luciferase reporter, the internal control of TOPFlash/FOPFlash reporter assays

| Compound | 0 µM | 12.5 µM | 25 µM | 50 µM |
|---|---|---|---|---|
| Average renilla values of TOPFlash luciferase reporter assays | | | | |
| 1 | 237 | 227 | 234 | 238 |
| 2 | 237 | 266 | 257 | 248 |
| 3 | 237 | 268 | 270 | 245 |
| 4 | 237 | 779 | 285 | 282 |
| Average Renilla values of FOPFlash luciferase reporter assays | | | | |
| 1 | 279 | 268 | 281 | 246 |
| 2 | 279 | 256 | 274 | 261 |
| 3 | 279 | 240 | 231 | 245 |
| 4 | 279 | 249 | 265 | 258 |

Pull-Down Experiments

Adherent β-catenin signaling hyperactive SW480 cancer cells (70-80% confluency) in T75 flask were lysed first in 1 mL buffer A containing 50 mM Tris (pH 7.4), 150 mM NaCl, 1% Nonidet β-40, 2 mM EDTA, and protease inhibitors. Cell debris was removed by centrifugation at 10,000 g for 20 min at 4° C. In 500 µL SW480 cell lysates, 1 µM biotinylated inhibitor was added in and incubated at 4° C. for 3 h. Then, 25 µL Streptavidin Sepharose beads (S-1638, Sigma) were added to the lysate mixture and rotated at 4° C. for 2 h. The lysate mixture was centrifuged at 4000 rpm for 2 min at 4° C. The beads were washed with buffer B (20 mM Tris pH 7.4, 150 mM NaCl, 0.05% NP-40) for 4 times. The beads were resuspended in 60 µL of 2×SDS sample buffer. After boiling, the samples were loaded onto 8% SDS polyacrylamide gel for electrophoretic analysis. Separated proteins were transferred onto nitrocellulose membranes for immunoblot analysis. The antibody against β-catenin (610153, BD Biosciences) were incubated with the membranes. IRDye 680LT goat anti-mouse IgG (827-11080, LiCOR) was used as the secondary antibody. The images were detected by the Odyssey Infrared Imaging System (LiCOR). Experiments were performed in duplicate.

Figure 14:
FIG. 14 shows results of pull-down experiments.

FIG. 14 shows results of pull-down experiments.

Co-Immunoprecipitation Experiments

β-Catenin signaling hyperactive HCT116 cancer cells at $1 \times 10^8$/mL were treated with different concentrations of the inhibitor for 24 h. Cells were then lysed in buffer containing 50 mM Tris, pH 7.4, 150 mM NaCl, 1% Nonidet β-40, 2 mM EDTA, and protease inhibitors. The cell lysates were then preadsorbed to A/G plus agarose (sc-2003, Santa Cruz Biotechnology) at 4° C. for 1 h. Preadsorbed lysates were incubated with a specific primary antibody against S-catenin (610153, BD Biosciences) overnight at 4° C. A/G plus agarose was then added to the lysate mixture and incubated for 3 h. The beads were washed four times with the lysis buffer at 4° C. The bound protein was eluted by boiling in the SDS sample buffer and loaded onto 8% SDS polyacrylamide gel for electrophoretic analysis. Separated proteins were transferred onto nitrocellulose membranes for immunoblot analysis. The antibodies against BCL9 (ab37305, Abcam), β-catenin (610153, BD Biosciences), and f-tubulin (sc-55529, Santa Cruz Biotechnology, Inc.) were incubated with the membranes, respectively. IRDye 680LT goat anti mouse IgG (827-11080, LiCOR) and IRDye 800CW goat anti rabbit IgG (926-32211, LiCOR) were used as the secondary antibodies. The images were detected by the Odyssey Infrared Imaging System (LiCOR). Experiments were performed in duplicate.

Figure 15:
FIG. 15 shows results of β-catenin immunoprecipitation (IP) and then BCL9 immunoblotting (IB).
Figure 16:
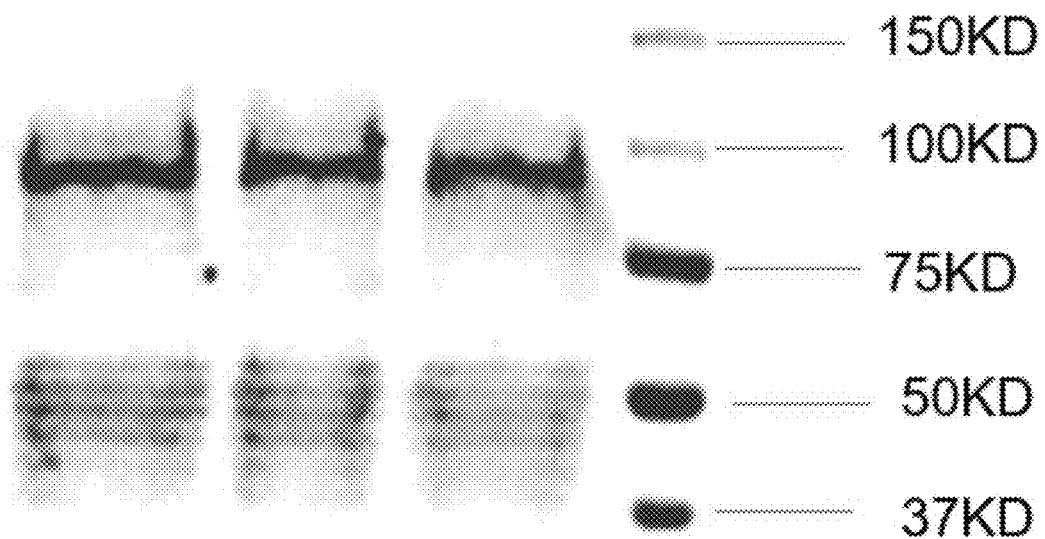
FIG. 16 shows results of β-catenin immunoprecipitation (IP) and then β-catenin immunoblotting (IB).
Figure 17:
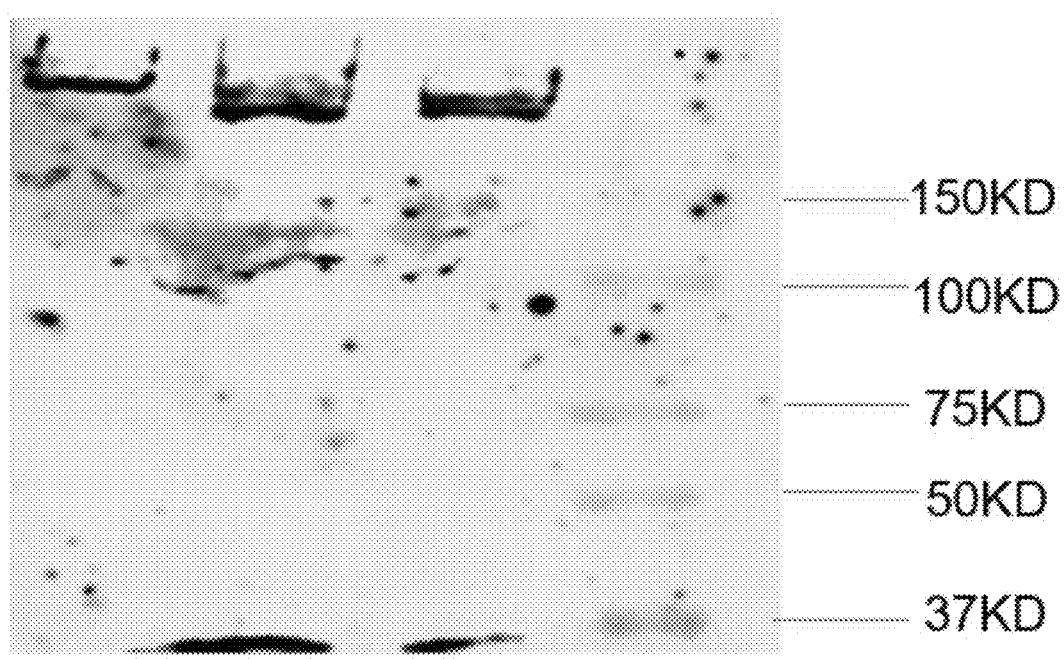
FIG. 17 shows results of BCL9 immunoblotting as the input.
Figure 18:
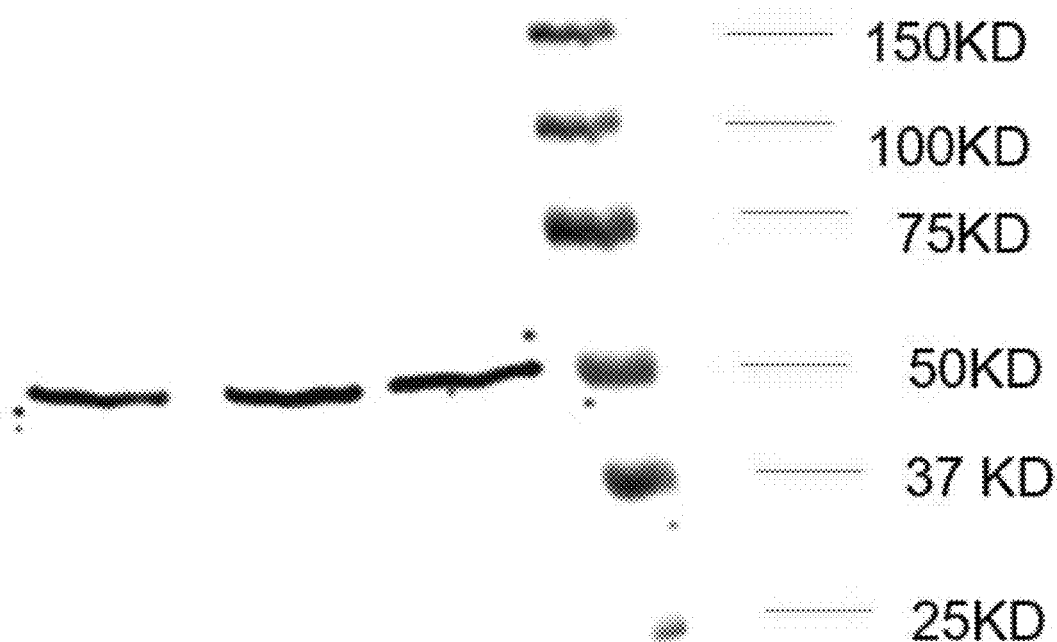
FIG. 18 shows results of β-tubulin immunoblotting as the input.

FIG. 15 shows results of β-catenin immunoprecipitation (IP) and then BCL9 immunoblotting (IB). FIG. 16 shows results of β-catenin immunoprecipitation (IP) and then β-catenin immunoblotting (IB). FIG. 17 shows results of BCL9 immunoblotting as the input. FIG. 18 shows results of β-tubulin immunoblotting as the input.

Enzymatic Stability Study

Lead Compounds 2-4 and peptide control 1 (0.1 mg/mL) were incubated with 0.1 mg/mL protease in 100 mM ammonium bicarbonate buffer (pH 7.8) at 37° C. for 24 h. Then, the reaction mixtures were concentrated in a speed vacuum at medium temperature to remove water and ammonium bicarbonate. The resulting residues were re-dissolved in $H_2O$/MeCN and analyzed on a Waters analytical HPLC system with 1 mL/min flow rate and 5% to 100% linear gradient of solvent B (0.1% TFA in acetonitrile) in A (0.1% TFA in water) over the duration of 50 min. The UV detector was set to 215 nm.

HPLC Traces of 1 in Presence of Pronase

FIG. 19 shows analytic HPLC trace of 1 before and after incubation with Pronase (0.1 mg/mL) in 100 mM pH 7.8 ammonium bicarbonate buffer at 37° C.

HPLC Traces of Lead Peptides in Presence of Proteases

Figure 20:
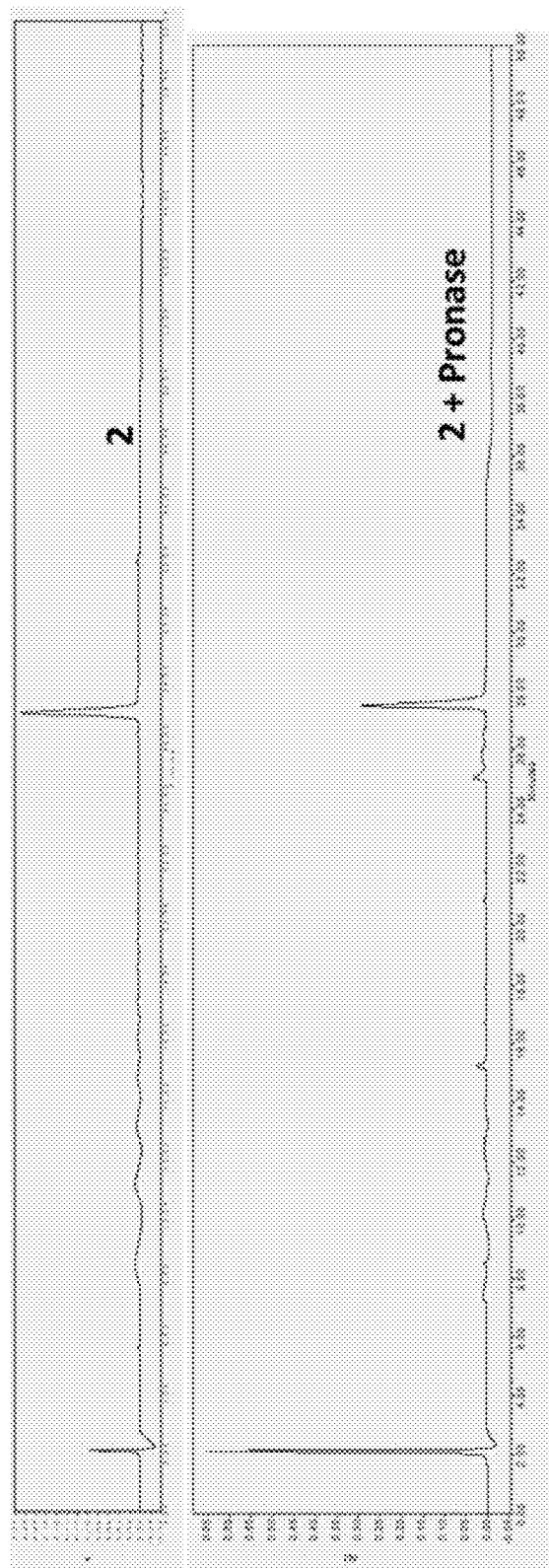
FIG. 20 shows analytic HPLC trace of 2 before and after incubation with Pronase (0.1 mg/mL) in 100 mM pH 7.8 ammonium bicarbonate buffer at 37° C.
Figure 21:
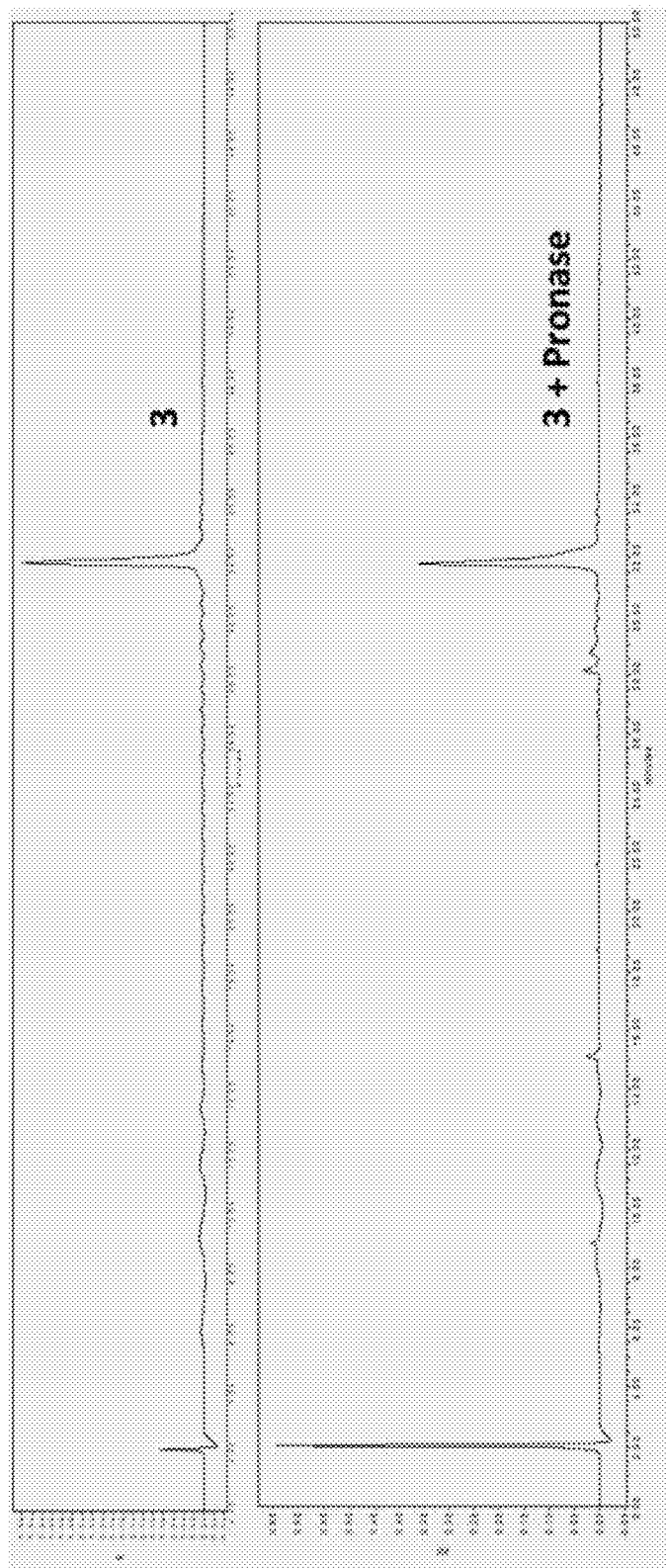
FIG. 21 shows analytic HPLC trace of 3 before and after incubation with Pronase (0.1 mg/mL) in 100 mM pH 7.8 ammonium bicarbonate buffer at 37° C.
Figure 22:
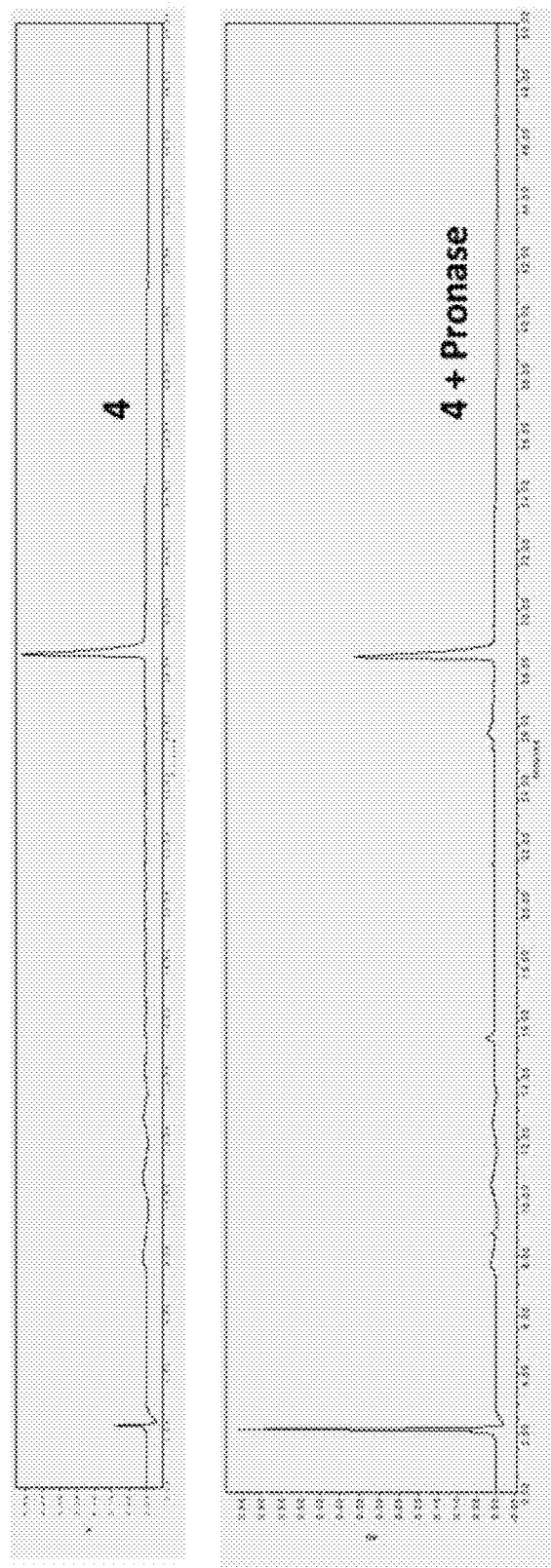
FIG. 22 shows analytic HPLC trace of 4 before and after incubation with Pronase (0.1 mg/mL) in 100 mM pH 7.8 ammonium bicarbonate buffer at 37° C.

FIG. 20 shows analytic HPLC trace of 2 before and after incubation with Pronase (0.1 mg/mL) in 100 mM pH 7.8 ammonium bicarbonate buffer at 37° C. FIG. 21 shows analytic HPLC trace of 3 before and after incubation with Pronase (0.1 mg/mL) in 100 mM pH 7.8 ammonium bicarbonate buffer at 37° C. FIG. 22 shows analytic HPLC trace of 4 before and after incubation with Pronase (0.1 mg/mL) in 100 mM pH 7.8 ammonium bicarbonate buffer at 37° C.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A sulfono-γ-AApeptide compound having the structure of Formula I:

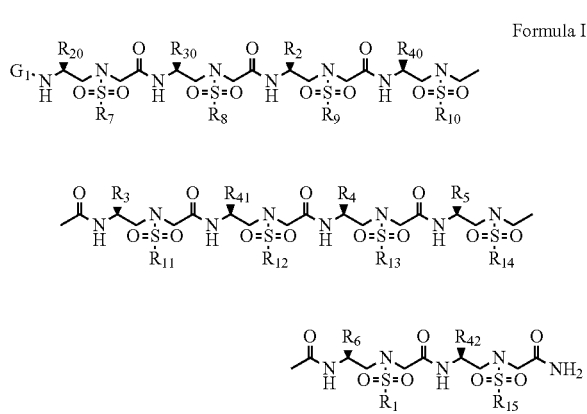

wherein $G_1$ is hydrogen, acetyl group, linker group, or a blocking group;

wherein $R_1$ is a hydrogen or $C_1$-$C_6$ alkyl;

wherein each of $R_2$, $R_4$, and $R_{30}$ is independently hydrogen, C1-C6 alkyl, or a group having a structure with the formula:

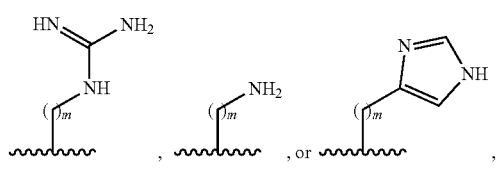

wherein m is an integer having a value of 0, 1, 2, 3, 4, 5, or 6;

wherein each of $R_3$, $R_5$, and $R_6$ is independently hydrogen, C1-C6 alkyl, or C1-C6 hydroxyalkyl;

wherein each of $R_7$, $R_{10}$, and $R_{12}$ is independently hydrogen, C1-C6 alkyl, C1-C6 hydroxyalkyl, or C1-C6 aminoalkyl;

wherein each of $R_8$, $R_9$, $R_{11}$, $R_{13}$, and $R_{14}$ is independently hydrogen or C1-C6 alkyl;

wherein $R_{15}$ is hydrogen, C1-C6 alkyl, aryl, or heteroaryl;

wherein $R_{20}$ is hydrogen, C1-C6 alkyl, C1-C6 hydroxyalkyl, C1-C6 aminoalkyl, -(C1-C6 alkanediyl)-(C=O) OH, or, -(C1-C6 alkanediyl)-(C=O) $NH_2$; and wherein each of $R_{40}$, $R_{41}$, and $R_{42}$ is independently is independently a C1-C6 alkyl;

or a pharmaceutically acceptable salt thereof.

2. The sulfono-γ-AApeptide compound of claim 1, wherein the sulfono-γ-AApeptide compound has the structure of Formula II:

Formula II

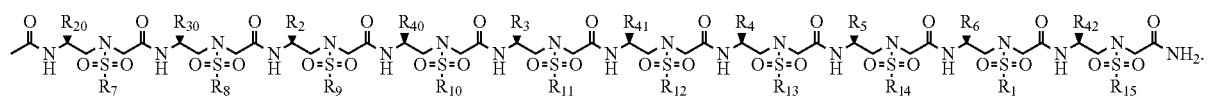

3. The sulfono-γ-AApeptide compound of claim 1, wherein the sulfono-γ-AApeptide compound has the structure of Formula III:

Formula III

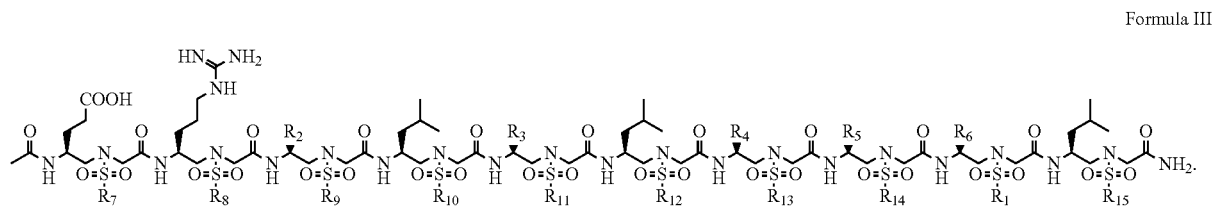

4. The sulfono-γ-AApeptide compound of claim 1, wherein the sulfono-γ-AApeptide compound has the structure of Formula IV:

Formula IV

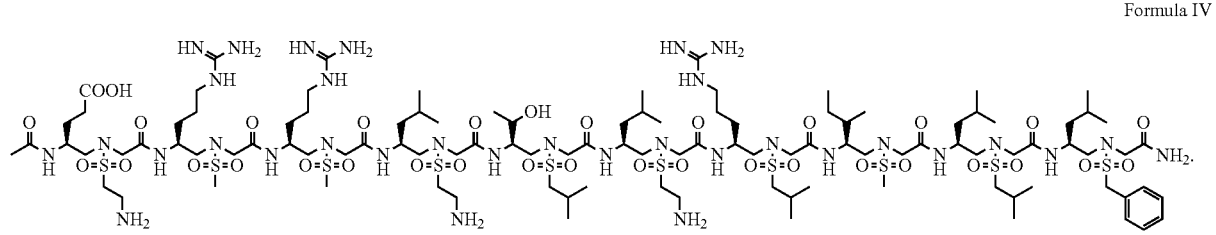 [SMILES: CCC(C)[C@@H](CN(CC(=O)N[C@@H](CC(C)C)CN(CC(=O)N[C@@H](CC(C)C)CN(CC(N)=O)S(=O)(=O)Cc1ccccc1)S(=O)(=O)CC(C)C)S(C)(=O)=O)NC(=O)CN(C[C@H](CCCNC(=N)N)NC(=O)CN(C[C@H](CC(C)C)NC(=O)CN(C[C@@H](NC(=O)CN(C[C@H](CC(C)C)NC(=O)CN(C[C@H](CCCNC(=N)N)NC(=O)CN(C[C@H](CCCNC(=N)N)NC(=O)CN(C[C@H](CCC(=O)O)NC(C)=O)S(=O)(=O)CCN)S(C)(=O)=O)S(C)(=O)=O)S(=O)(=O)CCN)C(C)O)S(=O)(=O)CC(C)C)S(=O)(=O)CCN)S(=O)(=O)CC(C)C]

5. The sulfono-γ-AApeptide compound of claim 1, wherein the sulfono-γ-AApeptide compound has the structure of selected from one of the following formulas:
Compound 2
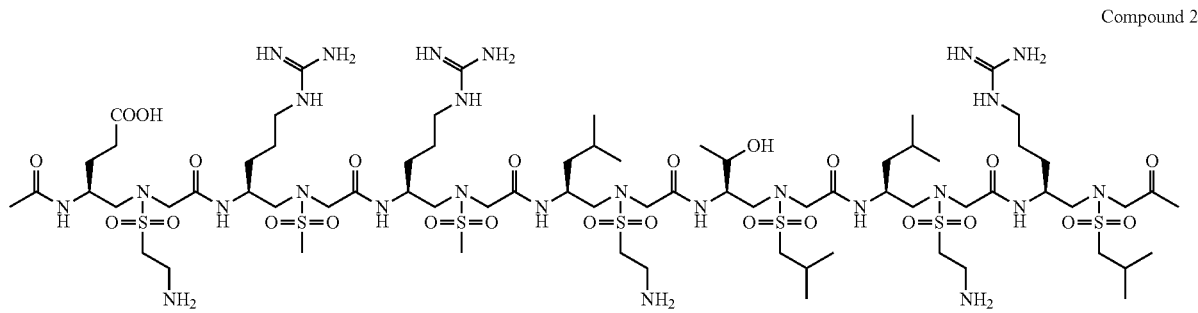
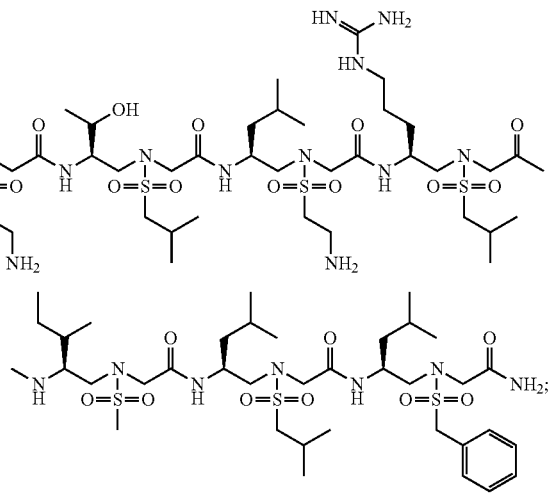
Compound 3
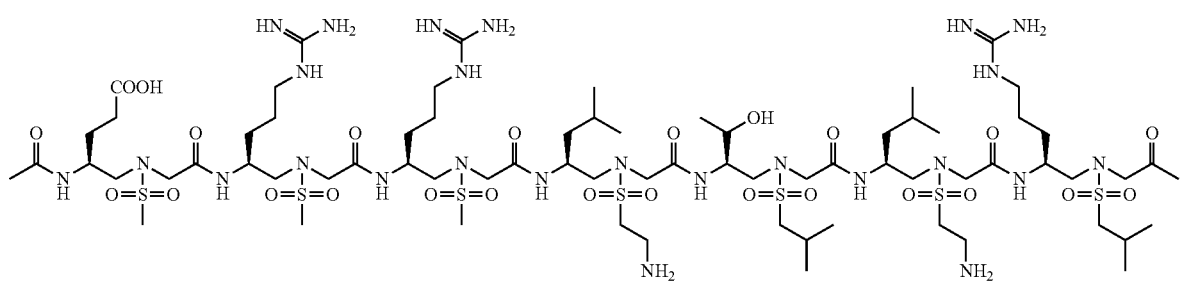
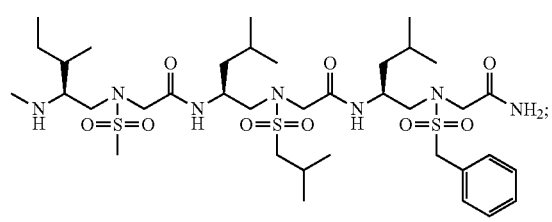
Compound 4
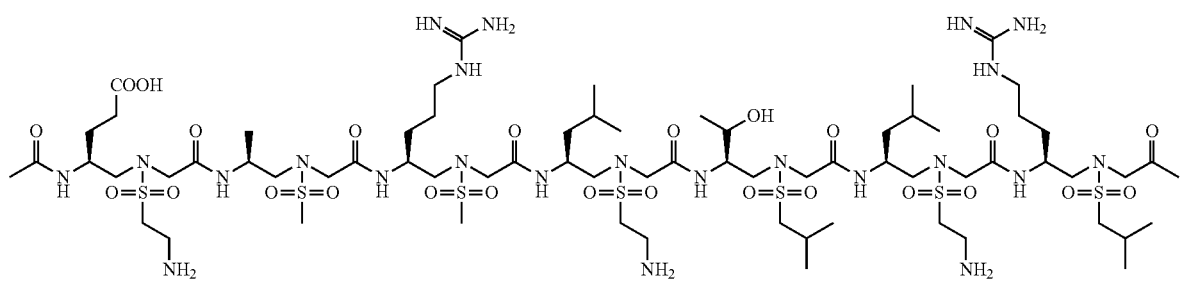
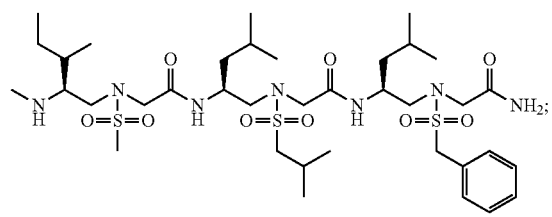

Compound 5
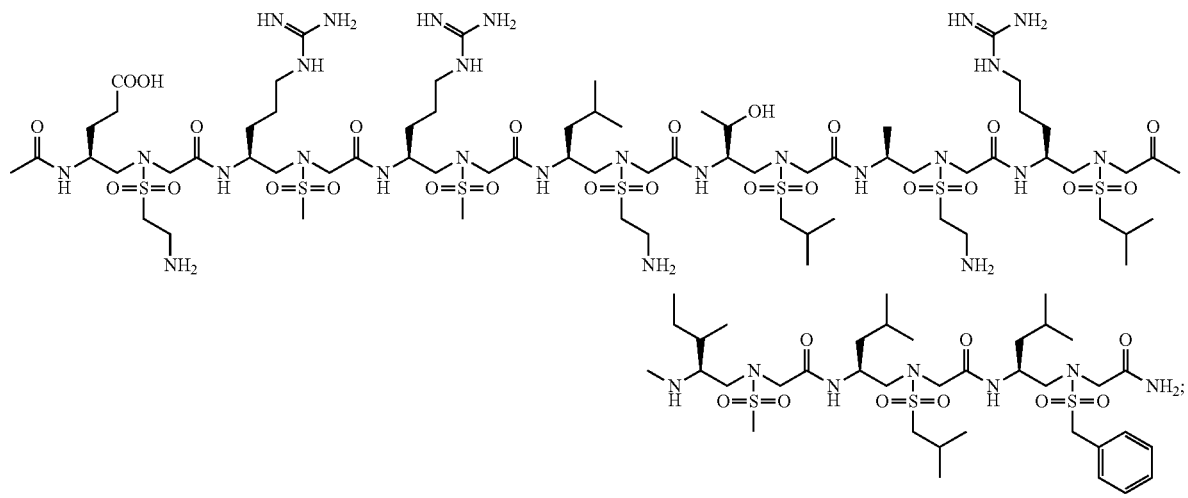
Compound 6
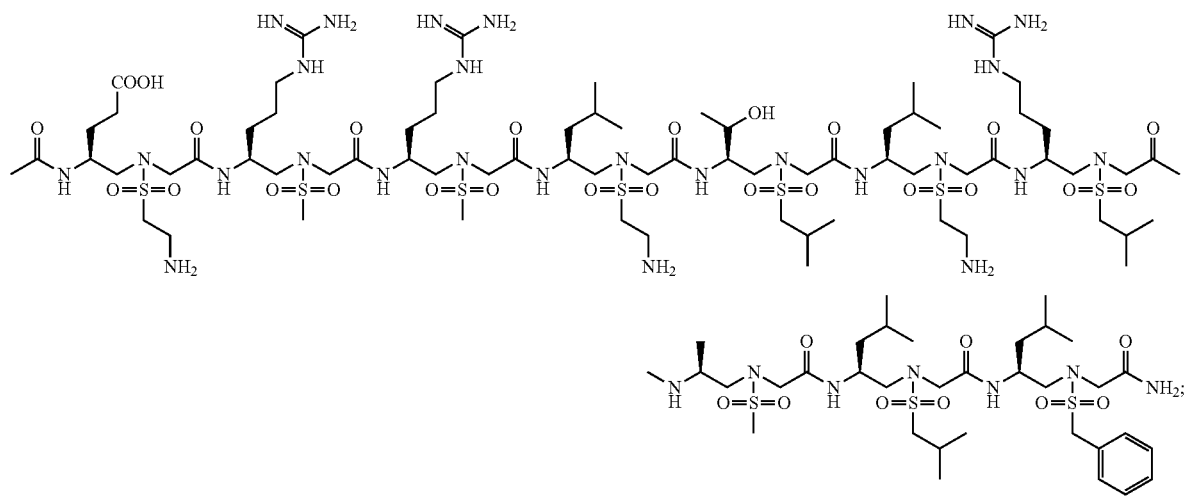
Compound 7
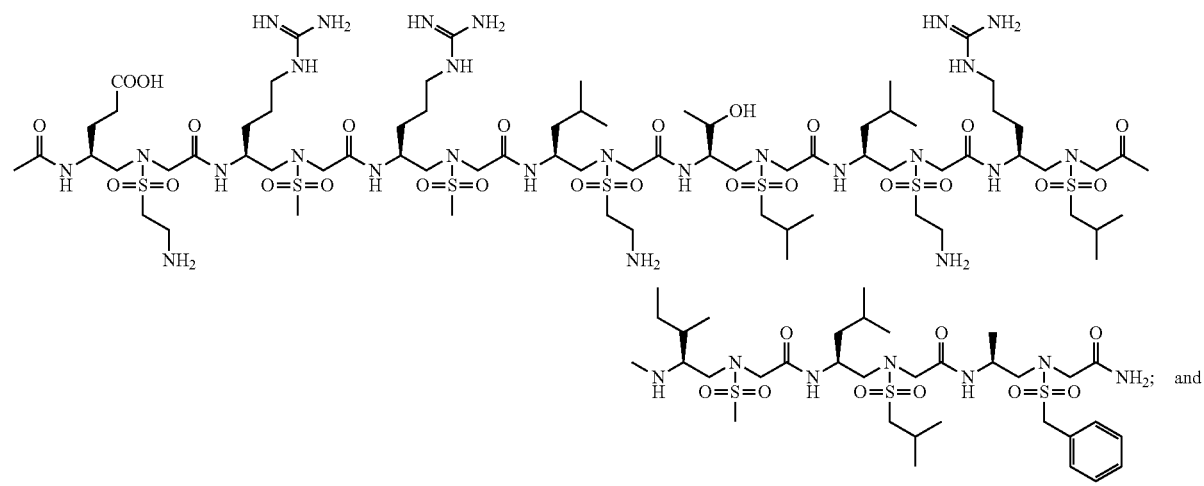

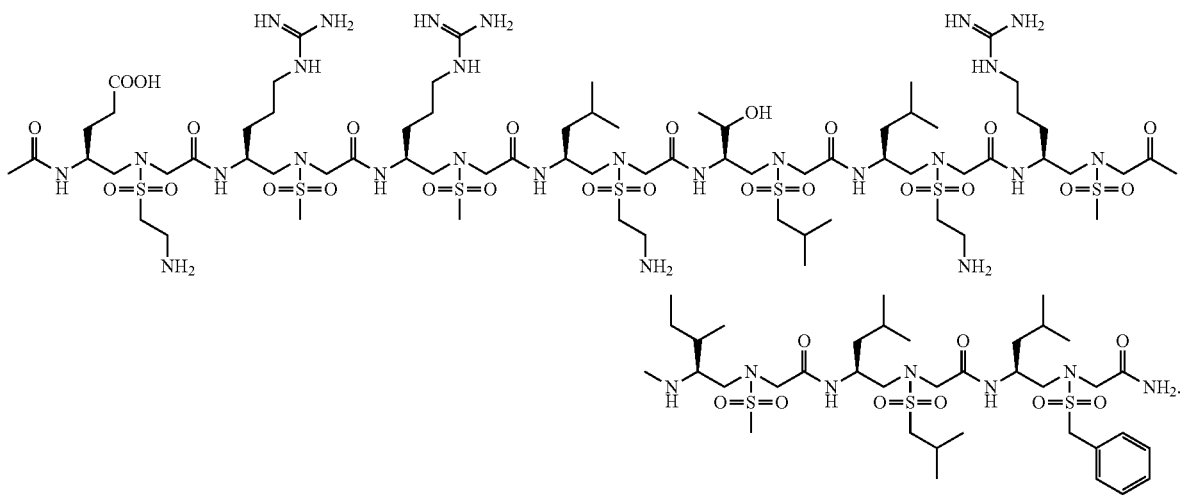

Compound 8

6. A pharmaceutical composition comprising the sulfono-γ-AApeptide compound of claim 1, or a pharmaceutically acceptable salt thereof, and a pharmaceutically acceptable excipient.

7. A method for treating a disease or disorder mediated by BCL9/β-catenin binding in a subject, comprising administering to the subject an effective amount of the pharmaceutical composition of claim 6 wherein the disease or disorder is colorectal cancer.

8. The method of claim 7, wherein the subject has been identified as being in need of an inhibitor of the BCL9/β-catenin interaction or Wnt signaling.

9. A method for treating cancer in a subject, comprising administering to the subject an effective amount of the pharmaceutical composition of claim 6 wherein the cancer is colorectal cancer.

10. The method of claim 9, further comprising administering to the subject an additional therapeutic agent, radiation or chemotherapy.

11. The method of claim 10, wherein the additional therapeutic agent is an anti-cancer compound.

12. The method of claim 10, wherein the sulfono-γ-AApeptide compound and the additional therapeutic agent are administered simultaneously or sequentially.

13. The method of claim 10, wherein the sulfono-γ-AApeptide compound and the additional therapeutic agent are administered in the same pharmaceutical composition.

* * * * *